US012766102B2

(12) United States Patent
Rizvi et al.

(10) Patent No.: US 12,766,102 B2
(45) Date of Patent: Oct. 20, 2026

(54) LIPOSOMES AND METHODS OF MAKING THE SAME

(71) Applicant: CORNELL UNIVERSITY, Ithaca, NY (US)

(72) Inventors: Syed S.H. Rizvi, Ithaca, NY (US); Apratim Jash, Ithaca, NY (US); Ali Ubeyitogullari, Fayetteville, AR (US)

(73) Assignee: Cornell University, Ithaca, NY (US)

( * ) Notice: Subject to any disclaimer, the term of this patent is extended or adjusted under 35 U.S.C. 154(b) by 960 days.

(21) Appl. No.: 17/862,310

(22) Filed: Jul. 11, 2022

(65) Prior Publication Data

US 2023/0023038 A1 Jan. 26, 2023

Related U.S. Application Data

(60) Provisional application No. 63/220,352, filed on Jul. 9, 2021.

(51) Int. Cl.

| | |
|---|---|
| ***A61K 9/127*** | (2025.01) |
| ***A23J 1/20*** | (2006.01) |
| ***A61K 8/14*** | (2006.01) |
| ***A61K 8/55*** | (2006.01) |
| ***A61K 9/1276*** | (2025.01) |
| ***A61K 9/1277*** | (2025.01) |
| ***A61K 47/24*** | (2006.01) |

(52) U.S. Cl.

CPC ............. *A61K 9/1276* (2013.01); *A23J 1/205* (2013.01); *A61K 8/14* (2013.01); *A61K 8/553* (2013.01); *A61K 9/1277* (2013.01); *A61K 47/24* (2013.01)

(58) Field of Classification Search

CPC ........ A61K 9/1276; A61K 8/14; A61K 8/553; A61K 9/1277; A61K 47/24; A61K 2800/10; A61K 8/986; A61K 9/0053; A61K 9/1271; A61K 31/355; A61K 31/375; A23J 1/205; A23J 7/00; A61Q 19/00; Y02P 20/54

See application file for complete search history.

(56) References Cited

U.S. PATENT DOCUMENTS

| | | | |
|---|---|---|---|
| 2011/0098254 | A1 | 4/2011 | Brown et al. |
| 2011/0195128 | A1 | 8/2011 | Palmano et al. |
| 2022/0125808 | A1 | 4/2022 | Hallaraker et al. |

FOREIGN PATENT DOCUMENTS

| | | | |
|---|---|---|---|
| CN | 111012671 | A | 4/2002 |
| CN | 103385853 | A | 11/2013 |
| CN | 203389560 | U | 1/2014 |
| CN | 110051649 | A | 7/2019 |
| CN | 109718205 | B | 4/2021 |
| WO | 2010/026229 | A1 | 3/2010 |

OTHER PUBLICATIONS

M. Ota, et al. "Supercritical Fluid Extraction of High-value Natural Products from Buttermilk Analyzed by a Dynamic Extraction Model," Nippon Shokuhin Kagaku Kodaku Kaishi, 65(5), 251-258, 2018. (Year: 2018).*

English Translation of M. Ota, et al. "Supercritical Fluid Extraction of High-value Natural Products from Buttermilk Analyzed by a Dynamic Extraction Model," Nippon Shokuhin Kagaku Kodaku Kaishi, 65(5), 251-258, 2018, provided by the PTO. (Year: 2025).*

S.M. Ghoreishi, et al. "Optimization of periodic static-dynamic supercritical CO2 extraction of taxifolin from pinus nigra bark with ethanol as entrainer," J. of Supercritical Fluids 113 (2016) 53-60. (Year: 2016).*

Dielectric Constant Table from CEM (Year: 2025).*

Astaire, et al., "Concentration of Polar MFGM Lipids from Buttermilk by Microfiltration and Supercritical Fluid Extraction," J. Dairy Sci. 86 (2003).

Jiménez-Flores, et al., "The milk fat globule membrane as an ingredient: why, how, when?" Dairy Sci. Technol. 88 (2008).

Jash, et al., "Synthesis of multivitamin-loaded heat stable liposomes from milk fat globule membrane phospholipids by using a supercritical-CO2 based system," Green Chem., 2020, 22, 5345. Jash, et al., "Innovative Food Science and Emerging Technologies," Innovative Food Science and Emerging Technologies (2021), https://doi.org/10.1016/j.ifset.2022.103030.

Mohammadi, et al., "Encapsulation of vitamins using nanoliposome: recent advances and perspectives," Advanced Pharmaceutical Bulletin, doi: 10.34172/apb.2023.005.

Ubeyitogullari, et al., "Production of high-purity phospholipid concentrate from buttermilk powder using ethanol-modified supercritical carbon dioxide," J. Dairy Sci. 103 (2020).

* cited by examiner

*Primary Examiner* — Michael P Cohen

(74) *Attorney, Agent, or Firm* — Young Basile Hanlon & MacFarlane, P.C

(57) ABSTRACT

Milk fat globule membrane (MFGM) phospholipid compositions, methods of preparing and using the MFGM phospholipid compositions, liposomes comprising the MFGM phospholipid compositions, and methods of preparing and using the liposomes comprising the MFGM phospholipid compositions. In various examples, a MFGM phospholipid composition is formed by sequential supercritical carbon dioxide (SC-$CO_2$) extraction of a milk product and extraction of the remaining milk product with a polar compound-modified SC-$CO_2$ extraction, where the extract is the MFGM. In various examples, the MFGM is used to prepare liposomes. In various examples, the liposomes are prepared by expansion of a supercritical solution comprising the MFGM composition. In various examples, the liposomes are used to administer a cargo, such as, for example, hydrophilic compound(s), hydrophobic compound(s), amphiphilic compound(s), or the like, any one or all of which may be therapeutic agent(s), nutrient(s), bioagent(s), or the like, or any combination thereof to a subject.

11 Claims, 35 Drawing Sheets

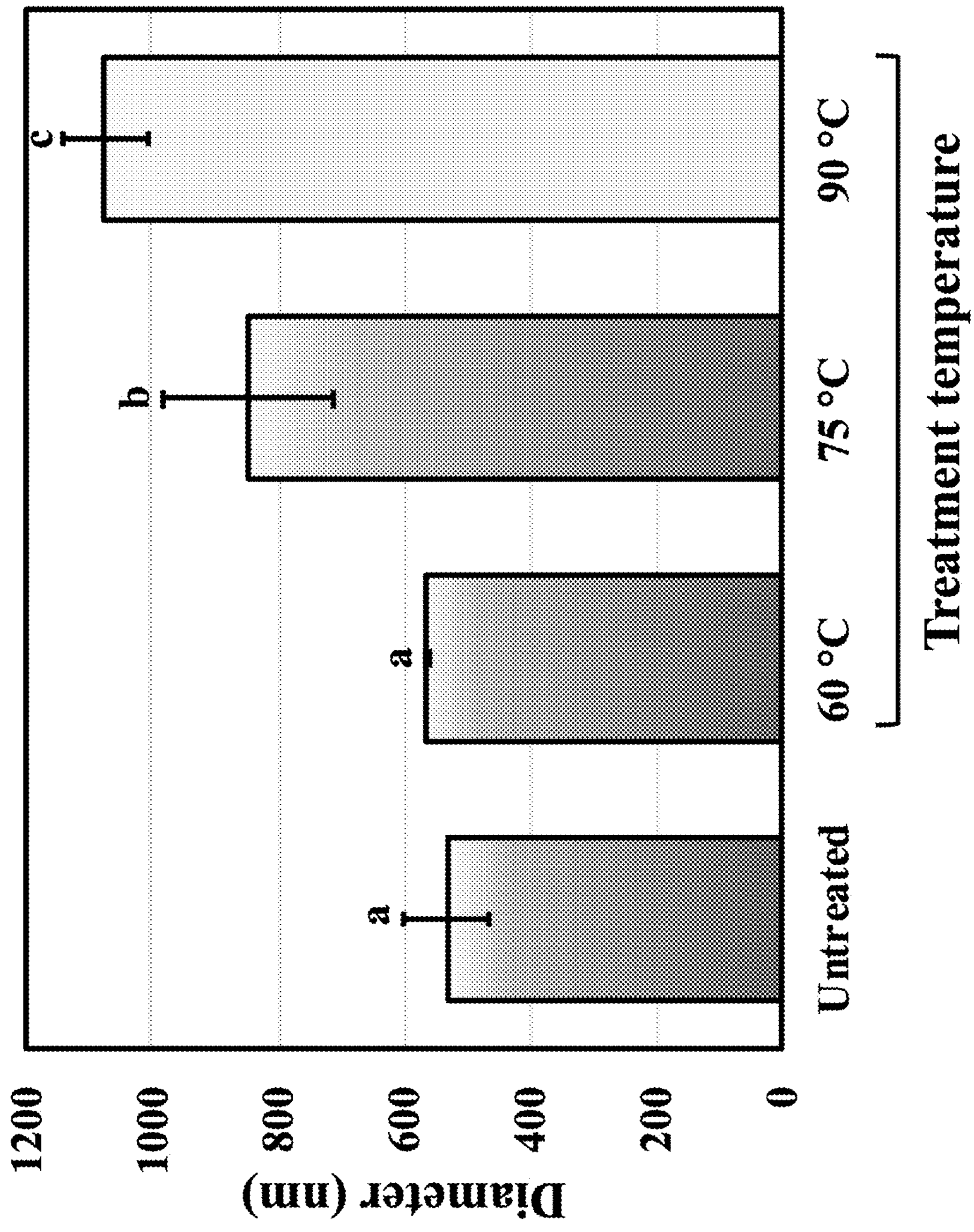
FIG. 9A(1)

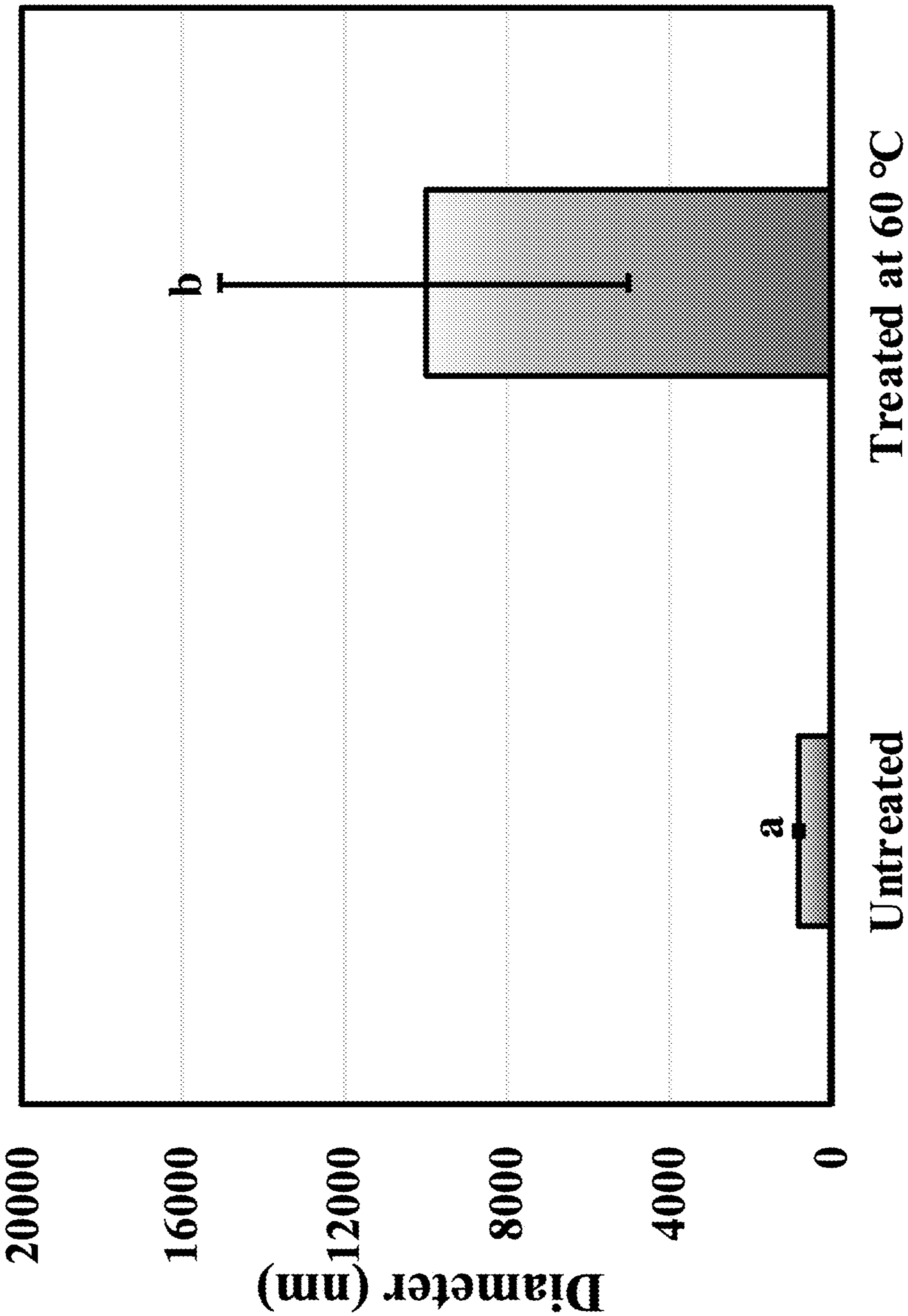
FIG. 9A(2)

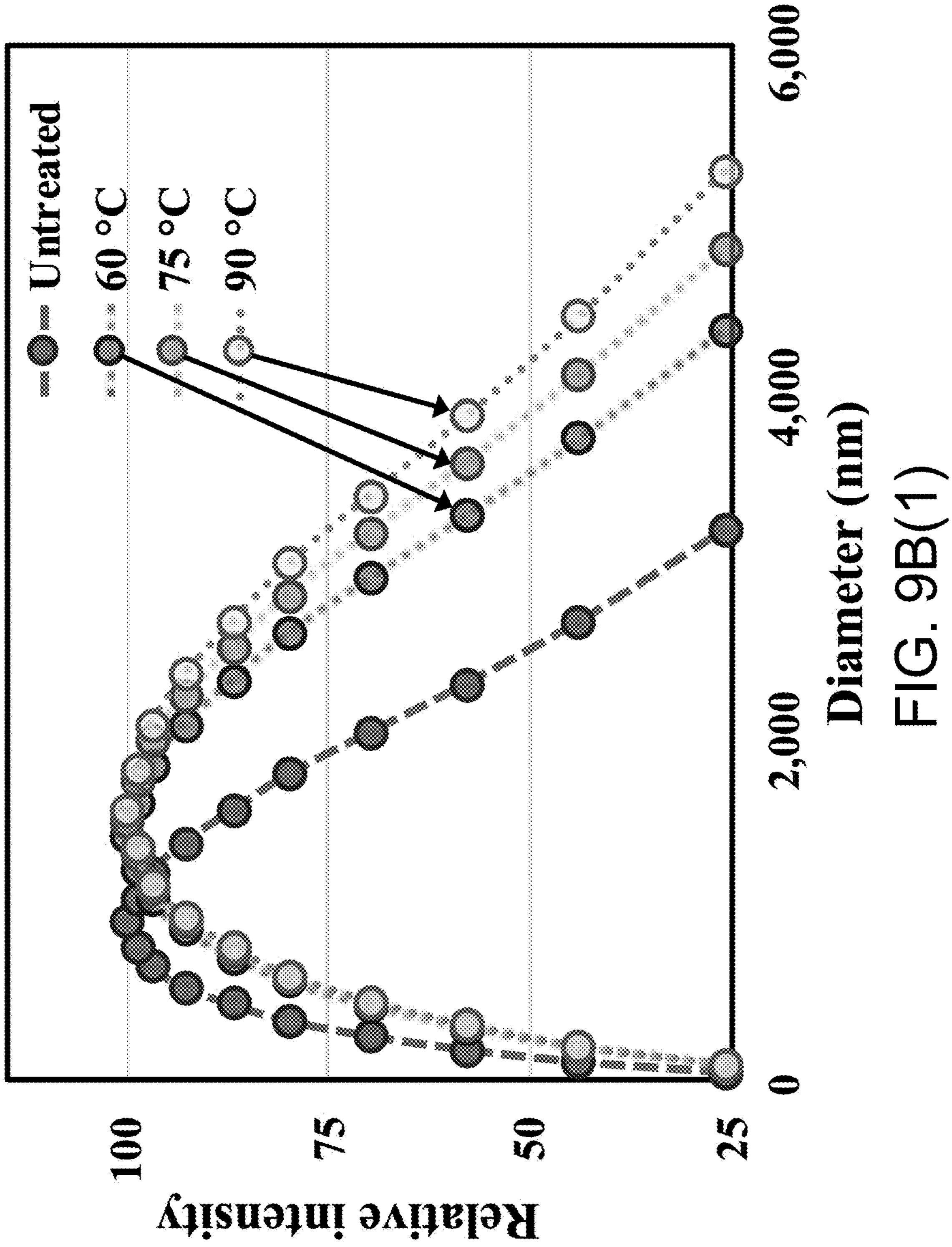
FIG. 9B(1)

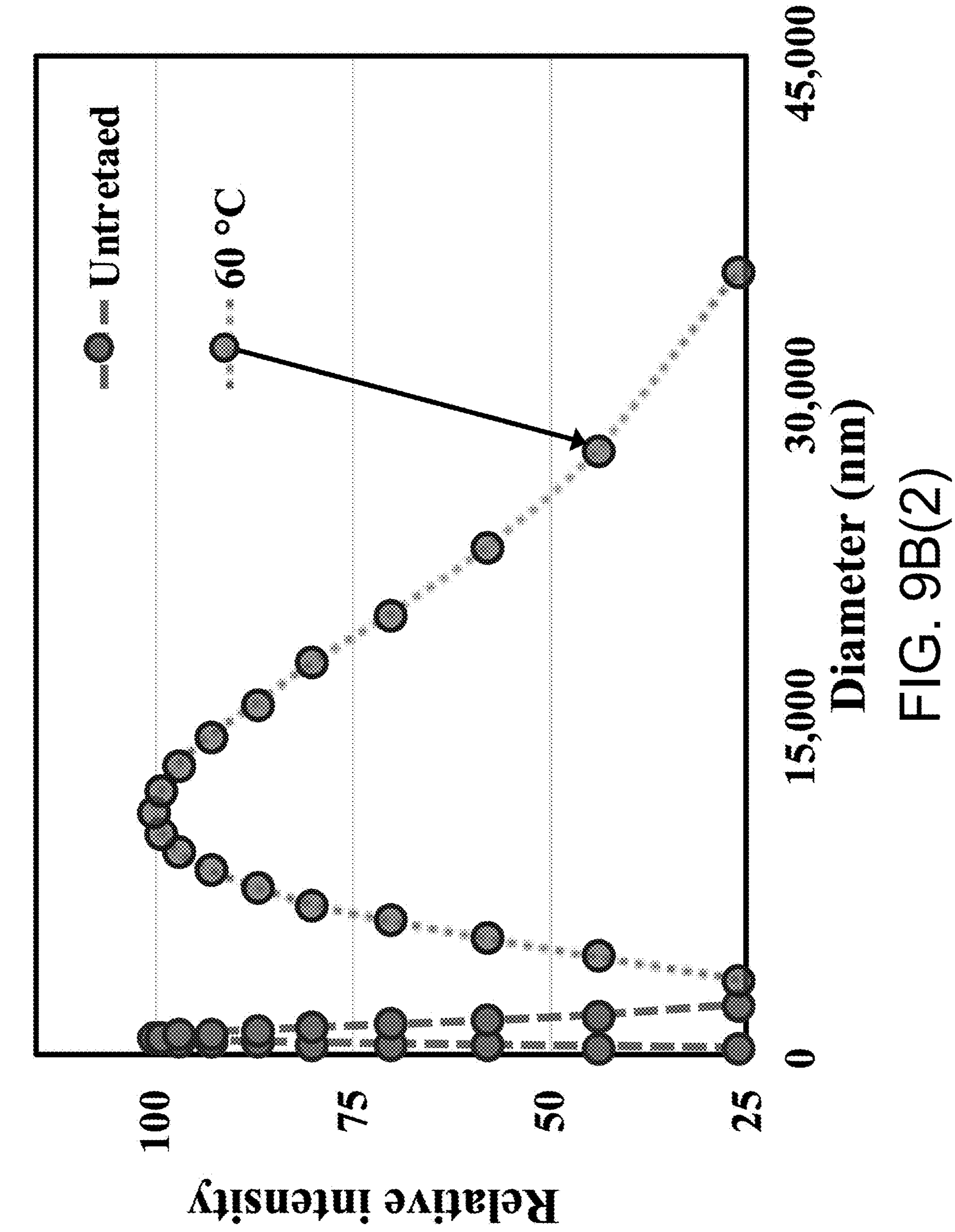
FIG. 9B(2)

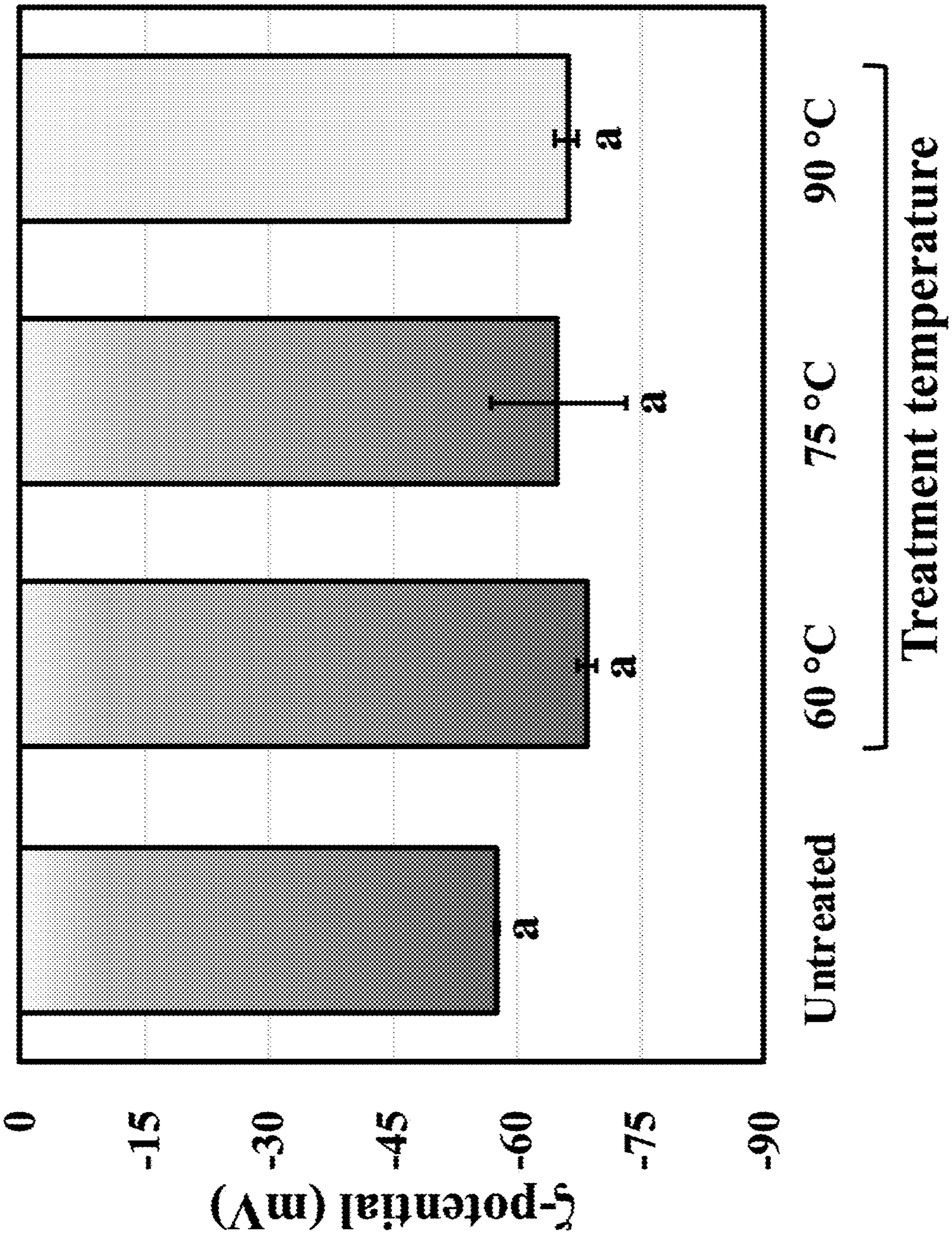
FIG. 9C(1)

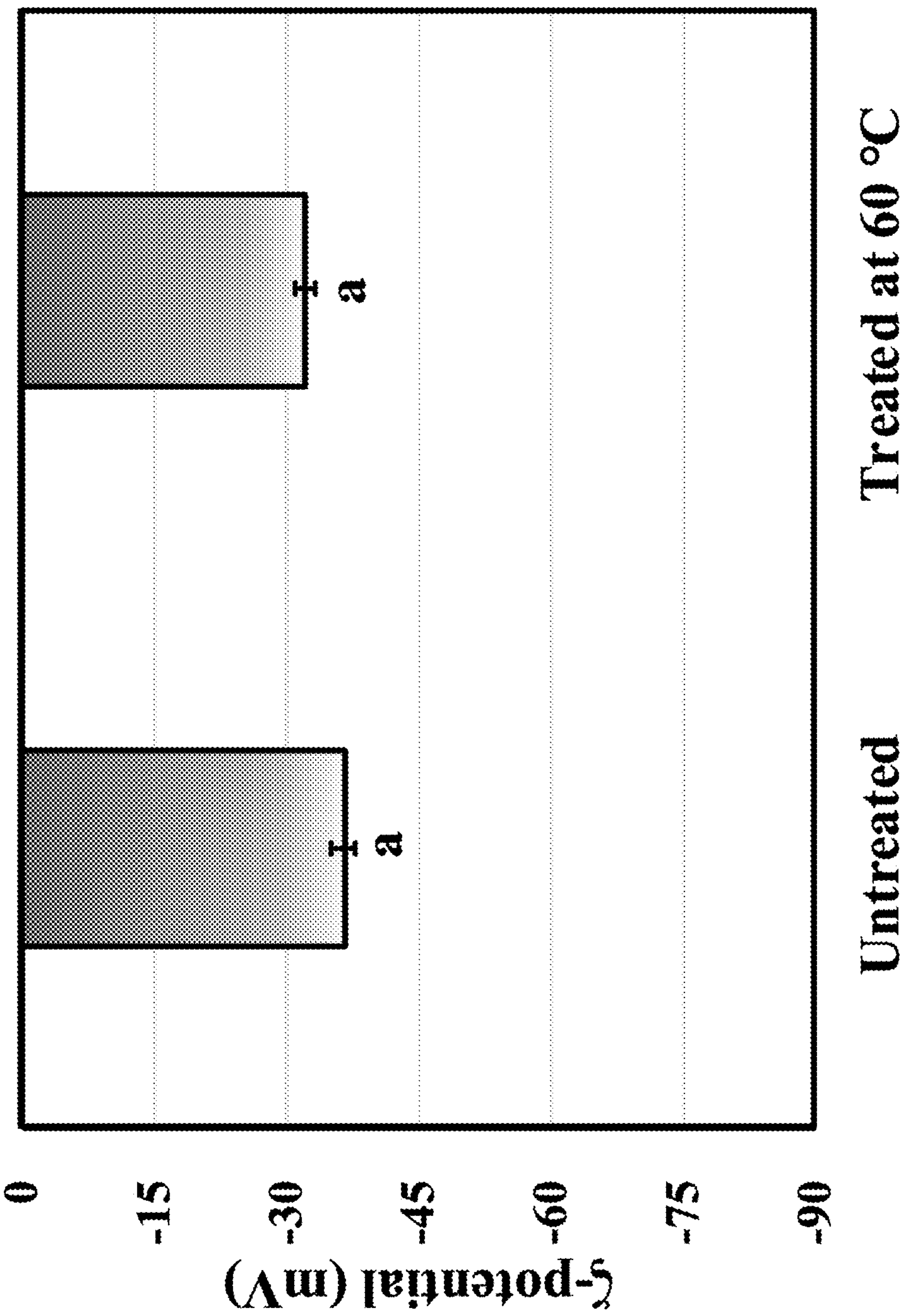
FIG. 9C(2)

Step (a)

Step (b)

LIPOSOMES AND METHODS OF MAKING THE SAME

CROSS REFERENCE TO RELATED APPLICATIONS

This application claims the benefit of U.S. Provisional Patent Application No. 63/220,352, filed Jul. 9, 2021, the contents of the above-identified application are hereby fully incorporated herein by reference in their entirety.

STATEMENT REGARDING FEDERALLY SPONSORED RESEARCH

This invention was made with government support under Grant No. 2016-09109 and Grant No. 2017-67017-26474 awarded by the United States Department of Agriculture National Institute of Food and Agriculture. The government has certain rights in the invention.

TECHNICAL FIELD

The subject matter disclosed herein is generally directed to liposomes and liposome synthesis.

BACKGROUND

In recent years, food industry has prioritized the use of functional food ingredients to design health-promoting food products. Traditionally, phospholipids, mostly sourced from soybean, have been incorporated into foods as emulsifiers due to their amphiphilic nature that contains both a hydrophilic head and a hydrophobic tail. Among phospholipids, milk fat globule membrane (MFGM) phospholipids have received much attention owing to their composition, stability, and potential health benefits. In particular, MFGM phospholipids are reported to have antiproliferative activity against human ovary and colon cancer cells, stimulate the development and outgrowth of cortical neurons, and inhibit the rotavirus infection in vitro. In addition, sphingomyelin (SM) present in the MFGM has been associated with several health benefits such as improving cell growth and regulation, suppressing Alzheimer's disease, and protecting against hypercholesterolemia and cancer. Previously, MFGM phospholipid concentrates (with ca. 60% to 70% phospholipid content) were developed, which had the highest phospholipid content reported. Yet, the source and processing steps of those concentrates are not known due to trade secret practices. However, the number of high-purity MFGM phospholipid concentrates are still scarce.

One source of MFGM phospholipids is buttermilk, a byproduct of the butter-making process. Buttermilk is the liquid fraction obtained after cream churning during butter-making process, which is abundant, and relatively inexpensive. Specifically, buttermilk powder contains a phospholipid content that is mainly composed of phosphatidylethanolamine, phosphatidylcholine, SM, phosphatidylinositol, and phosphatidylserine. In addition, the SM and PS contents of MFGM phospholipids are high compared to other major lecithin sources (soybean and egg yolk).

Considering the need and health benefits, significant efforts have been made to concentrate MFGM phospholipids from buttermilk powder. So far, two main approaches have been implemented to concentrate MFGM phospholipids. The first approach is based on extraction of both polar and nonpolar lipids from buttermilk powder (spray died buttermilk) using solvents such as chloroform, hexane, methanol, petroleum ether and N,N-dimethylcyclohexylamine. The other approach aims to increase the relative concentration of MFGM phospholipids by removing sugars, proteins and nonpolar lipids from buttermilk powder. However, the first approach extracts both polar and nonpolar lipids resulting in phospholipid extracts with low purity. The second approach separates nonpolar lipids but leaves MFGM phospholipids contaminated with proteins and carbohydrates in the buttermilk powder. Membrane filtration coupled with supercritical carbon dioxide (SC-$CO_2$) extraction has been investigated to increase the concentration of phospholipids in the buttermilk powder. Briefly, buttermilk was microfiltered or ultrafiltered, spray dried, and then subjected to SC-$CO_2$ extraction to remove the nonpolar lipids. However, the use of toxic organic solvents and low phospholipid concentrations in the products (less than 10% using the microfiltration coupled SC-$CO_2$ method) limit their food applications.

The use of SC-$CO_2$ has been considered as a green method for the extraction of lipids from various sources since $CO_2$ is a nontoxic, inexpensive, abundant, environmentally friendly, and has moderate critical temperature (31° C.) and pressure (7.4 MPa). But, while SC-$CO_2$ is a solvent to extract nonpolar lipids, it has very limited solvating power for polar lipids because of its nonpolar nature. The use of SC-$CO_2$ with ethanol as a cosolvent to extract polar lipids from buttermilk powder was reported, where buttermilk powder was subjected to enzymatic hydrolysis, ultrafiltration and finally ethanol-modified SC-$CO_2$ extraction. Phospholipids (56% purity) were extracted from spray-dried 50 kDa retentate which was produced by hydrolysis and 50 kDa membrane ultrafiltration of buttermilk. Nonetheless, the ethanol-modified SC-$CO_2$ extraction was investigated only at constant operating conditions (40° C. and 30 MPa) using a very long extraction time of 13 h.

Liposomes are artificial spherical vesicles consisting of one or more phospholipid bilayers enclosing an aqueous core. The aliphatic chains of the phospholipids promote internal hydrophobic interaction while the polar headgroups interact with the internal and external aqueous phases. The amphiphilic nature of liposomal systems allow them to entrap both hydrophobic and hydrophilic compounds, enabling the encapsulation of a diverse range of bioactives/drugs. Depending on the arrangement of phospholipid bilayer, liposomes can be classified into one of the three categories: (1) unilamellar vesicles (ULV), (2) multilamellar vesicles (MLV), and (3) multivesicular vesicles (MVV). Liposomal systems are also regarded for their biodegradability, biocompatibility, site-specificity, minimal-toxicity, and non-immunogenicity. Due to these advantages, liposomal systems have found applications in the food, pharmaceutical, and cosmetic industries as effective vehicles for bioactive delivery.

Existing techniques for liposome synthesis include thin film hydration (TFH), reverse phase evaporation, solvent injection, emulsion method, and detergent removal method. The major drawback of these techniques is the use of toxic organic solvents to dissolve the lipid phase, resulting in negative impacts to the environment in addition to adding additional processing steps to remove the solvent from the final product, which can make the formulation cytotoxic and make them unsuitable for approved biological applications. Consequently, in recent years, novel liposome production methods have been proposed to eliminate or reduce the use of organic solvents, reduce processing time, maintain reproducibility and homogeneity, and increase liposomal encapsulation efficiency. To avoid these drawbacks, supercritical fluid (SCF) based methods have emerged as alternatives for liposome synthesis. SCFs are non-condensable fluids that are highly dense at temperatures and pressures exceeding their critical point.

Traditionally, variations of phosphatidylcholine (PC) have been used for making liposomes. Due to their unsaturated fatty acid chains, PC has a low phase transition temperature ($T_m$). As such, liposomes made from PC will disintegrate upon heat treatment as they undergo a gel-to-liquid phase transformation. Therefore, liposomes made from phospholipids with a higher phase transition temperature are desirable because they would be able to undergo higher temperature treatment without having any structural disintegration. Several research works have been conducted in an effort to produce liposomes with improved heat stability. However, most of these methods involve the use of lysolipids or other synthetic temperature-sensitive polymers, which are often not cost effective and face challenges to get approval as food additives. Thus, there exists and ongoing and unmet need for techniques and methods for synthesizing liposomes, particularly those with desirable phospholipids that are heat stable.

SUMMARY

Described in certain example embodiments herein are methods for preparing a milk fat globule membrane (MFGM) phospholipid composition from a milk product, the method comprising: extracting a nonpolar lipid fraction of a milk product with supercritical carbon dioxide (SC-$CO_2$), with the proviso that, prior to the extracting the nonpolar lipid fraction, the milk product is not contacted with an enzyme, is not filtered, or any combination thereof; and extracting a polar lipid fraction of the milk product with a supercritical fluid comprising SC-$CO_2$ and one or more polar co-solvent(s), where the polar lipid fraction is the MFGM phospholipid composition.

In certain example embodiments, the milk product is chosen from buttermilk powder, whey protein phospholipid concentrate, and any combination thereof.

In certain example embodiments, the polar co-solvent(s) is/are chosen from ethanol, methanol, acetone, hexane, acetonitrile, and any combination thereof.

In certain example embodiments, the supercritical fluid comprises from about 5 weight percent (wt. %) to about 20 wt. % of the polar co-solvent(s), including all 0.1% values and ranges therebetween, based on the total weight of SC-$CO_2$ and the polar co-solvent(s).

In certain example embodiments, the extracting the nonpolar lipid fraction of the milk product with SC-$CO_2$ is performed at a temperature of about 50° C. to about 60° C., including all 0.1° C. values and ranges therebetween, and at a pressure of about 30 MPa to about 40 MPa including all 0.1 MPa values and ranges therebetween; and/or the extracting the polar lipid fraction of the milk product with the supercritical fluid is performed at a temperature of about 50° C. to about 60° C., including all 0.1° C. values and ranges therebetween, and at a pressure of about 30 MPa to about 40 MPa, including all 0.1° C. values and ranges therebetween.

In certain example embodiments, the extracting the nonpolar lipid fraction of the milk product with SC-$CO_2$ and the extracting the polar lipid fraction of the milk product with the supercritical fluid each comprises: extracting under static conditions for at least a portion of the time; and extracting under dynamic conditions for at least a portion of the time.

In certain example embodiments, after the extracting the polar lipid fraction of the milk product with the supercritical fluid, the method further comprises removing at least a portion of or all of the polar co-solvent(s), if present, from the MFGM phospholipid extract.

Described in certain example embodiments herein are methods for preparing one or more liposome(s) comprising: generating a pressurized mixture comprising supercritical carbon dioxide (SC-$CO_2$) and one or more milk fat globule membrane (MFGM) phospholipid composition(s), where the MFGM phospholipid composition(s), individually, comprise(s) dihydrosphingomyelin (DHSM), sphingomyelin (SM), phosphatidylethanolamine (PE), phosphatidylserine (PS), phosphatidylinositol (PI), and phosphatidylcholine (PC); releasing an at least partially or completely depressurized mixture stream from the pressurized mixture; and mixing the depressurized mixture stream and an aqueous stream, thereby forming the liposome(s).

In certain example embodiments, the MFGM phospholipid composition(s), individually, further comprise(s) one or more or all of the following: from about 80 wt. % to about 90 wt. %, including all 0.1% values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater.

In certain example embodiments, the pressurized mixture further comprises a lipophilic cargo comprising one or more polycyclic amphiphilic compounds(s), one or more hydrophobic compound(s), one or more amphiphilic compound (s), or any combination thereof, where the hydrophobic compound(s) is/are chosen from hydrophobic therapeutic agent(s), hydrophobic nutrient(s), hydrophobic bioactive agent(s), and any combination thereof, and where the amphiphilic compound(s) is/are chosen from amphiphilic therapeutic agent(s), amphiphilic nutrient(s), amphiphilic bioactive agent(s), and any combination thereof; and/or the aqueous stream further comprises an aqueous cargo comprising one or more hydrophobic compound(s), one or more of the amphiphilic compound(s), or any combination thereof, where the hydrophilic compound(s) is/are chosen from hydrophilic therapeutic agent(s), hydrophilic nutrient (s), hydrophilic bioactive agent(s), and any combination thereof, and where at least a portion of or all of the lipophilic cargo, at least a portion of or all of the aqueous cargo, or any combination thereof, if present, is disposed in the liposome (s).

In certain example embodiments, from about 85% to about 95% of the polycyclic amphiphilic compound(s), the hydrophobic compound(s), the amphiphilic compound(s), or any combination thereof, of the lipophilic cargo is/are disposed in the liposome(s); and/or from about 60% to about 70% of the hydrophobic compound(s), the amphiphilic compound(s), or any combination thereof, of the aqueous cargo is/are disposed in the liposome(s).

In certain example embodiments, the pressurized mixture is generated at: a pressure of about 10 MPa to about 40 MPa, including all 0.1 MPa values and ranges therebetween and/or a temperature of about 20° C. to about 60° C. including all 0.1° C. values and ranges therebetween.

In certain example embodiments, a method further comprises forming an aqueous dispersion of the liposome(s).

In certain example embodiments, a method further comprises coating at least a portion of or all of an exterior surface or surfaces of one or more or all of the liposome(s) with one or more enteric material(s).

Described in certain example embodiments herein are milk fat globule membrane (MFGM) phospholipid compositions comprising dihydrosphingomyelin (DHSM), sphingomyelin (SM), phosphatidylethanolamine (PE), phosphatidylserine (PS), phosphatidylinositol (PI), and phosphatidylcholine (PC), and one or more or all of the following: from about 80 wt. % to about 90 wt. %, including all 0.1% values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater.

In certain example embodiments, the MFGM phospholipid composition is a food composition, a pharmaceutical composition, or a cosmetic composition.

Described in certain example embodiments herein are liposome compositions comprising one or more liposome(s), each, independently, comprising a phospholipid bilayer enclosing an aqueous core, where the phospholipid bilayer comprises dihydrosphingomyelin (DHSM), sphingomyelin (SM), phosphatidylethanolamine (PE), phosphatidylserine (PS), phosphatidylinositol (PI), and phosphatidylcholine (PC) and one or more or all of the following: from about 80 wt. % to about 90 wt. %, including all 0.1% values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater.

In certain example embodiments, the phospholipid bilayer comprises one or more polycyclic amphiphilic compound (s), one or more hydrophobic compound(s), one or more amphiphilic compound(s), or any combination thereof, where the hydrophobic compound(s) is/are chosen from hydrophobic therapeutic agent(s), hydrophobic nutrient(s), hydrophobic bioactive agent(s), and any combination thereof, and where the amphiphilic compound(s) is/are chosen from amphiphilic therapeutic agent(s), amphiphilic nutrient(s), amphiphilic bioactive agent(s), and any combination thereof; and/or the aqueous core comprises one or more hydrophobic compound(s), one or more of the amphiphilic compound(s), or any combination thereof, where the hydrophilic compound(s) chosen from hydrophilic therapeutic agent(s), hydrophilic nutrient(s), hydrophilic bioactive agent(s), and any combination thereof.

In certain example embodiments, the liposome composition is an aqueous dispersion.

In certain example embodiments, the liposome composition further comprises one or more enteric material(s) disposed on at least a portion of or all of an exterior surface or surfaces of one or more or all of the liposome(s).

In certain example embodiments, the one or more enteric material(s) is/are chosen from pH sensitive polymeric material(s), carbohydrate(s), protein(s), and any combination thereof.

In certain example embodiments, the liposome(s) comprise(s) a linear dimension of from 500 nm to about 700 nm, including all 0.1 nm values and ranges therebetween.

In certain example embodiments, the liposome(s) exhibit (s) a negative zeta potential of from about 55 mV to about 60 mV, including all 0.1 mV values and ranges therebetween.

In certain example embodiments, the liposome(s) is/are stable under one or more or all of the following conditions: at a temperature of about 60° C. to about 90° C., including all 0.1% values and ranges therebetween, for a time of about 30 minutes; at a pH of about 4.5 or lower for a time of about 120 minutes.

In certain example embodiments, the liposome composition is a food composition, a pharmaceutical composition, a cosmetic composition, or any combination thereof.

Described in certain example embodiments herein are methods for delivering a therapeutic agent, a nutrient, a bioactive agent, or any combination thereof, to a subject, the method comprising administering one or more liposome composition(s) of the present disclosure to the subject.

In certain example embodiments, the administering the liposome composition(s) to the subject is oral administration.

Described in certain example embodiments herein are methods for preparing a milk fat globule membrane (MFGM) phospholipid extract, the method comprising extracting a polar lipid fraction of a milk product with supercritical carbon dioxide.

In certain example embodiments, the milk product is buttermilk powder.

In certain example embodiments, the milk product is heated to from about 25 degrees C. to 90 degrees C.

In certain example embodiments, the milk product is heated to 60 degrees C.

In certain example embodiments, the milk product is pressurized from 10-100 MPa.

In certain example embodiments, the milk product is pressurized at 40 MPa.

In certain example embodiments, a first nonpolar fraction is extracted from the milk product.

In certain example embodiments, MFGM phospholipid composition comprises a second polar fraction extracted from the milk product.

Described in certain example embodiments herein are methods for preparing a heat stable liposome comprising: preparing lipophilic cargo comprising a milk fat globule membrane (MFGM) phospholipid extract; preparing an aqueous cargo; generating a pressurized mixture comprising supercritical carbon dioxide and the lipophilic cargo; releasing the pressurized mixture through an eductor-nozzle assembly while introducing a stream of the aqueous cargo into the eductor-nozzle assemble; and collecting liposomes.

In certain example embodiments, the MFGM phospholipid composition is prepared as described in any one of the preceding paragraphs or as described elsewhere herein.

In certain example embodiments, the lipophilic cargo comprises a hydrophobic nutrient and/or vitamin.

In certain example embodiments, the lipophilic cargo comprises vitamin E.

In certain example embodiments, the lipophilic cargo further comprises cholesterol.

In certain example embodiments, the lipophilic cargo comprises MFGM phospholipid extract, cholesterol, and vitamin E in a weight ratio of 5:1:1.

In certain example embodiments, the aqueous cargo comprises one or more hydrophilic nutrients and/or vitamins.

In certain example embodiments, the aqueous cargo comprises vitamin E.

In certain example embodiments, the liposome is heat stable for at least 30 minutes at 60 degrees C., 75 degrees C., or 90 degrees C.

In certain example embodiments, the MFGM phospholipid composition comprises one or more of dihydrosphingomyelin (DHSM), sphingomyelin (SM), phosphatidylethanolamine (PE), phosphatidylserine (PS), phosphatidylinositol (PI), and phosphatidylcholine (PC).

Described in certain example embodiments herein are heat stable liposome comprising a liposome made by any one of the methods of any one of the preceding paragraphs or as described elsewhere herein.

In certain example embodiments, the heat stable liposome further comprises one or more cargos.

In certain example embodiments, the cargo is a therapeutic agent, nutrient/vitamin, bioactive agent, or a combination thereof.

In certain example embodiments, the cargo is lipophilic. In certain example embodiments, the cargo is hydrophilic.

These and other aspects, features, and advantages of the example embodiments will become apparent to those having ordinary skill in the art upon consideration of the following detailed description of example embodiments.

BRIEF DESCRIPTION OF THE FIGURES

For a fuller understanding of the nature and objects of the disclosure, reference should be made to the following detailed description taken in conjunction with the accompanying figures herein.

FIG. 6C shows: lipid nucleation and atomization of aqueous phase (right), liposomal membrane self-assembly (center), and multivitamin loaded liposome formation (left). Abbreviations: T: temperature sensor, P: pressure sensor, SV: solenoid valve, M: metering valve, S: safety valve, HPP: high-pressure pump, BPR: back-pressure regulator; VE: venturi eductor.

FIGS. 9A(1)-9C(2) show average diameters of (FIG. 9A(1)) MFGM and (FIG. 9A(2)) sunflower phosphatidylcholine (SFPC) liposomes; diameter distributions of (FIG. 9B(1)) MFGM and (FIG. 9(2)) SFPC liposomes; and zeta (ζ)-potentials of (FIG. 9C(1)) MFGM and (FIG. 9C(2)) SFPC liposomes, before and after heat-treatment for 30 minutes. Alphabetical labels indicate statistically significant differences between treatments ($p<0.05$).

(FIG. 20B) the Sahlin Peppas Equation; or (FIG. 20C) the Hixon Crowell Equation. The fitness of the model has been represented by the absolute relative deviation (ARD) value and a lower ARD value represents better fit. Vitamin C: Filled Circle=data; Solid Line=Fitted Model. Vitamin E: Open Circle=data; Dashed Line=Fitted Model.

Figure 1:
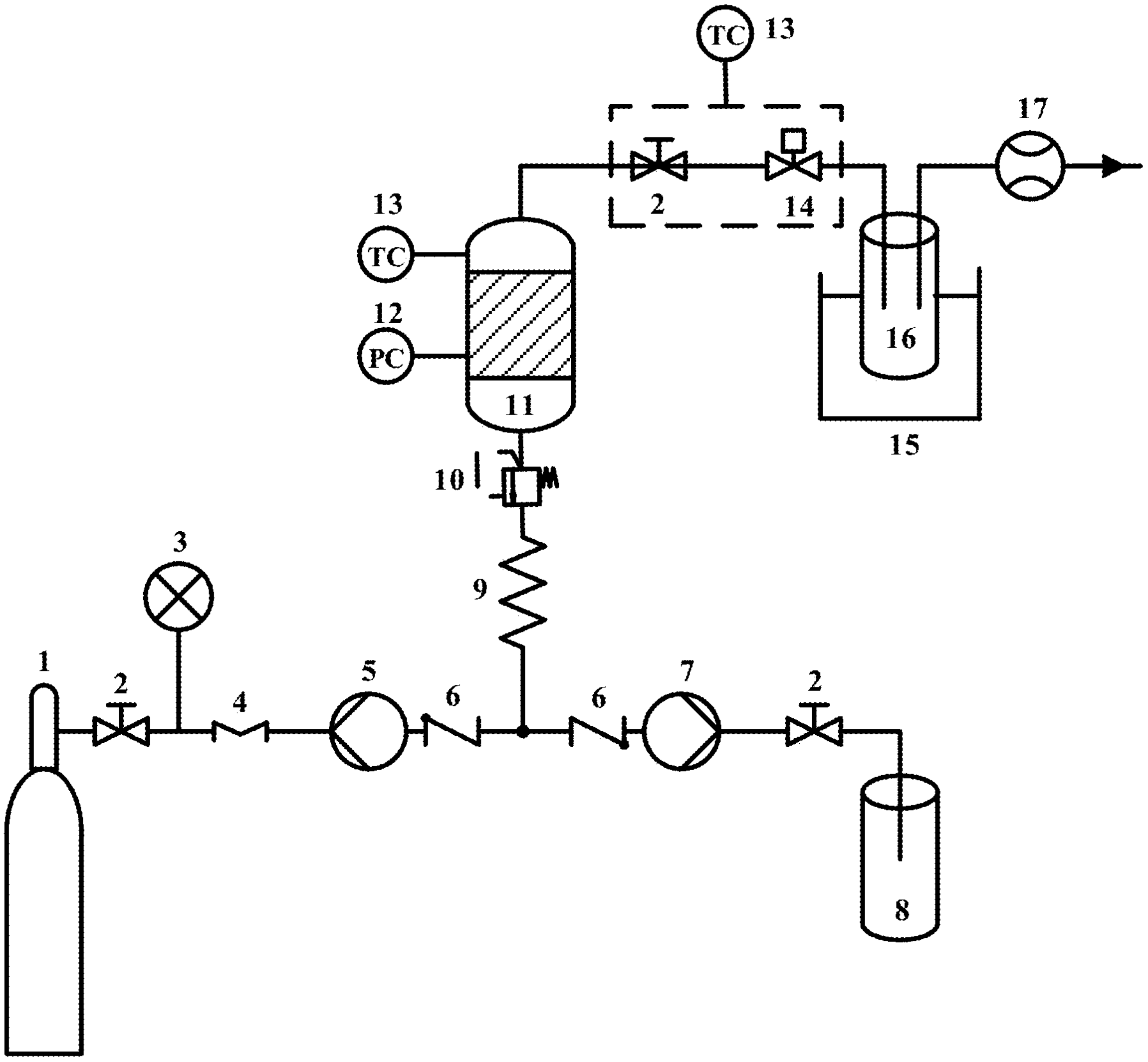
FIG. 1 shows a schematic diagram of an ethanol-modified supercritical carbon dioxide (SC-$CO_2$) extraction system. Tags: (1) $CO_2$ cylinder; (2) needle valve; (3) pressure gauge; (4) pre-chiller; (5) high pressure pump for $CO_2$; (6) check valve; (7) high pressure pump for cosolvent; (8) cosolvent; (9) preheater; (10) rupture disc; (11) high pressure vessel; (12) pressure controller; (13) temperature controller; (14) micrometering valve; (15) cold trap; (16) sample vial; (17) flow meter.

The figures herein are for illustrative purposes only and are not necessarily drawn to scale.

DETAILED DESCRIPTION OF THE DISCLOSURE

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further aspect includes from the one particular value and/or to the other particular value. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the present disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, a "biological sample" may contain whole cells and/or live cells and/or cell debris. The biological sample may contain (or be derived from) a "bodily fluid". The present disclosure encompasses embodiments where the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject" and "patient" are used interchangeably herein to refer to a vertebrate, preferably a mammal, more preferably a human, or the like. Mammals include, but are not limited to, murines, simians, humans, farm animals, sport animals, pets, and the like. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the present disclosure. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

As used herein, unless otherwise stated, the term "group" refers to a chemical entity that is monovalent (i.e., has one terminus that can be covalently bonded to other chemical species), divalent, or polyvalent (i.e., has two or more termini that can be covalently bonded to other chemical species). The term "group" also includes radicals (e.g., monovalent and multivalent, such as, for example, divalent, trivalent, and the like, radicals). Illustrative examples of groups include:

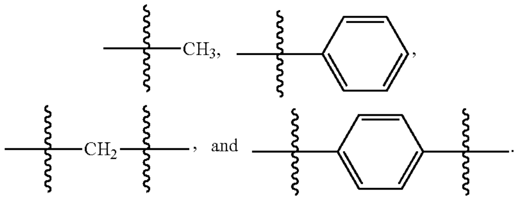

The instant methods can be performed under various method conditions. A method can comprise one or more steps and each step can be performed under the same or different method conditions as other steps.

A method can be carried out at various pressures. In various examples, a method is carried out at atmospheric pressure (e.g., 1 standard atmosphere (atm) at sea level or the like), at greater than atmospheric pressure (e.g. heating in a sealed pressurized method vessel or the like), at below atmospheric pressure (e.g., under vacuum (e.g., from about 1 mTorr or less to about 100 mTorr or less, including all 0.1 mTorr values and ranges therebetween) (e.g., about 100 mTorr or less, about 50 mTorr or less, about 10 mTorr or less, or about 1 mTorr or less) and the like), or any combination thereof (e.g., where each step is performed at a different pressure as other steps).

A method can be carried out at various temperatures. In various examples, a method is carried out at room temperature (e.g., from about 20° C. to about 22° C., including all 0.1° C. values and ranges therebetween), below room temperature (e.g., below about 20° C., such as for example, from about 0° C. to below about 20° C., including all 0.1° C. values and ranges therebetween) (e.g., from about 0° C. to about 20° C., from about 0° C. to about 10° C., about 5° C. from about 20° C. to, about 5° C. to about 10, or 10° C. to below about 20° C.), above room temperature (e.g., at a temperature up to or about a boiling point of the solvent(s), if present) (e.g., from above about 22° C. to about 100° C., including all 0.1° C. values and ranges therebetween) (e.g., from about 25° C. to about 100° C., from about 30° C. to about 90° C., from about 35° C. to about 80° C., or from about 40° C. to about 60° C.), or any combination thereof (e.g., where each step is performed at a different temperature as other steps). In various examples, the pressure and temperature of the method are each at or above the critical pressure and critical temperature, respectively, of a method solvent (e.g., the critical temperature is 31.06° C., and its critical pressure is 7.39 MPa for forming supercritical $CO_2$).

A method can be carried out for various times. The method time can depend on factors such as, for example, temperature, pressure, presence and/or efficiency of a catalyst, presence and/or intensity of an applied energy source, mixing (e.g., stirring, or the like), or the like, or a combination thereof. In various examples, method times range from about seconds (e.g., two seconds) to greater than about 200 hours, including all integer second values and ranges therebetween (e.g., from about 1 minute to about 150 hours, including all integer second values and ranges therebetween) (e.g., about 10 minutes, about 1 hour, about 12 hours, about 24 hours, about 120 hours, or about 150 hours), or any combination thereof (e.g., where each step is performed at a different time as other steps).

In an aspect, the present disclosure provides methods for preparing milk fat globule membrane (MFGM) phospholipid compositions from a milk product or the like. Non-limiting examples of methods for preparing MFGM phospholipid compositions are provided herein. In various examples, methods of preparing MFGM phospholipid compositions are used to prepare MFGM phospholipid compositions and/or liposome compositions of the present disclosure.

In various examples, a method for preparing a MFGM phospholipid composition from a milk product comprises extracting a polar lipid fraction of a milk product with a supercritical fluid comprising SC-$CO_2$ and one or more polar co-solvent(s), where the polar lipid fraction is the MFGM phospholipid composition (e.g., a one-stage polar co-solvent modified SC-$CO_2$ extraction method). In various examples, prior to the extracting the polar lipid fraction from the milk product, the method further comprises extracting a nonpolar lipid fraction of the milk product with supercritical carbon dioxide (SC-$CO_2$) (e.g., a sequential two-stage extraction) (e.g., where a polar lipid fraction is extracted from a previously SC-$CO_2$ extracted milk product from which a nonpolar lipid fraction has been removed). In various examples, prior to the extracting the nonpolar lipid fraction, the extracting the polar lipid fraction, or both, the milk product is not contacted with an enzyme (e.g., not subject to enzymatic hydrolysis or the like), is not filtered (e.g., filtered by membrane filtration, ultrafiltration, or the like), is not contacted with an organic solvent (e.g., a toxic organic solvent or the like), or the like, or any combination thereof. In various examples, a toxic organic solvent is not a generally recognized as safe (GRAS) solvent.

A method for preparing a MFGM phospholipid composition from a milk product can use various milk products and various reagents to extract various lipid fractions from the milk products. In various examples, a milk product is a buttermilk product, a whey product, or the like, or any combination thereof. In various examples, a milk product is chosen from buttermilk powder (e.g., spray-dried buttermilk powder), whey protein phospholipid concentrate, and the like, and any combination thereof.

A method for preparing a MFGM phospholipid composition from a milk product can use various polar co-solvent (s). In various examples, the polar co-solvent(s) is/are chosen from organic solvents (such as, for example, alcohols, ethers, ketones, hydrocarbons, and the like, and any combination thereof) and the like. In various examples, the polar co-solvent(s) is/are chosen from ethanol, methanol, acetone, hexane, acetonitrile, and the like, and any combination thereof. In various examples, the polar co-solvents is/are not chosen from methanol, chlorinated solvents (such as, for example, chloroform and the like), petroleum ethers, N,N-dimethylcyclohexylamine, and the like, and any combination thereof, any one or more of which may be a toxic solvent or toxic solvents. In various examples, the polar co-solvent(s) is/are nontoxic, environmentally friendly, food-grade, GRAS, or the like, or any combination thereof. In various examples, the polar co-solvent(s) is/are GRAS solvent(s). A method for preparing a MFGM phospholipid composition from a milk product can use various supercritical fluid compositions. In various examples, the supercritical fluid comprises from about 5 weight percent (wt. %) to about 30 wt. % of the polar co-solvent(s), including all 0.1 wt. % values and ranges therebetween (e.g., from about 5 wt. % to about 20 wt. %, from about 10 wt. % to about 30 wt. %, from about 20 wt. % to about 20 wt. %, or from about 20 wt. % to about 30 wt. %), based on the total weight of SC-$CO_2$ and the polar co-solvent(s).

A method for preparing a MFGM phospholipid composition from a milk product can extract the nonpolar lipid fraction of the milk product with SC-$CO_2$ under various method conditions. In various examples, the extracting the nonpolar lipid fraction of the milk product with SC-$CO_2$ is performed at or above the critical pressure and critical temperature, respectively, of $CO_2$ (e.g., 31.06° C., and 7.39 MPa). In various examples, extracting the nonpolar lipid fraction of the milk product with SC-$CO_2$ is performed at a temperature of from about 25° C. to 90° C., including all 0.1° C. values and ranges therebetween (e.g., about 25° C. to about 80° C., about 30° C. to about 80° C., about 40° C. to about 80° C., about 50° C. to about 00° C., about 60° C. to about 80° C., about 25° C. to about 60° C., about 30° C. to about 60° C., about 40° C. to about 60° C., or about 50° C. to about 60° C.). In various examples, extracting the nonpolar lipid fraction of the milk product with SC-$CO_2$ is performed at a pressure of from about 10 MPa to about 100 MPa, including all 0.1 MPa values and ranges therebetween (e.g., from about 15 MPa, to about 100 MPa, from about 20 MPa to about 100 MPa, from about 25 MPa to about 100 MPa, from about 30 MPa to about 100 MPa, from about 40 MPa to about 100 MPa, from about 30 MPa to about 60 MPa, or from about 30 MPa to about 40 MPa). In various examples, extracting the nonpolar lipid fraction of the milk product was performed at a temperature of no more than 60° C., and at least a pressure of 40 MPa, In various examples, the extracting the nonpolar lipid fraction of the milk product with SC-$CO_2$ comprises extracting under static conditions for at least a portion of the time and extracting under dynamic conditions for at least a portion of the time.

A method for preparing a MFGM phospholipid composition from a milk product can extract the polar lipid fraction of the milk product with the supercritical fluid under various method conditions. In various examples, the extracting the polar lipid fraction of the milk product with the supercritical fluid is performed at or above the critical pressure and critical temperature, respectively, of $CO_2$ (e.g., 31.06° C., and 7.39 MPa). In various examples, the extracting the polar lipid fraction of the milk product with the supercritical fluid is performed at a temperature of about 50° to about 60° C., including all 0.1° C. values and ranges therebetween, and/or at a pressure of about 30 MPa to about 40 MPa, including all 0.1 MPa values and ranges therebetween. In various examples, extracting the polar lipid fraction of the milk product was performed at a temperature of no more than 60° C., at least a pressure of 30 MPa, and using a supercritical fluid comprising at least about 15 wt. % ethanol, based on the total weight of the ethanol and $CO_2$. In various examples, the extracting the polar lipid fraction of the milk product with the supercritical fluid comprises extracting under static conditions for at least a portion of the time; and extracting under dynamic conditions for at least a portion of the time.

In various examples, after the extracting the polar lipid fraction of the milk product with the supercritical fluid, a method for preparing a MFGM phospholipid composition from a milk product further comprises removing at least a portion of or all of the polar co-solvent(s), if present, from the MFGM phospholipid extract. Methods of removing solvent from method mixtures are known in the art. In various examples, the polar co-solvent(s) is/are removed from the method mixture by evaporation, such as, for example, under vacuum, and the like.

In various examples, a method for preparing a MFGM phospholipid composition from a milk product produces a MFGM phospholipid composition comprising from about 40 wt. % to about 85 wt. %, including all 0.1 wt. % values and ranges therebetween, of phospholipids, based on the total weight of lipids (e.g., from about 45 wt. % to about 55 wt. %, about 70 wt. % to about 85 wt. %, about 72 wt. % to about 85 wt. %, about 72 wt. % to about 80 wt. %, or about 72 wt. % to about 76 wt. %). In various examples, a MFGM phospholipid composition comprises one or more or all of the following phospholipids: dihydrosphingomyelin (DHSM), sphingomyelin (SM), phosphatidylethanolamine (PE), phosphatidylserine (PS), phosphatidylinositol (PI), and phosphatidylcholine (PC). In various examples, a method produces a MFGM phospholipid composition comprising one or more or all of the following: from about 80 wt. % to about 90 wt. %, including all 0.1 wt. % values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater. In various examples, a method produces a MFGM phospholipid composition which is substantially or completely solvent free. In various examples, a method produced a MFGM phospholipid composition which is substantially or completely free of sugars, proteins, nonpolar lipids, or the like, or any combination thereof.

In an aspect, the present disclosure provides methods for preparing one or more liposome(s). Non-limiting examples of methods for preparing liposome(s) are provided herein. In various examples, methods of preparing liposome(s) of the present disclosure are used to prepare liposome compositions of the present disclosure. In various examples, methods for preparing liposome(s) are used to prepare liposome compositions of the present disclosure.

In various examples, a method for preparing liposome(s) comprises generating a pressurized mixture comprising supercritical carbon dioxide ($SC-CO_2$) and one or more milk fat globule membrane (MFGM) phospholipid composition (s); releasing an at least partially or completely depressurized mixture stream from the pressurized mixture; and mixing the depressurized mixture stream and an aqueous stream, thereby forming the liposome(s).

A method for preparing liposome(s) can be performed using various systems. In various examples, a method for preparing liposome(s) is conducted in a venturi-based system (Vent-RESS) for vacuum driven cargo loading as described herein, the Vent-RESS system comprising an eductor-nozzle assembly. In various examples, the releasing an at least partially or completely depressurized mixture stream from the pressurized mixture comprises releasing the pressurized mixture through the eductor-nozzle assembly. In various examples, the releasing the pressurized mixture through the eductor-nozzle assembly creates a vacuum at an opening in the eductor-nozzle assembly. In various examples, the mixing the depressurized mixture stream and the aqueous stream comprises vacuum driven cargo loading the aqueous stream through the opening into the eductor-nozzle assembly, where the mixing of the depressurized mixture stream and the aqueous stream occurs.

A pressurized mixture can comprise various MFGM phospholipid compositions. In various examples, a lipophilic cargo comprises one or more MFGM phospholipid composition(s) of the present disclosure and/or prepared by a method of the present disclosure. In various examples, the MFGM phospholipid composition(s), independently, comprise(s) from about 40 wt. % to about 85 wt. %, including all 0.1 wt. % values and ranges therebetween, of phospholipids, based on the total weight of lipids (e.g., from about 45 wt. % to about 55 wt. %, about 70 wt. % to about 85 wt. %, about 72 wt. % to about 85 wt. %, about 72 wt. % to about 80 wt. %, or about 72 wt. % to about 76 wt. %). In various examples, the MFGM phospholipid composition(s), individually, comprise(s) one or more or all of the following phospholipids: dihydrosphingomyelin (DHSM), sphingomyelin (SM), phosphatidylethanolamine (PE), phosphatidylserine (PS), phosphatidylinositol (PI), and phosphatidylcholine (PC). In various examples, the MFGM phospholipid composition(s), individually, comprise(s) one or more or all of the following: from about 80 wt. % to about 90 wt. %, including all 0.1 wt. % values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater. In various examples, the MFGM phospholipid composition(s), individually, is/are substantially or completely solvent free. In various examples, the MFGM phospholipid composition(s), individually, is/are substantially or completely free of sugars, proteins, nonpolar lipids, or the like, or any combination thereof.

A pressurized mixture can comprise various additional components. In various examples, a pressurized mixture further comprises a lipophilic cargo. In various examples, an aqueous stream comprises various components. In various example, an aqueous stream comprises an aqueous cargo. In various examples, at least a portion of or all of the lipophilic cargo, at least a portion of or all of the aqueous cargo, or the like, or any combination thereof, if present, are disposed (e.g., encapsulated or the like) in the liposome(s). In various examples, at least a portion of or all of the lipophilic cargo is disposed (e.g., encapsulated or the like) in the phospholipid bilayer. In various examples, at least a portion or all of the aqueous cargo is disposed (e.g., encapsulated or the like) in the aqueous core.

In various examples, a lipophilic cargo comprises one or more polycyclic amphiphilic compound(s), one or more hydrophilic compound(s), one or more amphiphilic compound(s), or the like, or any combination thereof. In various examples, at least a portion of or all of the hydrophobic compound(s), at least a portion of or all of the amphiphilic compound(s), or any combination thereof, of the lipophilic cargo, and/or at least a portion of or all of the hydrophilic compound(s) of the aqueous cargo is/are chosen from therapeutic agent(s), nutrient(s), bioactive agent(s), and the like, and any combination thereof.

In various examples, the polycyclic amphiphilic compound(s) is/are chosen from cholesterol, phytosterols, tocosterols, and the like, and any combination thereof. In various examples, the hydrophobic compound(s) is/are chosen from fat-soluble vitamins (e.g., vitamin A, vitamin D, vitamin E, and the like, and any combination thereof), and the like, and any combination thereof. In various examples, the amphiphilic compound(s) is/are chosen from the polycyclic amphiphilic compound(s) and the like. In various examples, the lipophilic cargo comprises a weight ratio of MFGM phospholipid extract(s): polycyclic amphiphilic compound (s) of about 5:1 or the like. In various examples, the lipophilic cargo comprises a weight ratio of MFGM phospholipid extract(s): polycyclic amphiphilic compound(s): hydrophobic and/or amphiphilic compound(s) of about 5:1:1 or the like.

In various examples, the aqueous cargo comprises one or more hydrophilic compound(s), one or more of the amphiphilic compound(s) (e.g., the polycyclic amphiphilic compound(s) or the like), or the like, or any combination thereof. In various examples, the hydrophilic compound(s) of the aqueous cargo is/are chosen from water soluble vitamins (e.g., vitamin C or the like), minerals, and the like, and any combination thereof.

In various examples, from about 85% to about 95% of the polycyclic amphiphilic compound(s), the hydrophobic compound(s), the amphiphilic compound(s), or any combination thereof, of the lipophilic cargo is/are disposed in the liposome(s). In various examples, from about 60% to about 70% of the hydrophobic compound(s), the amphiphilic compound(s), or any combination thereof, of the aqueous cargo is/are disposed in the liposome(s).

A method for preparing liposome(s) can be performed under various method conditions. In various examples, the pressurized mixture is generated at a pressure of from about 1 MPa to about 50 MPa, including all 0.1 MPa values and ranges therebetween (e.g., from about MPa to about 40 MPa, from about 5 MPa to about 50 MPa, from about 10 MPa to about 40 MPa, from about 10 MPa to about 30 MPa, or from about 10 MPa to about 20 MPa). In various examples, the pressurized mixture is generated at a temperature of from about 0° C. to about 80° C., including all 0.1° C. values and ranges therebetween (e.g., about 10° C. to about 80° C., about 20° C. to about 80° C., about 30° C. to about 80° C., about 10° C. to about 60° C., about 20° C. to about 60° C., about 30° C. to about 60° C., about 10° C. to about 40° C., about 20° C. to about 40° C., or about 30° C. to about 40° C.). In various examples, the pressurized mixture is generated at a pressure of about 10 MPa to about 40 MPa and/or a temperature of about 20° C. to about 60° C.

A method for preparing liposome(s) can comprise various additional steps. In various examples, a method further comprises forming an aqueous dispersion of the liposome (s). In various examples, a method further comprises removing unencapsulated hydrophobic compound(s), amphiphilic compound(s), or the like, or any combination thereof, of the lipophilic cargo, hydrophilic compound(s), amphiphilic compound(s), or the like, or any combination thereof, of the aqueous cargo, or the like, or any combination thereof, if present, from the liposome(s). In various examples, a method further comprises coating at least a portion of or all of an exterior surface or surfaces of one or more or all of the liposome(s) with one or more enteric material(s). In various examples, a method further comprises any combination of these steps.

In an aspect, the present disclosure provides MFGM phospholipid compositions. Non-limiting examples of MFGM phospholipid compositions are provided herein. In various examples, MFGM phospholipid compositions are prepared by methods of preparing MFGM phospholipid compositions of the present disclosure.

In various examples, a MFGM phospholipid composition comprises from about 40 wt. % to about 85 wt. %, including all 0.1 wt. % values and ranges therebetween, of phospholipids, based on the total weight of lipids (e.g., from about 45 wt. % to about 55 wt. %, about 70 wt. % to about 85 wt. %, about 72 wt. % to about 85 wt. %, about 72 wt. % to about 80 wt. %, or about 72 wt. % to about 76 wt. %). In various examples, a MFGM phospholipid composition comprises one or more or all of the following phospholipids: dihydrosphingomyelin (DHSM), sphingomyelin (SM), phosphatidylethanolamine (PE), phosphatidylserine (PS), phosphatidylinositol (PI), and phosphatidylcholine (PC). In various examples, a MFGM phospholipid composition comprises one or more or all of the following: from about 80 wt. % to about 90 wt. %, including all 0.1 wt. % values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater. In various examples, a MFGM phospholipid composition is substantially or completely solvent free. In various examples, a MFGM phospholipid composition is substantially or completely free of sugars, proteins, nonpolar lipids, or the like, or any combination thereof.

A MFGM phospholipid composition can have various uses. In various examples, a MFGM phospholipid composition is a food composition, a pharmaceutical composition, a cosmetic composition, or the like, or any combination thereof.

In an aspect, the present disclosure provides liposome compositions. Non-limiting examples of liposome compositions are presented herein. In various examples, liposome compositions of the present disclosure are prepared by methods of the present disclosure.

In various examples, a liposome composition comprises one or more liposome(s), each liposome, independently, comprising a phospholipid bilayer enclosing an aqueous core. In various examples, the liposome(s) comprise (or is/are) unilamellar vesicles (ULVs), multilamellar vesicles (MLVs), multivesicular vesicles (MVVs), or the like, or any combination thereof.

In various examples, a phospholipid bilayer comprises one or more MFGM phospholipid composition(s), such as, for example, of the present disclosure and/or prepared by methods of the present disclosure. In various examples, the MFGM phospholipid composition(s), independently, comprise(s) from about 40 wt. % to about 85 wt. %, including all 0.1 wt. % values and ranges therebetween, of phospholipids, based on the total weight of lipids (e.g., from about 45 wt. % to about 55 wt. %, about 70 wt. % to about 85 wt. %, about 72 wt. % to about 85 wt. %, about 72 wt. % to about 80 wt. %, or about 72 wt. % to about 76 wt. %). In various examples, the MFGM phospholipid extract(s), individually, comprise(s) one or more or all of the following phospholipids: dihydrosphingomyelin (DHSM), sphingomyelin (SM), phosphatidylethanolamine (PE), phosphatidylserine (PS), phosphatidylinositol (PI), and phosphatidylcholine (PC). In various examples, the MFGM phospholipid extract(s), individually, comprise(s) one or more or all of the following: from about 80 wt. % to about 90 wt. %, including all 0.1 wt. % values and ranges therebetween, of SM, PE, and PC; a weight ratio of PC to SM of about 1.6/1 or greater; a weight ratio of PC to PE of about 2.0/1 or greater; or a weight ratio of SM to PE of about 1.2/1 or greater. In various examples, the MFGM phospholipid composition(s), individually, is/are substantially or completely solvent free. In various examples, the MFGM phospholipid composition(s), individually, is/are substantially or completely free of sugars, proteins, nonpolar lipids, or the like, or any combination thereof.

A phospholipid bilayer can further comprise various compound(s). In various examples, a phospholipid bilayer comprises one or more polycyclic amphiphilic compound(s), one or more hydrophobic compound(s), one or more amphiphilic compound(s), or the like, or any combination thereof, such as, for example, of the present disclosure.

An aqueous core can comprise various compounds. In various examples, an aqueous core comprises one or more hydrophilic compound(s), one or more of the amphiphilic compound(s) (e.g., the polycyclic amphiphilic compound(s) or the like), or the like, or any combination thereof, such as, for example, of the present disclosure.

A liposome composition can comprise various forms. In various examples, the liposome(s) are dispersed in the aqueous phase (e.g., the liposome(s) is/are in the form of an aqueous dispersion).

A liposome composition can comprise various additional components. In various examples, a liposome composition does not comprise a lysolipid, a temperature sensitive polymer, or the like, or any combination thereof. In various examples, a liposome composition further comprises one or more enteric material(s). In various examples, enteric material(s) is/are disposed on at least a portion of or all of an exterior surface or surfaces of one or more or all of the liposome(s). In various examples, the enteric material(s) is/are disposed on the surface(s) of the liposome(s) by a modified solvent displacement method as disclosed herein. In various examples, the one or more enteric material(s) is/are chosen from pH sensitive material(s), synthetic polymeric material(s), carbohydrate material(s), protein material(s), and the like, and any combination thereof. In various examples, the enteric material(s) is/are pH sensitive polymeric material(s).

A liposome composition or the liposome(s) thereof can have various properties. Properties can be measured by methods known in the art. In various examples, particle size (e.g., a longest linear dimension, such as, for example, diameter, or the like), particle size distribution (e.g., mean, median, mode, distribution width of a longest linear dimension, e.g., a diameter, or the like), or the like, of the liposome(s) are determined (e.g., measured) by chromatography (e.g., gel permeation chromatography or the like), spectroscopy (e.g., dynamic light scattering (DLS), fluorescence correlation spectroscopy (FCS), or the like), electron microscopy (e.g., transmission electron microscopy (TEM), scanning electron microscopy (SEM), or the like) or the like. DLS contains systematic deviation and, therefore, the DLS size distribution may not correlate with the particle size distribution determined by TEM or GPC.

In various examples, zeta (ζ)-potential or the like of the liposome(s) is determined (e.g., measured) by doppler velocimetry (electrophoretic light scattering or ELS) or the like. In various examples, encapsulation efficiency of the liposome(s) is calculated from the concentration, on average, of compounds encapsulated within the liposome(s), which in turn, is determined (e.g., measured) by ultraviolet/visible (UV/Vis) spectrophotometry. In various examples, liposome(s), on average, comprise(s) or exhibit(s) one or more or all of the following: a diameter of from 500 nm to about 700 nm, including all 0.1 nm values and ranges therebetween; or a negative zeta potential of from about 55 mV to about 60 mV, including all 0.1 mV values and ranges therebetween.

A liposome composition can have various desirable properties. In various examples, a liposome composition exhibits heat stability, storage stability, pH stability, or the like, or any combination thereof. In various examples, liposome stability is determined (e.g., measured) by the one or more of the same methods used to determine on or more of the properties of a liposome composition. As used herein, liposome stability is expressed as a percent change in a property of the liposome(s) after exposure of a liposome composition (e.g., an aqueous liposome dispersion or concentrated liposome(s)) to a test condition, such as for example, increased or decreased temperature. In various examples, the liposome(s) is/are heat stable. In various examples, the liposome(s) is/are stable after heating at a temperature of about 60° C. to about 90° C., including all 0.1° C. values and ranges therebetween (e.g., about 60° C. to about 75° C.) for a time of about 30 minutes or greater. In various examples, the liposome(s) is/are storage stable. In various examples, the liposome(s) is/are stable after storing at a temperature of about 4° C. to about 20° C., including all 0.1° C. values and ranges therebetween, for a time of about 4 weeks or greater. In various examples, the liposome(s) is/are stable at an acidic pH. In various examples, the liposome(s) is/are stable at a pH of about 4.5 or lower for a time of about 120 minutes or greater. In various examples, the liposome(s) is/are stable under one or more or all of these stability test conditions.

A liposome composition can have various uses. In various examples, a liposome composition is a food composition, a pharmaceutical composition, a cosmetic composition, or the like, or any combination thereof.

In an aspect, the present disclosure provides methods for delivering one or more active agent(s). Non-limiting examples of methods for delivering the active agent(s) are presented herein. In various examples, a method for delivering the active agent(s) are based on delivery of one or more MFGM composition(s), one or more liposome composition(s), or the like, or any combination thereof, which comprise (or is/are) the active agent(s) (e.g., of the present disclosure or prepared by methods of the present disclosure). In various examples, a method comprises administering the MFGM composition(s), the liposome composition(s), or the like, or any combination thereof, to a subject.

In various examples, MFGM composition(s), the liposome composition(s), or the like, or any combination thereof, comprise(s) (or is/are) and/or encapsulate the active agent(s). In various examples, the administering the MFGM composition(s), the liposome composition(s), or the like, or any combination thereof, to the subject is oral administration. In various examples, an active agent comprises (or is)

a therapeutic agent, a nutrient, a bioactive agent, or the like, or any combination thereof. In various examples, a method comprises administering one or more liposome composition(s) of the present disclosure, where one or more of the active agent(s) is/are chosen from the hydrophobic compound(s), the amphiphilic compound(s), the hydrophilic compound(s), and the like, and any combination thereof.

A therapeutic agent can be any molecule, atom, or the like, or any combination thereof, with therapeutic ability (e.g., drugs (which may be small molecule drugs and the like), nucleic acids, biological materials, radioisotopes, and the like, and combinations thereof). A therapeutic group may be or may be formed from a drug (which may be a small molecule drug), a nucleic acid, or the like. Non-limiting examples of therapeutic agents include, but are not limited to, chemotherapeutic agents, small molecule inhibitors, cytotoxic drugs, antibiotics, antifungal agents, antiparasitic agents, antiviral agents, anti-inflammatory agents, neurological agents, psychotherapy agents, groups comprising one or more radiotherapeutic isotopes (such as 225Ac, 177Lu, and the like), and the like, and combinations thereof. Any of these agents may be drugs (e.g., drugs, which may be small molecule drugs and the like, nucleic acids, biological materials, radioisotopes, and the like). Therapeutic groups may be or may be formed from (e.g., derived from) therapeutic agents (e.g., drugs, which may be small molecule drugs, such as, for example, small molecule inhibitors, cytotoxic drugs, and the like, and the like), nucleic acids, biological materials, radioisotopes, and the like), and the like, that are not considered amenable to oral administration.

In various examples, a liposome composition or the like further comprises one or more material(s) that render the liposome composition suitable for delivery of the active agent(s) to the post-stomach portion of the gastrointestinal tract (e.g., large intestine, small intestine, colon, ileum, or the like, or a combination thereof) of a subject to whom the composition has been orally administered (e.g., enteric materials and the like).

A variety of materials that render a liposome composition suitable for delivery of the active agent(s) to the post-stomach portion of the gastrointestinal tract (e.g., large intestine, small intestine, colon, or the like, or a combination thereof) of a subject can be used in the compositions. The material(s) remain at least partially, substantially, or completely intact until the liposome composition passes through the stomach or until the liposome composition reaches the post-stomach portion of the gastrointestinal tract (e.g., large intestine, small intestine, colon, or the like, or a combination thereof) of the individual.

In various examples, the materials are enteric materials. In various examples, a material that renders liposome composition suitable for delivery of the active agent(s) to the post-stomach portion of the gastrointestinal tract (e.g., large intestine, small intestine, colon, or the like, or a combination thereof) of a subject (e.g., an enteric material or the like) is non-toxic, soluble in the post-stomach portion of the gastrointestinal tract (e.g., large intestine, small intestine, colon, ileum, or the like, or a combination thereof) of an individual, insoluble or substantially insoluble in gastric juice, or any combination thereof.

In various examples, a liposome composition is a pH sensitive composition. In various examples, a material is a pH sensitive material. In various examples, a material (e.g., an enteric material or the like) can be ionized at a pH of 5 to 7.

A material or material(s) may be present as one or more layer(s), which may sequester, coat, or the like, at least a portion of or all of the liposome(s) of a liposome composition. The individual layers may be the same or one or more of the layers is different in terms of at least one structural and/or compositional feature (e.g., material(s), thickness, or the like). The material(s) that render a liposome composition suitable for delivery of the active agent(s) to the post-stomach portion of the gastrointestinal tract (e.g., large intestine, small intestine, colon, or the like, or a combination thereof) of an individual, which may be enteric material(s), may be the outermost material(s) (e.g., the outermost layer of materials) of the liposome composition.

Non-limiting examples of materials, which may be enteric materials, include polymeric materials. Non-limiting examples of polymeric materials include pH sensitive polymers, and the like, and combinations thereof. Non-limiting examples of pH-sensitive polymers include polyacrylamides, phthalate derivatives such as acid phthalate of carbohydrates, amylose acetate phthalate, cellulose acetate phthalate (CAP), other cellulose ester phthalates, cellulose ether phthalates, hydroxypropylcellulose phthalate (HPCP), hydroxypropyl ethylcellulose phthalate (HPECP), hydroxypropyl methylcellulose phthalate (HPMCP), HPMCAS, methylcellulose phthalate (MCP), carboxymethylethyl cellulose (CMEC), polyvinyl acetate phthalate (PVAcP), polyvinyl acetate hydrogen phthalate, sodium CAP, starch acid phthalate, cellulose acetate trimellitate (CAT), styrene-maleic acid dibutyl phthalate copolymer, styrene-maleic acid/polyvinylacetate phthalate copolymer, styrene and maleic acid copolymers, polyacrylic acid derivatives such as acrylic acid and acrylic ester copolymers, polymethacrylic acid and esters thereof, polyacrylic and methacrylic acid copolymers, shellac and copolymers of vinyl acetate and crotonic acid, and the like and combinations thereof. Other non-limiting examples of pH-sensitive polymers include shellac (trade name EmCoat 120 N, Marcoat 125); cellulose acetate phthalate (trade name aquacoat CPD®, Sepifilm™ LP, Klucel®, Aquacoat® ECD, and Metolose®); polyvinylacetate phthalate (trade name Sureteric®); and methacrylic acid (trade name Eudragit®), and the like and combinations thereof.

Non-limiting examples of enteric materials include cellulose acetate phthalate, polyvinyl acetate phthalate, methacrylic acid-methacrylic acid ester copolymers, carboxymethyl ethylcellulose, and hydroxypropyl methylcellulose acetate succinates, and the like, and combinations thereof.

In various examples, at least a portion of the material(s) are one or more additional material(s). In various examples, the additional material(s) is/are chosen from sustained release materials, delayed release materials, controlled release materials, time-dependent delivery materials, and the like, and any combination thereof. An additional material may be suitable for delivery of the active agent(s) to the post-stomach portion of the gastrointestinal tract (e.g., large intestine, small intestine, colon, ileum, or the like, or a combination thereof) of an individual. At least a portion of, substantially all, or all of the additional material(s) may remain at least partially, substantially, or completely intact until the liposome composition passes through the stomach or until the liposome composition reaches the post-stomach portion of the gastrointestinal tract (e.g., large intestine, small intestine, colon, or the like, or a combination thereof) of the individual. A liposome composition comprising one or more additional material(s) may exhibit sustained release, delayed release, controlled release, time-dependent delivery, or the like.

The liposome composition can comprise additional component(s) (which may also be referred to as additive(s)). An additive may be a functional additive or non-functional additive. Non-limiting examples of additives include excipients (such as, for example, fillers, diluents, plasticizers, emulsifiers, and the like), flavoring agents, sweeteners, opacifying agents, buffering agents, tableting agents, tableting lubricants, preservatives, degradation enhancers, mucosal adhesive polymers, gastrorentive agents, and the like, and combinations thereof. An excipient may be a pharmaceutically acceptable excipient. As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Some non-limiting examples of additive(s) which can be used in a composition include sugars, such as, for example, lactose, glucose, sucrose, and the like; starches, such as, for example, corn starch, potato starch, and the like; cellulose, and its derivatives, such as, for example, sodium carboxymethyl cellulose, ethyl cellulose, cellulose acetate, and the like; powdered tragacanth; malt; gelatin; talc; excipients, such as, for example, cocoa butter, suppository waxes, and the like; oils, such as, for example, peanut oil, cottonseed oil, safflower oil, sesame oil, olive oil, corn oil, soybean oil, and the like; glycols, such as, for example, propylene glycol and the like; polyols, such as, for example, glycerin, sorbitol, mannitol, polyethylene glycol, and the like; esters, such as, for example, ethyl oleate, ethyl laurate, and the like; agar; buffering agents, such as, for example, magnesium hydroxide, aluminum hydroxide, and the like; alginic acid; pyrogen-free water; isotonic saline; Ringer's solution; ethyl alcohol; phosphate buffer solutions; and other non-toxic compatible substances employed in pharmaceutical formulations. (See, e.g., REMINGTON'S PHARM. SCI., 15th Ed. (Mack Publ. Co., Easton (1975)).

A composition (e.g., a MFGM phospholipid composition, a liposome composition, or the like, or any combination thereof) can be a food composition, a nutraceutical composition, a pharmaceutical composition, or the like. A composition can be in the form of or is in the form of a pill, a capsule (which may be soft-filled capsule or hard-filled capsule), a tablet, dragees, bead(s), granule(s), or the like. A tablet may be a scored tablet. A composition may comprise composition(s) in a solid form (e.g., a powder, such as, for example, a lyophilized powder). A composition may comprise a liquid comprising the composition(s) (e.g., an aqueous suspension or an aqueous solution, or the like). An aqueous suspension or aqueous solution may comprise buffering agents and/or preservatives. A composition may comprise a gel comprising the composition(s).

In various examples, oral delivery methods are used to deliver one or more composition(s) for treating, preventing, or the like, or any combination thereof, of a current or future condition, disorder, disease, disease state, or the like, or any combination thereof, in an individual. In various examples, one or liposome composition(s) are used in oral delivery methods.

A method of delivering active agent(s) to a subject may comprise orally administering one or more liposome composition(s), which comprise(s) (or is/are) one or more active agent(s), to the individual, where at least a portion of, substantially all, or all of the active agent(s) are delivered to the post-stomach portion of the gastrointestinal tract (e.g., large intestine, small intestine, colon, ileum, or the like) of the individual.

In various examples, at least a portion of (e.g., 40% or more, 50% or more, 60% or more, or 70% or more), substantially all (e.g., at least 90%, at least 95%, or at least 99% of), or all of the liposome(s) of the liposome composition(s) is/are orally delivered to the post-stomach portion of the gastrointestinal tract of a subject pass through the mucus layer and epithelial lining of the small intestine of the individual. In various examples, at least a portion of, substantially all, or all of the liposome(s) of the liposome composition(s) are in a form that retains at least a portion of, substantially all (e.g., at least 90%, at least 95%, or at least 99% of), or all of one or more or all of the activit(ies) of liposome(s) of the liposome composition(s) upon orally delivery to the post-stomach portion of the gastrointestinal tract of an individual.

A method of treating, preventing or the like, or any combination thereof, a subject in need of treatment for a condition, disorder, disease, disease state or potential condition, disorder, disease or disease state, or the like, may comprise orally administering one or more liposome composition(s) of the present disclosure to the subject (which may be an effective amount of the liposome composition(s), where at least a portion of, substantially all, or all of the liposome(s) is/are delivered to the post-stomach portion of the gastrointestinal tract (e.g., large intestine, small intestine, colon, ileum, or the like) of the individual.

"Treating" or "treatment" of any disease or disorder refers, in various examples, to ameliorating the disease, disease state, condition, disorder, side effect, or the like, or a combination thereof (e.g., arresting, reversing, alleviating, or the like) the disease, disease state, condition, disorder, side effect, or the like, or a combination thereof, or reducing the manifestation, extent or severity of one or more clinical symptom(s) thereof, or the like). In various other examples, "treating" or "treatment" refers to ameliorating one or more physical parameter(s), which, independently, may or may not be discernible by the individual. In yet other examples, "treating" or "treatment" refers to modulating disease, disease state, condition, disorder, side effect, or the like, or a combination thereof, either physically, (e.g., stabilization of one or more discernible symptom(s), or the like), physiologically, (e.g., stabilization of one or more physical parameter, or the like), or both. In yet other examples, treating" or "treatment" relates to slowing the progression of the disease, disease state, condition, disorder, side effect, or the like, or a combination thereof. Treating may include administration of an effective amount of the composition(s). An effective amount may be a therapeutic amount, an amount that results in prophylaxis, or the like. In various examples, the individual is considered treated (e.g., individual the individual is not thereafter diagnosed with the disease or disease state, or one or more symptom(s), one or more indication(s), or the like of condition, disorder, disease, or disease state, or the like is at least partially or completely prevented, inhibited, alleviated, or the like).

It is considered that a method of the present disclosure can treat, prevent, or the like, or any combination thereof, any current or potential condition, disease, disease state, or the like, or any combination thereof, that can be conventionally or traditionally targeted, diagnosed, treated, or prevented, or the like, or any combination thereof, with a targeting agent, therapeutic agent, diagnosing agent, or the like, or any combination thereof, that can be delivered using one or more composition(s) of the present disclosure. Non-limiting examples of diseases, disease states, conditions, disorders, side effects, and the like, and potential diseases, disease states, conditions, disorders, side effects, and the like, include infections (e.g., bacterial infections, viral infections, and the like), cancers, neurological conditions/diseases, neurodegenerative diseases, psychological conditions/diseases, inflammatory conditions/diseases, cardio-vascular diseases, and the like.

Typically, a composition is administered in an amount effective to treat, prevent, or the like, or any combination thereof, a current disease, disease state, condition, disorder, side effect, or the like, or a combination thereof, or a potential disease, disease state, condition, disorder, side effect, or the like, or a combination thereof, as described herein. As used herein, the term "effective amount" means that amount of a composition that will elicit the biological or medical response of a tissue, system, animal or human that is being sought, for instance, by a researcher, clinician, or the like. Effective doses of the compounds required to target, diagnose, treat, prevent, or the like, or any combination thereof, the progress of the medical condition are readily ascertained by one of ordinary skill in the art using preclinical and clinical approaches familiar to the medicinal arts.

A physician or veterinarian having ordinary skill in the art can readily determine and prescribe the effective amount of the composition required. The selected dosage level can depend upon a variety of factors including, but not limited to, the activity of the particular composition employed, the time of administration, the rate of excretion or metabolism of the particular composition being employed, the rate and extent of absorption, the duration of the treatment, other drugs, compounds and/or materials used in combination with the particular composition employed, the age, sex, weight, condition, general health and prior medical history of the patient being treated, and like factors well known in the medical arts. For example, the physician or veterinarian could start doses of the composition employed at levels lower than that required in order to achieve the desired therapeutic effect and gradually increase the dosage until the desired effect is achieved.

An effective amount may be a therapeutically effective amount. The term "therapeutically effective amount" includes any amount which, as compared to a corresponding subject who has not received such amount, results in improved treatment, healing, prevention, or amelioration of a disease, disease state, condition, disorder, side effect, or the like or a decrease in the rate of advancement of a disease, disease state, condition, disorder, or the like, or the like. The term also includes within its scope amounts effective to enhance normal physiological function. In various examples, the individual is considered effectively treated if the treated individual is not thereafter diagnosed with the disease or disease state, or one or more symptom(s), one or more indication(s), or the like of condition, disorder, disease, or disease state, or the like is at least partially or completely prevented, inhibited, alleviated, or the like).

An effective amount may result in prophylaxis. The term "prophylaxis" includes prevention and refers to a measure or procedure which is to prevent rather than cure or treat a disease. Preventing may refer to a reduction in risk of acquiring or developing a disease causing at least one clinical symptom of the disease not to develop in a subject that may be exposed to a disease causing agent or a subject predisposed to the disease in advance of disease outset.

In an aspect, the present disclosure provides kits. Non-limiting examples of kits are presented herein. In various examples, a kit comprises (or consist essentially of or consist of) one or more one or more MFGM composition(s), one or more liposome composition(s), or the like, or any combination thereof, e.g., of the present disclosure and/or prepared by methods of the present disclosure.

In various examples, a kit comprises one or more active agent(s), the MFGM composition(s), the liposome composition(s), or the like, or any combination thereof, of the present disclosure (e.g., one or more pharmaceutical composition(s)) of the present disclosure). In various examples, a kit includes a closed or sealed package that contains the active agent(s), the MFGM composition(s), the liposome composition(s), or the like, or any combination thereof. In various examples, the package comprises one or more closed or sealed vials, bottles, blister (bubble) packs, or any other suitable packaging for the sale, distribution, or use of the active agent(s), the MFGM composition(s), the liposome composition(s), or the like, or any combination thereof. The printed material may include printed information. The printed information may be provided on a label, on a paper insert, printed on a packaging material, or the like. The printed information may include information that identifies the active agent(s), the MFGM composition(s), the liposome composition(s), or the like, or any combination thereof, in the package, the amounts and types of other active and/or inactive ingredients in the composition, and instructions for taking the active agent(s), the MFGM composition(s), the liposome composition(s), or the like, or any combination thereof. The instructions may include information, such as, for example, the number of doses to take over a given period of time, and/or information directed to a pharmacist and/or another health care provider, such as, for example, a physician or the like, or a patient. The printed material may include an indication or indications that the active agent(s), the MFGM composition(s), the liposome composition(s), or the like, or any combination thereof and/or any other agent provided therein is for treatment of a subject. In various examples, the kit includes a label describing the contents of the kit and providing indications and/or instructions regarding use of the contents of the kit to treat a subject.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure. The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Example 1

The following is an example of milk fat globule membrane (MFGM) phospholipid extracts, methods of preparing and using MFGM phospholipid extracts, liposomes comprising MFGM phospholipid extracts, and methods of synthesizing and using liposomes comprising MFGM phospholipid extracts.

A new strategy to concentrate phospholipids from buttermilk powder was developed using a food-grade green method based on ethanol-modified SC-$CO_2$ extraction. The effects of extraction conditions, namely, temperature (50 and 60° C.), pressure (30 and 40 MPa), and ethanol concentration (10, 15, and 20%, w/w), on the total lipid yield and phospholipid content were investigated. The ethanol concentration had a more significant effect on the total lipid yield and phospholipid content than the temperature and pressure within the ranges studied. The highest phospholipid recovery was achieved at 60° C., 30 MPa, and 15% (w/w) ethanol where the total lipid yield was 6.3% (w/w) of which 49% (w/w) were phospholipids. Dihydrosphingomyelin (DHSM; 5%), sphingomyelin (SM; 24%), phosphatidylethanolamine (PE; 22%), phosphatidylserine (PS; 2%), phosphatidylinositol (PI; 3%), and phosphatidylcholine (PC; 44%) were the major phospholipids in the ethanol-modified SC-$CO_2$ extract obtained at the optimized conditions. A sequential pure SC-$CO_2$ and ethanol-modified SC-$CO_2$ extraction was carried out to separate the nonpolar lipids in the first fraction and then concentrate the phospholipids in the second fraction. After selective extraction of the nonpolar lipids, the second lipid fraction contained very high phospholipid concentration (76%, w/w). It is believed that this is the highest phospholipid concentration reported from buttermilk powder. Thus, this phospholipid-rich extract can be utilized in the development of functional foods as a food-grade emulsifier that has potential health-promoting effects.

MFGM phospholipid-rich food ingredient was generated from buttermilk powder. Specific objectives were to: (a) investigate the effects of ethanol-modified SC-$CO_2$ extraction conditions, namely, temperature, pressure, and ethanol concentration on the lipid yield and composition, (b) characterize the extracts for their phospholipid and triacylglycerol content and composition, (c) fractionate the buttermilk powder lipids using a sequential pure SC-$CO_2$ and ethanol-modified SC-$CO_2$ extraction.

Materials and Methods. Materials. Dry buttermilk powder was obtained from Land O'Lakes, Inc. (MN, USA). Liquid $CO_2$ (99.99% purity) was supplied by Airgas, Inc. (NY, USA). Ethanol (100%) was acquired from Decon Labs, Inc. (PA, USA), and triacylglycerol standards were purchased from Nu-Chek-Prep, Inc. (MN, USA). Deuterium oxide was acquired from Cambridge Isotope Laboratories, Inc. (MA, USA) and sodium cholate was obtained from Chem-Impex Int'l Inc. (IL, USA). All other chemicals were of analytical grade.

Folch Lipid Extraction. Total lipid extraction from buttermilk powder was carried out following the method of Folch et al. (1957). First, buttermilk powder was mixed with methanol to dissociate lipid-protein interactions. Then, chloroform was included to extract lipids. The ratio of chloroform to methanol was 2:1 (v/v) while the buttermilk powder: solvent ratio was 1:20 (w/v). The extraction was repeated three times and extracts were pooled. Subsequently, the lipid extract was filtered through Whatman #42 filter paper and concentrated using a rotary evaporator (Rotavapor-R, Büchi Labortechnik AG, Flawil, Switzerland) under vacuum at 35° C. Finally, the residual solvent was removed by blowing nitrogen at room temperature (21° C.). The total lipid content was determined by weighing this solvent free extract. The samples were stored at −20° C. under a blanket of nitrogen until further analysis.

SC-$CO_2$ Extraction. SC-$CO_2$ extractions were performed using a laboratory scale SC-$CO_2$ extraction system (SFT-250, Supercritical Fluid Technologies, Inc., DE, USA). The schematic diagram of the system is depicted in FIG. 1. Briefly, 30 g of buttermilk powder was mixed with 30 g of nonporous glass beads to enhance the mass transfer properties. Then, the mixture was loaded into the high-pressure vessel (100 mL), and glass wool was placed at both ends of the vessel. The system was flushed with $CO_2$ to eliminate any air in the vessel at ambient conditions. After flushing with $CO_2$, the vessel was heated to the set temperature (50 or 60° C.) and the micrometering valve was heated to 70° C. to prevent freezing due to Joule Thompson effect. Afterwards, the system was pressurized with $CO_2$ (30 or 40 MPa) using the high-pressure $CO_2$ pump (#5 in FIG. 1). The temperature and pressure of the system were controlled by PID-Fuzzy Logic Controllers. For the ethanol-modified SC-$CO_2$ extractions, the cosolvent pump (miniPump, Milton Roy Company, PA, USA) was turned on to deliver ethanol to the system at concentration of 10, 15, or 20% (w/w). The flow rates of ethanol were predetermined to obtain the required ethanol concentrations in the extraction vessel. After 20 min of static extraction time, the flow rate of $CO_2$ was adjusted to 1 L/min (measured at ambient conditions) using the micrometering valve. The extracted lipids were continuously collected in the sample vial kept in an ice bath. After 4 h of extraction, ethanol was removed from the samples in a vacuum oven at 40° C. Complete removal of ethanol was assured by consecutive weight measurements of the vials. Finally, the samples were flushed with nitrogen and stored at −20° C. until characterized. The total lipid yield was calculated by (weight of the total extract/weight of buttermilk powder used for extraction)×100.

Fractionation of the Buttermilk Lipids Using SC-$CO_2$. Fractionation of the buttermilk lipids (nonpolar and polar lipids) was carried out using the same SC-$CO_2$ extraction system described above. The nonpolar lipid fraction ($1^{st}$ fraction) was first extracted from the buttermilk powder using neat SC-$CO_2$ at the optimized extraction conditions. The extraction of the nonpolar lipids was conducted for 3 h at a $CO_2$ flow rate of 1 L/min (measured at ambient conditions). Then, ethanol was introduced to the system using the cosolvent pump to separate the polar lipids from the buttermilk powder. The ethanol-modified SC-$CO_2$ extraction procedure was followed as described above to extract the phospholipid-rich lipid fraction ($2^{nd}$ fraction). The optimized ethanol-modified SC-$CO_2$ extraction conditions were employed for the extraction of polar lipids. The nonpolar and polar lipid yields were expressed as (weight of the extract (obtained by neat SC-$CO_2$ extraction or ethanol-modified SC-$CO_2$ extraction)/weight of buttermilk powder used for extraction)×100.

Phospholipid Analysis. Phospholipids in the extracts were identified and quantified using a nuclear magnetic resonance (NMR) spectrometer (Bruker Avance III HD 500) according to the method of MacKenzie et al. (2009). A detergent solution composed of sodium cholate (10%, w/w) and EDTA (1%, w/w) was prepared in an aqueous solution of deuterium oxide (20%, v/v). Then, the pH of the detergent solution was adjusted to 7.1 using a 1 M NaOH solution. The samples (30 mg) were mixed with 750 μL of the detergent solution, and 50 μL of $K_2HPO_4$ (6 mg/mL) was included as an internal standard. The samples were placed in an ultrasonic water bath (T-500-3, Terriss-Consolidated Industries, NJ, USA) at 60° C. for 10 min with occasional vortexing. The proton-decoupled $^{31}P$ NMR spectra were collected at 202.3 MHz with 128 scans, 2.0 sec recycle delay, and 81.5 kHz spectral width. The spectra were recorded and analyzed by TopSpin 3.5 and MestRenova 14.1, respectively. The quantification of phospholipids was carried out by relating the area of each analyte to the area and molar concentration of the internal standard.

Triacylglycerol Composition. The triacylglycerol composition of the extracts was determined using a gas chromatograph (GC, HP 5890 Series II, Agilent Technologies, DE, USA) equipped with a flame ionization detector (FID) according to the method of Wagner et al. (2013). Prior to the triacylglycerol analysis, phospholipids were separated from the extracts by acid degumming (Xie and Dunford, 2019). Briefly, 1 g of extract was mixed with 30 μL of citric acid solution (10%, w/w) at 80° C. for 1 h. Then, the mixture was centrifuged at 11340 g for 5 min (IMC-15, International Biotechnologies Inc., CT, USA), and 10 mg of the supernatant was dissolved in chloroform (5 mL). After dilution with chloroform, an aliquot (1 μL) of the sample was injected onto a GC column (MET-Biodiesel, 14 m×0.53 mm×0.16 μm; Supelco Inc., PA, USA) with a retention gap (2 m×0.53 mm). The oven temperature was programmed with an initial hold at 200° C. for 1 min, then followed by an increase to 350° C. at 25° C./min and kept at 350° C. for 5 min. Helium was used as the carrier gas with a constant column head pressure of 62 kPa. The injector and detector temperatures were set to 300 and 380° C., respectively. Triacylglycerols were identified based on carbon number (CN) by comparing the retention times of the authentic triacylglycerol standards, and their composition was calculated using the relative response factors and reported as percentages of the total triacylglycerols.

Statistical Analysis. The results are presented as the mean value±standard deviation. Statistical analysis of the data was carried out using Minitab® 16.1.1 software (Minitab Inc., PA, USA). Analysis of variance (ANOVA) and Tukey's multiple comparison test were applied to determine the statistical differences among the treatments at a significance level of $P<0.05$. All the experiments were conducted in triplicate. All composition values are reported in weight percentages, unless otherwise stated.

Figure 2:
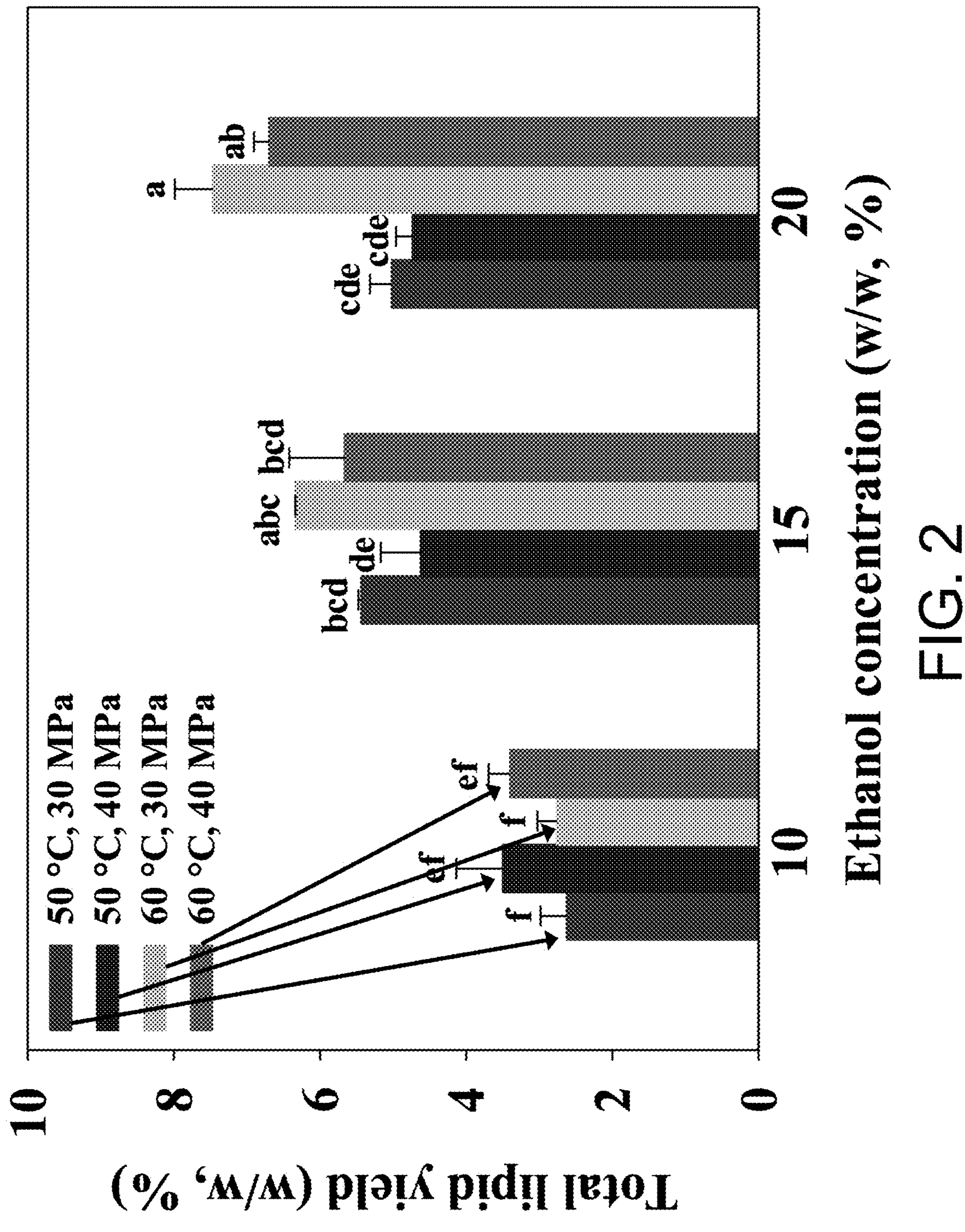
FIG. 2 shows an effect of ethanol concentration on the total lipid yield of an ethanol-modified SC-$CO_2$ extraction system at varying extraction temperatures and pressures.

Effects of Extraction Conditions on the Total Lipid Yield. FIG. 2 depicts the effects of SC-$CO_2$ conditions, namely temperature and pressure, at varying ethanol concentrations on the total lipid yield where the extraction conditions were determined based on the literature and preliminary experiments. The extraction time was set to 4 h according to the preliminary extraction curve data. The highest total lipid yield (7.5±0.5%) was achieved with ethanol-modified SC-$CO_2$ extraction at 60° C., 30 MPa and 20% ethanol. As the temperature was increased from 50 to 60° C., the total lipid yield improved at higher ethanol concentrations. For example, the total lipid yield significantly increased from ca. 5 to 7% with the temperature increase at ethanol concentration of 20% (FIG. 2, $P<0.05$). On the other hand, the pressure increase from 30 to 40 MPa did not significantly affect the total lipid yield in most of the extractions. Similarly, changing the extraction temperature and pressure at low ethanol concentration (10%) did not significantly alter the total lipid yield ($P>0.05$).

Studying the effects of temperature and pressure on the lipid yield separately is very challenging since both temperature and pressure of SC-$CO_2$ dictate its mass transfer properties and in turn its solvating power. In general, the solvating power of SC-$CO_2$ increases with the increase in its density. Thus, increasing the pressure at constant temperature improves the extractability of SC-$CO_2$ since its density increases. The influence of temperature is not as straightforward, however. An increase in temperature decreases the density of SC-$CO_2$, inhibiting extraction, but increases the vapor pressure of the solutes, enhancing extraction. This phenomenon is known as the crossover of solubility isotherms where the pressure determines which effect is more dominant (decrease in the density or increase in the solute vapor pressure). The crossover pressure for milk fat triacylglycerols is expected to be between 20 and 25 MPa since the solubility of milk fat triacylglycerols in SC-$CO_2$ decreased with temperature increase from 50 to 80° C. at ca. 20 MPa. However, their solubility increased with temperature at pressures above 25 MPa. Therefore, the total lipid yield increased with increasing the temperature at isobaric conditions as both pressures investigated (30 and 40 MPa) were above the crossover pressure (FIG. 2). Similarly, previously reported theoretical lipid solubility parameters were in good agreement with the findings of this example where the solubility of the lipids increased with temperature. However, previously reports obtained higher lipid solubility from buttermilk powder with temperature increase from 40 to 50° C. but a decrease in lipid solubility at 60° C. Moreover, the fat reduction from buttermilk powder did not significantly change with temperature (40, 50, and 60° C.) at all levels of pressure (15, 25, and 35 MPa) in previous reports.

Ethanol was introduced into the extraction system to increase the polarity of the solvent mixture to efficiently extract polar lipids besides the nonpolar lipids. An ethanol concentration of 5% was investigated in preliminary studies, yet the total lipid yield was relatively low (ca. 2%). Therefore, 5% ethanol concentration was excluded from this example while the effects of ethanol concentrations of 10, 15, and 20% were investigated in detail. Although increasing ethanol concentration from 10 to 15% mostly increased the total lipid yield (FIG. 2), further increasing the ethanol concentration did not significantly increase the total lipid yield ($P>0.05$). To illustrate, the total lipid yields obtained at 60° C. and 30 MPa with ethanol concentrations of 10, 15, and 20% were 2.8, 6.3, and 7.5%, respectively. The increase in the total lipid yield can largely be explained by the increase in the recovery of polar lipids from the buttermilk powder. Also, as ethanol extracted the polar lipids from the MFGM, the nonpolar lipids in the core became more accessible to the SC-$CO_2$, which in turn increased the total lipid yield. Besides, the nonpolar lipids may have acted as a cosolvent and increased the extraction of polar lipids. Very recently, similar effects were observed for ethanol concentration on the total lipid yield from camelina press cakes and scallop byproducts where the total lipid yield increased with increasing the ethanol concentration from 7 to 15%, but did not change with a further increase in ethanol concentration to 30% at 45° C. and 25 MPa.

Figure 3:
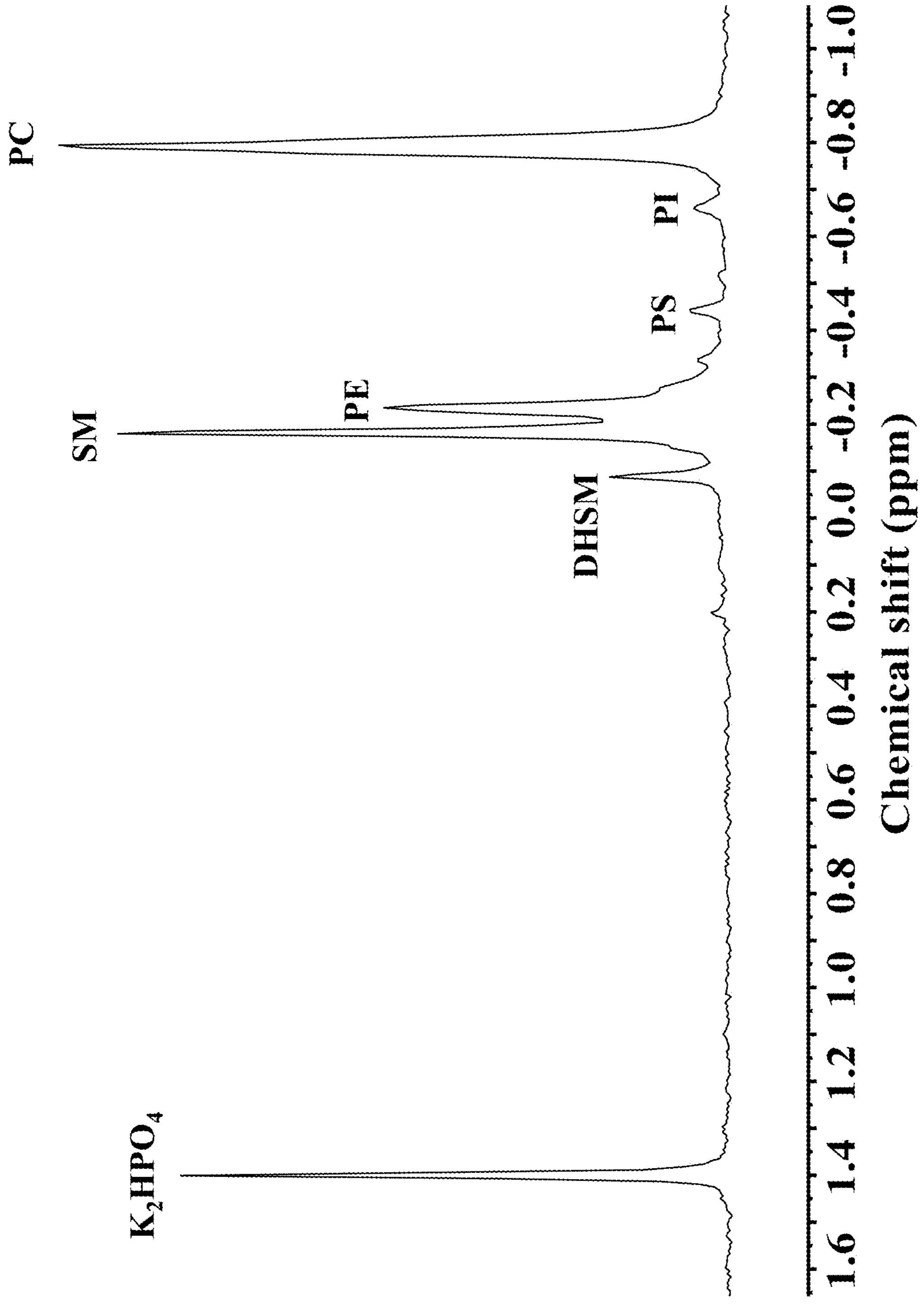
FIG. 3 shows a phosphorus-31 nuclear magnetic resonance ($^{31}P$ NMR) spectrum of the polar lipids in a buttermilk powder extract. DHSM=dihydrosphingomyelin; SM=sphingomyelin; PE=phosphatidylethanolamine; PS=phosphatidylserine; PI=phosphatidylinositol; PC=phosphatidylcholine.

Effects of Extraction Conditions on the Phospholipid Content. The phospholipid contents of the extracts obtained by ethanol-modified SC-$CO_2$ extraction were identified and quantified using $^{31}P$ NMR (FIG. 3). The major phospholipids in the extracts were DHSM, SM, PE, PS, PI, and PC with $^{31}P$ NMR signals at δ −0.09 ppm, δ −0.18 ppm, δ −0.23 ppm, δ −0.44 ppm, δ −0.66 ppm, and δ −0.79 ppm, respectively. Similar $^{31}P$ NMR chemical shifts of dairy phospholipids have been reported previously. Minor phospholipids, namely, 2-lysophosphatidylethanolamine (2LPE) and 2-lysophosphatidylcholine (2LPC) were also observed in some samples at δ −0.20 ppm and δ− 0.34 ppm, respectively. However, their concentration was very low as seen from the intensity of those peaks (FIG. 3). In addition, the signal at δ

1.40 ppm corresponding to $K_2HPO_4$ did not interfere with other peaks and was used as an internal standard to quantify phospholipids.

Figure 4:
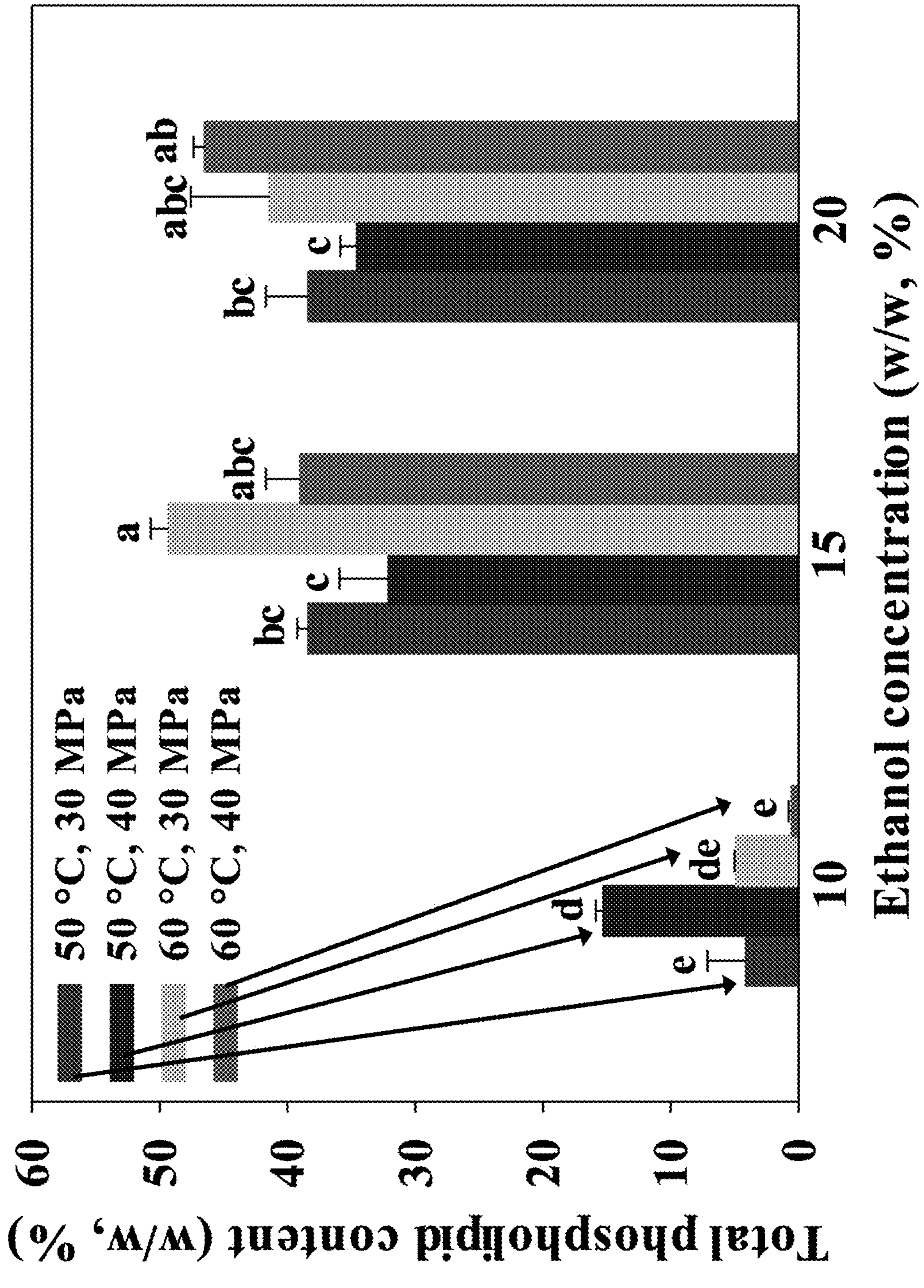
FIG. 4 shows an effect of ethanol concentration, temperature and pressure on the total phospholipid content of a buttermilk powder extract.

The total phospholipid contents (sum of all phospholipids) of the ethanol-modified SC-$CO_2$ extracts are presented in FIG. 4. The highest total phospholipid content (49%) was attained with the extraction at 60° C., 30 MPa, and 15% ethanol concentration. However, the total phospholipid content of 49% did not significantly alter by increasing the extraction pressure or ethanol concentration at the same temperature (60° C.). At higher ethanol concentrations (15 and 20%), increasing the temperature significantly improved the extraction of phospholipids at both pressures studied ($P<0.05$), which was due to the increase in the solubility of phospholipids and their mass transfer properties. On the other hand, increasing the pressure from 30 to 40 MPa did not affect the total phospholipid content in most of the extraction conditions (FIG. 4) which agreed with the total lipid yield data (FIG. 3).

The effect of ethanol concentration on the total phospholipid yield was more dominant than that of temperature or pressure (FIG. 4). As expected, the total phospholipid yield drastically increased from ca. 6% to 40% when the ethanol concentration was increased from 10 to 15% due to the modification of the solvent polarity that favors the extraction of polar lipids (Catchpole et al., 2009). Nevertheless, further increase in the ethanol concentration did not improve the phospholipid extraction. Previously, the extraction of lipids from whey protein phospholipid concentrate (WPPC) was studied using SC-$CO_2$ and ethanol as a cosolvent, where the effects of temperature (40-60° C.), pressure (35-55 MPa) and ethanol concentration (10-20%) on the phospholipid content were investigated. Similarly, increasing ethanol concentration from 10 to 15% enhanced the phospholipid extraction whereas phospholipid recovery was not improved with further increase in ethanol concentration. In another study, the extraction of phospholipids from buttermilk 50 kDa retentate was carried out using ethanol concentrations of 10 and 20% at a constant extraction temperature (40° C.) and pressure (30 MPa). They similarly found that an ethanol concentration of 10% was not able to extract any phospholipids from the buttermilk 50 kDa retentate while the phospholipid extraction considerably increased by increasing the ethanol concentration to 20%.

Comparison of Folch and Ethanol-modified SC-$CO_2$ Extractions. Folch extraction was performed to determine the total lipid content of the buttermilk powder since it has the capability of isolating both polar and nonpolar lipids. The total lipid content of buttermilk powder was 9.0±0.2%, where the lipid fraction was composed of 59.8±0.5% phospholipids. Correspondingly, the buttermilk powder contained considerable amount of phospholipids (5.4%). The major components of buttermilk powder were previously reported as 31-38% protein, 5-17% lipids, ca. 52% lactose, and ca. 7% ash, with variation mostly due to the source and processing of the buttermilk powder. The total lipid content (9%) of the buttermilk powder used for extractions falls within the range of lipid contents reported before. Specifically, buttermilk powder from the same supplier had a very similar total lipid content (10%) as determined by Folch extraction method. Nonetheless, the total phospholipid content of the buttermilk powder used in this example was higher than the values stated in the literature, which could be due to the buttermilk powder source as stated before. To illustrate, a first study found the phospholipid content of buttermilk powder as 3.3%. On the other hand, buttermilk powder in a second study had significantly lower phospholipid content (1.3%), yet the buttermilk 50 kDa retentate used for ethanol-modified SC-$CO_2$ extraction contained much higher amount of phospholipids (11.1%). In addition, the phospholipid content of the whey buttermilk powder (7.2%) was higher than that reported in this example (5.4%).

The optimum ethanol-modified SC-$CO_2$ condition was determined based on both the total lipid yield and phospholipid content of the extract to maximize phospholipid recovery from the buttermilk powder. Even though the phospholipid recovery was not significantly different among the extractions carried out at 60° C. with different pressures (30 vs. 40 MPa) and ethanol concentrations (15 vs. 20%), the optimum extraction condition was chosen as 60° C., 30 MPa, and 15% ethanol concentration owing to energy consumption and process economics concerns. The extraction at these optimized conditions yielded a phospholipid recovery of 58%.

The phospholipid composition of the extracts obtained by Folch and ethanol-modified SC-$CO_2$ (60° C. and 30 MPa) from buttermilk powder are presented in Table 1.

TABLE 1

| Sample | DHSM | SM | PE | PS | PI | PC |
|---|---|---|---|---|---|---|
| Folch extract | 3.8 ± 0.4$^a$ | 33.2 ± 1.5$^a$ | 25.1 ± 0.2$^a$ | 5.1 ± 1.0$^a$ | 3.9 ± 0.3$^a$ | 28.9 ± 0.3$^b$ |
| Ethanol (15%)-modified SC—$CO_2$ extract | 5.0 ± 0.3$^a$ | 24.3 ± 0.3$^b$ | 22.1 ± 0.1$^b$ | 2.2 ± 0.1$^a$ | 2.7 ± 0.8$^a$ | 43.6 ± 0.9$^a$ |

*Data are expressed means ± standard deviations. Means in the same column with different letters are significantly different ($P < 0.05$). DHSM = dihydrosphingomyelin; SM = sphingomyelin; PE = phosphatidylethanolamine; PS = phosphatidylserine; PI = phosphatidylinositol; PC = phosphatidylcholine.

The predominant phospholipids in buttermilk powder were DHSM (3.8%), SM (33.2%), PE (25.1%), PS (5.1%), PI (3.9%), and PC (28.9%) as determined by $^{31}P$ NMR analysis of the Folch extracted lipid fraction. In the literature, the content of major phospholipids in buttermilk powder varies between 0-4.6% DHSM, 20.4-43.1% SM, 18.6-25.7% PE, 6.3-9.7% PS, 0.7-10.8% PI, and 27.0-31.3%. Variation in these values was due to the buttermilk source as well as the extraction and analysis techniques. On the other hand, the phospholipids in the ethanol-modified SC-$CO_2$ extract obtained at the optimized extraction conditions were composed of 5.0% DHSM, 24.3% SM, 22.1% PE, 2.2% PS, 2.7% PI, and 43.6% PC which were significantly different from the phospholipid composition attained by Folch extraction ($P<0.05$). Specifically, among phospholipids, PC was more favorably extracted by ethanol-modified SC-$CO_2$, owing to its higher solubility in ethanol-SC-$CO_2$ mixture. Therefore, the ratio of PC was increased from 28.9% to 43.6% when ethanol-modified SC-$CO_2$ extraction was implemented instead of Folch extraction.

Figure 5:
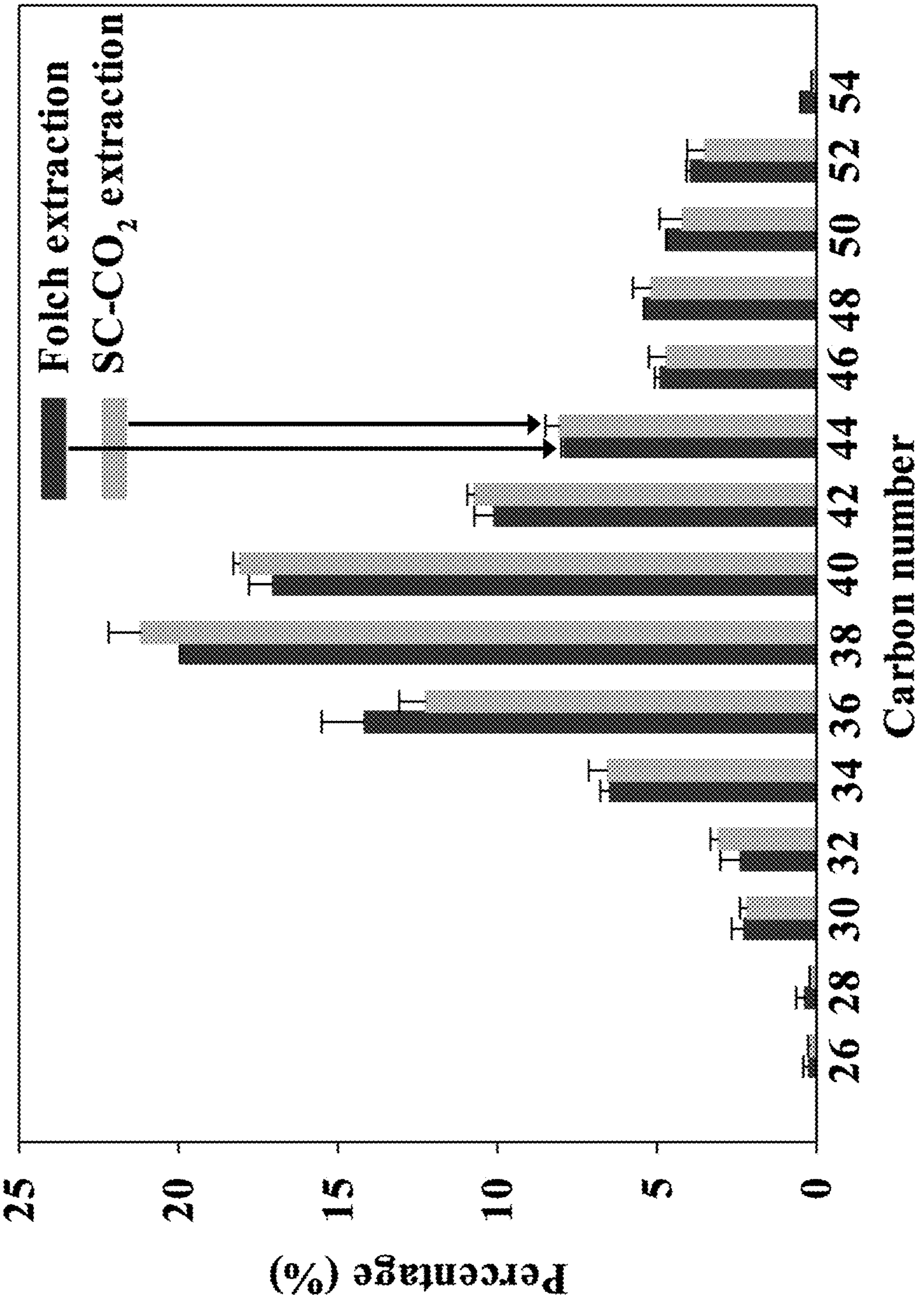
FIG. 5 shows triacylglycerol compositions of nonpolar lipids obtained by a Folch and an ethanol-modified SC-$CO_2$ extraction.

Furthermore, the triacylglycerol compositions of the Folch and ethanol-modified SC-$CO_2$ extracts are shown in FIG. 5. The ethanol-modified SC-$CO_2$ extract obtained at the optimized extraction conditions (60° C., 30 MPa and 15% ethanol) was used for triacylglycerol composition analysis. The phospholipids were separated prior to the GC-FID analysis to eliminate the co-elution of polar lipids with low molecular weight triacylglycerols. Both extraction methods resulted in similar triacylglycerol distributions where CN34, CN36, CN38, CN40, CN42, and CN44 were the major triacylglycerols with ratios ca. 7, 13, 20, 18, 9, and 8%, respectively. Likewise, comparable triacylglycerol distribution have been reported in the lipid fraction isolated from buttermilk. In previous reports, triacylglycerol profile was mostly consisted of CN34, CN36, CN38, CN40, and CN42 triacylglycerol groups. Also, similar triacylglycerol compositions were reported in buttermilk.

Fractionation of Buttermilk Lipids. After optimization of the ethanol-modified SC-$CO_2$ extraction conditions, fractionation of the buttermilk lipids was carried out using a sequential pure SC-$CO_2$ and ethanol-modified SC-$CO_2$ extraction (Table 2 shows a material balance of the Folch and SC-$CO_2$ extractions from 100 g buttermilk powder).

TABLE 2

| Material | Folch Chloroform:methanol (2:1, v/v) | SC—$CO_2$ Pure SC—$CO_2$ | 15% ethanol-modified SC—$CO_2$ |
|---|---|---|---|
| Total lipids (w/w, %) | 9.0 ± 0.2[a] | 2.5 ± 0.2[c] | 4.3 ± 0.3[b] |
| Phospholipids (w/w, % of total lipids) | 59.8 ± 0.5[b] | 0.2 ± 0.1[c] | 76.2 ± 2.0[a] |

*Data are expressed means ± standard deviations. Means in the same row with different letters are significantly different (P < 0.05).

The total lipid yields obtained by Folch extraction from the original buttermilk powder, and pure SC-$CO_2$ (the 1$^{st}$ fraction) and ethanol-modified SC-$CO_2$ (the 2$^{nd}$ fraction) extractions are given in Table 2. In addition, the corresponding total phospholipid content of each fraction was determined (Table 2). The buttermilk powder contained 9.0% total lipids as stated before, whereas the remaining lipids in the buttermilk powder after the sequential SC-$CO_2$ extraction were only 2.2%. Therefore, the sequential pure SC-$CO_2$ and ethanol-modified SC-$CO_2$ extraction was able to isolate 75% of the total lipids presented in buttermilk powder where most of the nonpolar lipids (97%) were recovered.

The first part of the sequential extraction was performed using pure SC-$CO_2$ at 60° C. and 40 MPa where the highest total lipid yield was achieved (FIG. 2). The total lipid yield of the pure SC-$CO_2$ extraction (1$^{st}$ fraction) was 2.5±0.2%. This fraction was rich in triacylglycerols and contained only 0.25±0.03% phospholipid since pure SC-$CO_2$ was employed. On the other hand, the second part of the extraction was carried out at 60° C. and 30 MPa with 15% ethanol which were the optimized ethanol-modified SC-$CO_2$ extraction conditions. The 2$^{nd}$ part of the extraction produced significantly higher total lipid yield (4.3±0.2%) compared to the 1$^{st}$ part of the extraction (2.5%, P<0.05) due to the increased separation of polar lipids with the introduction of ethanol (Table 2). Thus, the 2$^{nd}$ fraction collected was concentrated in phospholipids and had 76.2±2.0% total phospholipid content. The phospholipid composition of the 2$^{nd}$ fraction (5.8% DHSM, 26.6% SM, 18.3% PE, 1.8% PS, 4.1% PI and 43.4% PC) was similar to that obtained at the same extraction conditions but without pure SC-$CO_2$ pre-extraction (Table 1). Similarly, the triacylglycerol composition of the nonpolar lipids did not change with the fractionation extractions.

So far, the highest phospholipid content reported was 56.2% from a fraction of buttermilk powder (spray-dried 50 kDa retentate) following a similar approach where pure SC-$CO_2$ and ethanol-modified SC-$CO_2$ extractions (40° C., 30 MPa, and 20% ethanol) were employed. However, the buttermilk used for SC-$CO_2$ extraction was pre-treated with enzymatic hydrolysis, ultrafiltration, and spray drying. Besides, the total extraction time was 13 h. In this example, a significantly higher phospholipid purity (76%) was attained in a shorter extraction time (7 h). In another approach to purify phospholipids, phospholipids were concentrated in the buttermilk powder by removing the nonpolar lipids using SC-$CO_2$ extraction. The phospholipid content of the buttermilk powder was enriched up to 9%. Nevertheless, the SC-$CO_2$ treated buttermilk powder was still mostly composed of proteins. Also, the phospholipid content of the whey buttermilk powder, pre-treated by ultrafiltration, was increased from 7.2 to 12.0% by SC-$CO_2$ extraction of the nonpolar lipids. Yet, the presence of other macromolecules in those products drastically limits their applications.

Conclusions. In this example, phospholipid-rich lipid extracts were isolated from buttermilk powder using a green approach based on SC-$CO_2$ technology. The extraction conditions were investigated and optimized for the highest phospholipid recovery from buttermilk powder. The effect of ethanol concentration on the lipid yield and phospholipid content was more dominant than that of extraction temperature or pressure. The optimized ethanol-modified SC-$CO_2$ extraction conditions were 60° C., 30 MPa, and 15% ethanol which resulted in 6.3% total lipid yield. The obtained extract contained high amount of phospholipids (49%) where the major phospholipids were DHSM (5.0%), SM (24.3%), PE (22.1%), PS (2.2%), PI (2.7%), and PC (43.6%). PC was selectively extracted by ethanol-modified SC-$CO_2$ which in turn increased the relative PC ratio in the extract compared to that in the buttermilk powder (28.9%). The triacylglycerol compositions of the ethanol-modified SC-$CO_2$ and Folch extracts were similar. Furthermore, the fractionation of the buttermilk lipids (nonpolar and polar) was achieved by sequential pure SC-$CO_2$ and ethanol-modified SC-$CO_2$ extraction. Selectively isolating the nonpolar lipids in the first part of the extraction using pure SC-$CO_2$ resulted in concentrating the phospholipids in the second part of the extraction. Consequently, a very high purity phospholipid extract (76%) was attained in the second lipid fraction. This example produces a high-purity phospholipid concentrate using only food-grade materials, namely ethanol and SC-$CO_2$. Thus, the phospholipid-rich extract can be utilized as a new source of emulsifier in numerous functional food preparations.

Example 2

The following is an example of milk fat globule membrane (MFGM) phospholipid extracts, methods of preparing and using MFGM phospholipid extracts, liposomes comprising MFGM phospholipid extracts, and methods of synthesizing and using liposomes comprising MFGM phospholipid extracts.

Heat stable liposomes loaded with multivitamins were successfully synthesized from MFGM phospholipid concentrate. The MFGM phospholipids were first isolated from buttermilk powder, an undervalued dairy byproduct, by means of sequential pure SC-$CO_2$ and ethanol-modified SC-$CO_2$ extraction. The final extract was composed of 75% phospholipids, the highest MFGM phospholipid purity reported so far from buttermilk powder. Extracted MFGM phospholipids concentrate was utilized in liposome synthesis by the rapid expansion of supercritical solution using a venturi-based system (Vent-RESS) for vacuum driven cargo loading. Liposome synthesis was also conducted using sunflower phosphatidylcholine (SFPC) for comparison. To test the performance of the liposomes, vitamins E and C were used as model hydrophobic and hydrophilic bioactives, respectively. MFGM phospholipids mostly produced unilamellar vesicular type liposomes with an average diameter of 533 nm and ζ-potential of −57 mV. The encapsulation efficiency (EE) of vitamins E and C in MFGM liposomes were 77% and 65%, respectively. Even after heating at 90° C. for 30 minutes, MFGM liposomes retained structural integrity as shown in their confocal micrographs, structural characterizations, and EE measurements. In contrast, SFPC liposomes disintegrated at temperatures above 60° C. Thus, MFGM liposomes have the potential to protect the nutritional and functional properties of bioactive compounds during extended exposure to thermal treatment. This example describes a green method to extract dairy phospholipids and fabricate liposomes for the delivery of bioactive compounds with application in the food, pharmaceutical, and cosmetic industries with a great potential for scale-up.

The development of a novel and sustainable process for synthesizing liposomes as described herein involves the rapid expansion of supercritical solution using a venturi system (Vent-RESS) for concomitant vacuum driven cargo loading. To produce heat-stable liposomes, milk fat globule membrane (MFGM) phospholipids was used as a coating material. The MFGM is a unique structure of phospholipids and proteins surrounding the milk fat globule. It contains a wide variety of phospholipids such as sphingomyelin (SM), phosphatidylethanolamine (PE), phosphatidylserine (PS), phosphatidylinositol (PI), and phosphatidylcholine (PC). The thermotropic nature of MFGM phospholipids allows for the emulsion stability of milk fat globules even at high temperatures. Thus, it was considered that a liposomal system formed from MFGM phospholipids would be heat stable.

To increase the solubility of polar solutes, a polar co-solvent (such as ethanol) can be incorporated. To isolate the MFGM phospholipids in buttermilk powder, the nonpolar lipids were first extracted using pure SC-$CO_2$, then the phospholipids were isolated using ethanol-modified SC-$CO_2$. In this example, the second lipid fraction of high-purity MFGM phospholipids was used for liposome synthesis. Vitamins E and C were co-encapsulated in the liposomes as model hydrophobic and hydrophilic bioactive molecules. For comparison, liposomes were also produced using sunflower phosphatidylcholine (SFPC). The heat stability of synthesized liposomes was quantified by analyzing the structure, size, surface charge, and encapsulation efficiency of bioactives.

Materials And Methods. Materials. Vitamin E (α-tocopherol, 95.5%), protamine sulfate, Nile Red, cholesterol (92.5%), and dimethyl sulfoxide (DMSO) (99.9%) were purchased from Sigma-Aldrich (St. Louis, MO, USA). Carbon dioxide ($CO_2$) (99.99%) was purchased from Airgas (Ithaca, NY, USA). Calcein and Tris(hydroxylmethyl) aminomethane (TRIS) were purchased from Acros Organics (Morris, NJ, USA) and Bio-Rad (Hercules, CA, USA), respectively. Vitamin C (L-ascorbic acid, 99%) was purchased from TCI America (Portland, OR, USA). Phosphatidylcholine (PC) (Sunlipion® 90, 99%), extracted from non-genetically modified sunflower lecithin was donated by Perimondo (Florida, NY, USA). Dry buttermilk powder was purchased from Land O'Lakes, Inc. (Arden Hills, MN, USA).

Figure 6A:
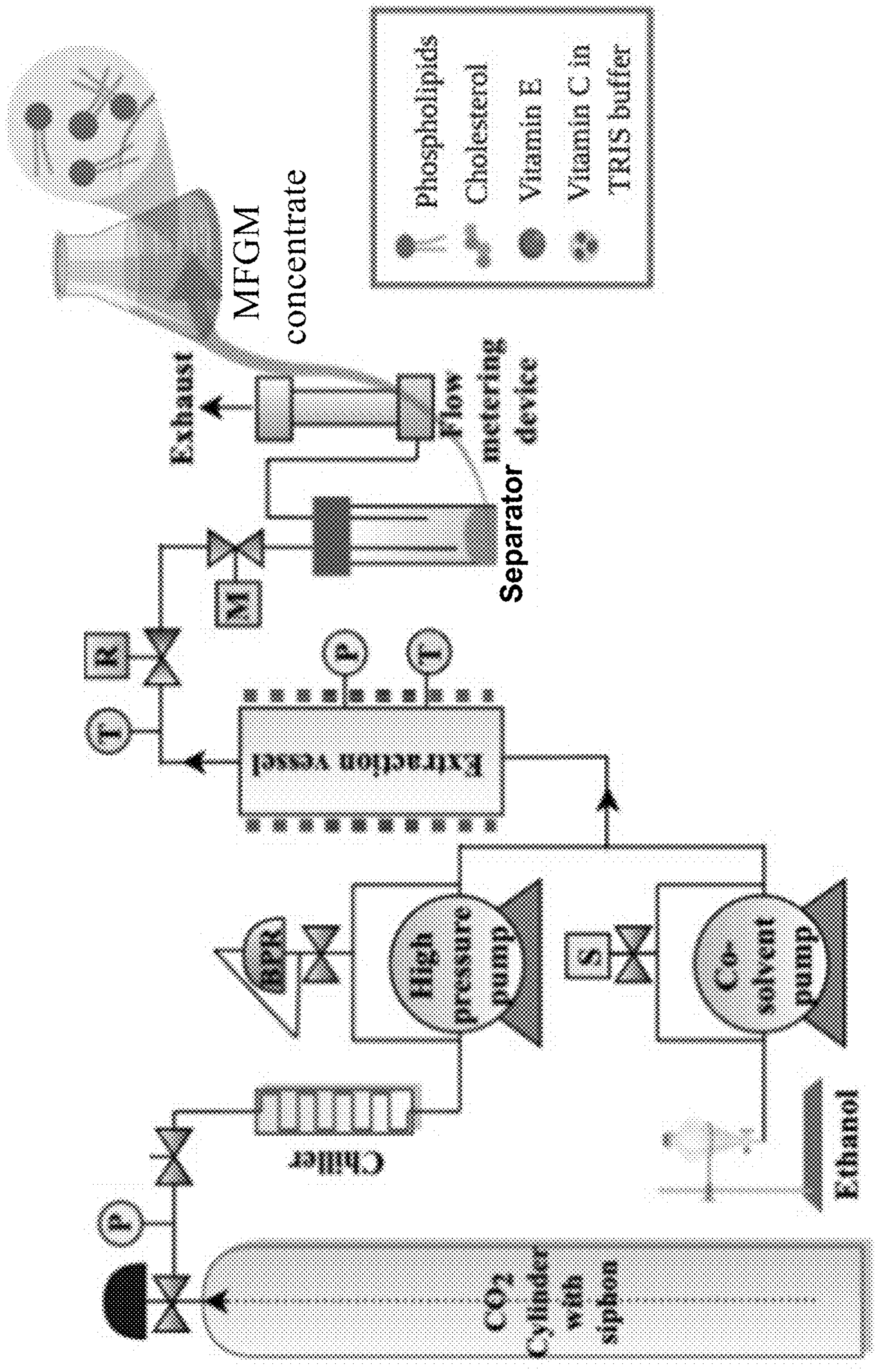
FIGS. 6A-6C show schematic representations of (FIG. 6A) a MFGM phospholipid extraction unit, (FIG. 6B) a Vent-RESS system, and (FIG. 6C) a liposome formation mechanism inside the venturi eductor.

Extraction Of MFGM Phospholipids Using Ethanol-Modified SC-$CO_2$. Sequential extraction of the nonpolar ($1^{st}$ fraction) and polar ($2^{nd}$ fraction) lipids from buttermilk powder was carried out using a laboratory scale SC-$CO_2$ extraction system equipped with a cosolvent pump (SFT-250, Supercritical Fluid Technologies, Inc., Newark, DE, USA). The details of the extraction system are depicted in FIG. 1 and FIG. 6A, First, buttermilk powder (30 g) was blended with nonporous glass beads (30 g) to enhance mass transfer properties. This mixture was then loaded into a high-pressure vessel (100 mL) with glass wool layers at both ends of the vessel. Next, the system was flushed with $CO_2$ under ambient conditions to purge air from the vessel. Afterward, the system was heated to 60° C. and pressurized to 40 MPa with $CO_2$. After 20 minutes of static extraction, the $CO_2$ flow rate was adjusted to 1 L/minute (measured at ambient conditions) using a micro-metering valve. The micro-metering valve was heated to 70° C. throughout the extractions to prevent freezing due to the Joule Thompson effect. The $1^{st}$ fraction (rich in nonpolar lipids) was continuously collected for 3 h using pure SC-$CO_2$. Next, the system was repressured to 30 MPa at the same temperature (60° C.) and ethanol was introduced at a concentration of 15% (w/w). After 20 minutes of static extraction with ethanol, the $CO_2$ flow rate was set to 1 L/min (measured at ambient conditions). The extracted lipid and ethanol mixture were continuously collected for 4 h in a sample vial kept in an ice bath. Subsequently, ethanol was removed from the extracts in a vacuum oven at 40° C. This $2^{nd}$ fraction (rich in polar lipids) was later used for liposome synthesis. All the samples were stored under nitrogen at −20° C. until further use. The total lipid yield was calculated using the following equation:

$$\text{Total lipid yield (\%)} = \frac{\text{weight of the solvent free extract}}{\text{weight of buttermilk powder used for extraction}} \times 100 \quad [1]$$

Furthermore, the total lipid content of buttermilk powder was determined using Folch extraction method where chloroform:methanol (2:1, v/v) mixture was used to extract both polar and nonpolar lipids. Briefly, methanol was first mixed with buttermilk powder. Then, chloroform was added to the mixture to extract lipids. Later, the lipid extract was filtered through a Whatman #42 filter paper, and the solvent was removed using a rotary evaporator (Rotavapor-R, Büchi Labortechnik AG, Flawil, Switzerland). The total lipid content of buttermilk powder was determined from the weight of this solvent-free extract.

Liposome Synthesis With A SC-$CO_2$ Assisted System. Liposome synthesis was performed with two types of phospholipids: (i) SFPC and (ii) MFGM phospholipids. To determine the efficacy of bioactive encapsulation in the synthesized liposomes, vitamins E and C were used as model hydrophobic and hydrophilic bioactives, respectively. The lipophilic cargo was prepared by mixing the phospholipids, cholesterol, and vitamin E at a weight ratio of 5:1:1 at 45° C. until homogeneous mixture was obtained. The mixture was then solidified at 4° C. for loading convenience. Cholesterol was added to increase the rigidity and the strength of the phospholipid bilayer by restricting the movement of the long alkyl chains, thus increasing liposome stability and preventing structural disintegration. The aqueous cargo was prepared as a solution of 0.125 M vitamin C in a 0.02 M TRIS buffer solution (pH=7.4).

Figure 6B:
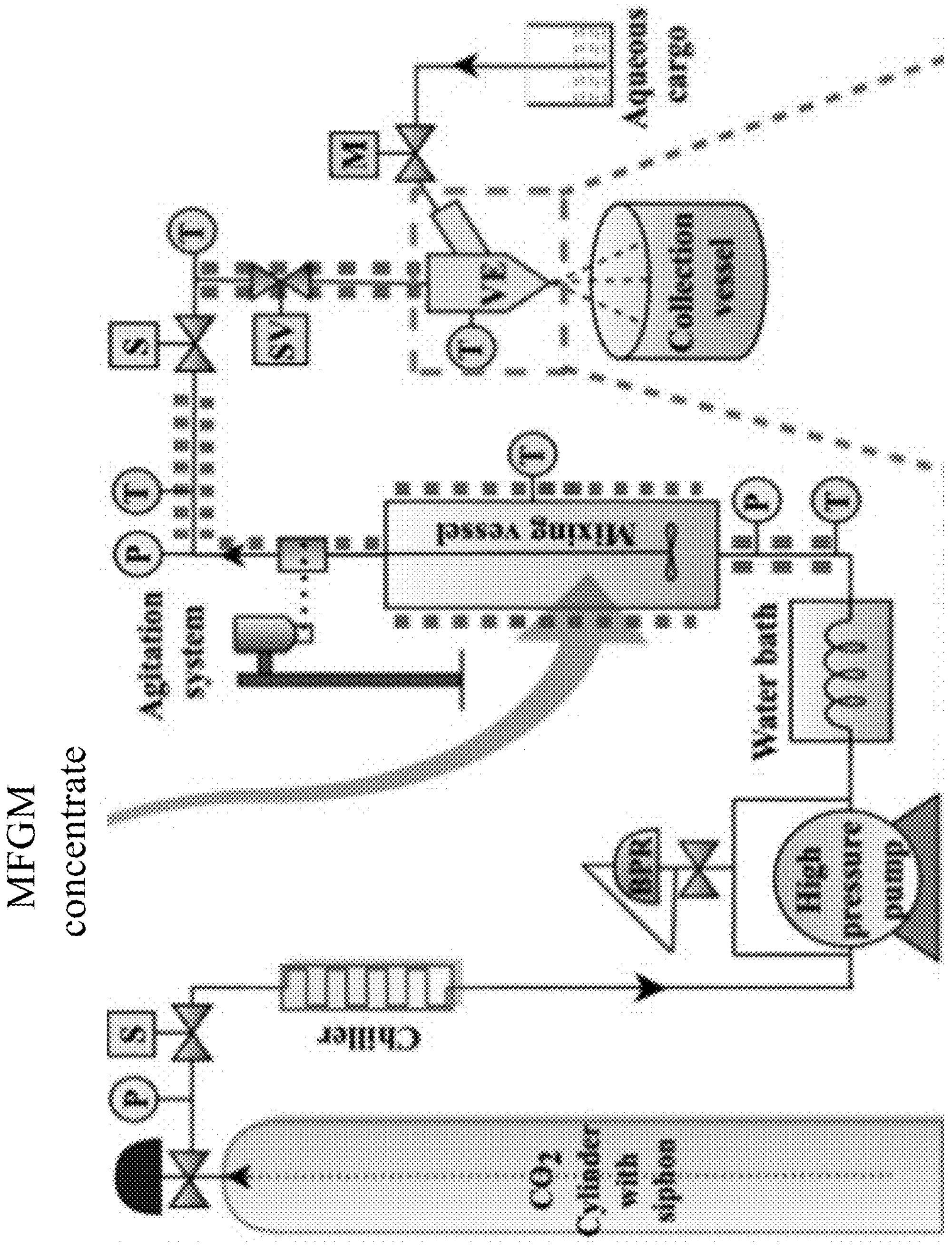

The liposomes were prepared using a $SC\text{-}CO_2$ assisted Vent-RESS system. FIG. 6B depicts a simple schematic representation of the Vent-RESS system. This apparatus consists of three main parts: a high-pressure pump (HPP), a stainless-steel mixing vessel equipped with a stirrer, and a 1.5 mm (internal diameter) expansion nozzle located inside an eductor. For liposome synthesis, the mixing vessel was loaded with the lipophilic cargo, and the vessel was pressurized to 17.2 MPa and heated to 45° C. The $SC\text{-}CO_2$ mixture was then stirred continuously for 1 h to equilibrate. A solenoid valve was used to release pressure for a predetermined time interval. At this stage, the phospholipid-rich $SC\text{-}CO_2$ expanded toward the expansion nozzle. To avoid precipitation of phospholipids before they reached the nozzle, $SC\text{-}CO_2$ was maintained at a temperature of 45° C. The aqueous cargo was introduced to the expansion nozzle by a tube with an internal diameter of 1.3 mm mounted at a 45° angle to the $SC\text{-}CO_2$ flow.

Figure 6C:
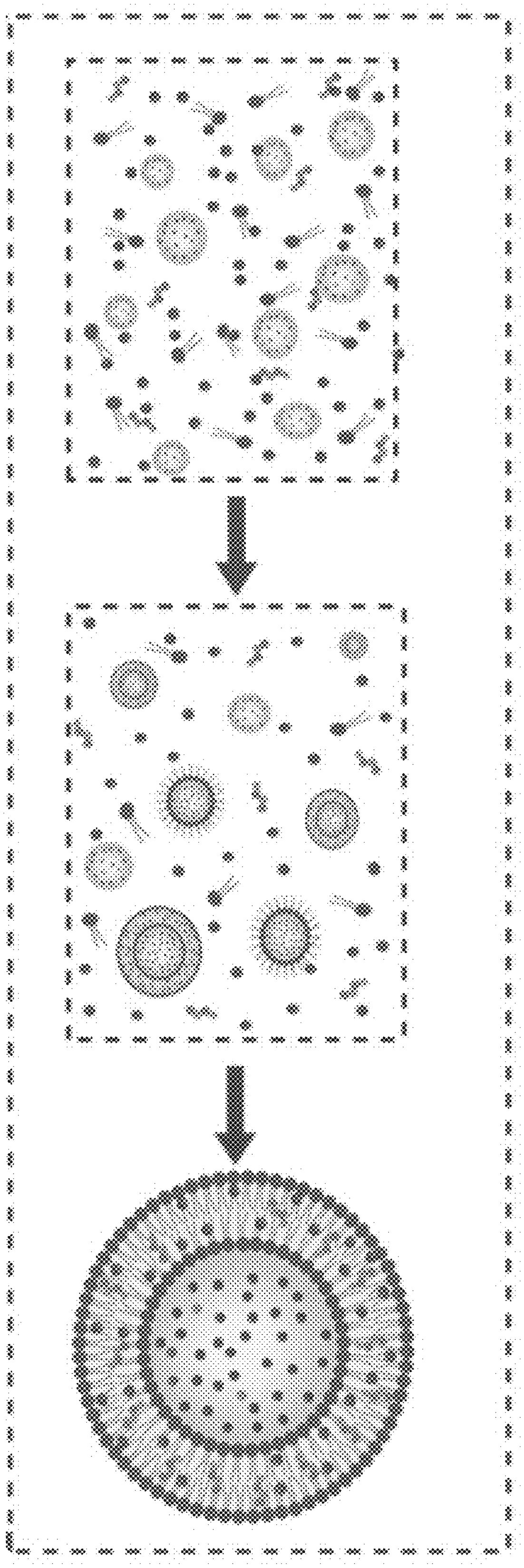

Upon pressure release by the solenoid valve, the phospholipid-laden $SC\text{-}CO_2$ rapidly expanded, generating high velocities through the expansion nozzle. Consequently, a vacuum was formed at the throat of the eductor (i.e. vena contracta) due to the Bernoulli effect, enabling suction of the aqueous cargo. The aqueous stream enters the eductor and collides with the $CO_2$ stream, fragmenting into submicron droplets. At this stage the $CO_2$ loses its supercritical properties, and nucleation of the dissolved phospholipids begins. To attain stability, phospholipid molecules coalesce around miniscule water droplets, self-assembling into bilayer liposomes (FIG. 6C). During this process, the eductor-nozzle assembly was heated to 80° C. to prevent phospholipid condensation as a result of cooling by the Joule-Thompson effect and $CO_2$ expansion. Heating the eductor-nozzle assembly also helps to minimize the interfacial tension between the aqueous and phospholipid phases. The resulting liposomes were collected in 10 mL of TRIS buffer solution (pH=7.4).

Phospholipid Analysis. Identification and quantification of phospholipids in the MFGM extract and liposomes were performed using a nuclear magnetic resonance (NMR) spectrometer (Bruker Avance III HD 500 NMR spectrometer). In short, a detergent solution containing 10% (w/w) sodium cholate and 1% (w/w) EDTA was prepared in a 20% (v/v) deuterium oxide aqueous solution. The pH of the detergent solution was then adjusted to 7.1 using a 1 M NaOH solution. An aliquot of each sample (~30 mg) was dispersed in 750 μL of the detergent solution, and 50 μL of $K_2HPO_4$ solution (6 mg/mL) was added as an internal standard for the quantification of phospholipids. Then, the samples were sonicated at 60° C. for 10 minutes with occasional mixing by vortex. Proton-decoupled $^{31}P$ NMR spectra were collected at 202.3 MHz with 128 scans using a 2.0 sec recycle delay and 81.5 kHz spectral width. TopSpin 3.5 and MestRenova 14.1 were used to record and analyze the spectra, respectively. The phospholipids were quantified by relating the area of each signal peak to the area of the internal standard of known molar concentration.

Heat Treatment. Both MFGM and SFPC liposomes were subjected to heat treatment at three different temperatures (60, 75, and 90° C.) for 30 minutes by immersing them in a constant temperature water bath. Post heat-treatment, all samples were subjected for morphological characterization by CLSM. Their EE %, diameter, and ζ-potential values were also measured as well for comparative analysis.

Characterization Of Synthesized Liposomes. For all liposomes, characterization was conducted before and after heat treatment. Morphological characterization was carried out using a Zeiss LSM 710 confocal laser scanning microscope (CLSM) equipped with a 63× oil-phase objective lens. Samples were prepared for microscopy using Nile red (a lipophilic dye) to stain the phospholipid bilayer and make the liposomes visible. An aliquot of liposomal dispersion (1 mL) was mixed with 10 μL of Nile red solution (0.2 wt. % in ethanol), followed by mild agitation by hand. In the CLSM, the fluorescence emission of Nile Red was recorded at 558-635 nm.

The ζ-potential, diameter, and size distribution of liposomes were determined using a 90 PLUS particle size analyzer (Brookhaven Instruments Corporation, Holtsville, NY, USA) equipped with BI-ζ extension. For measurement, the liposome suspension was diluted 30 times in TRIS buffer to avoid light scattering.

Encapsulation Efficiency (EE). The protamine aggregation method was used to measure the encapsulation efficiency (EE) of vitamin C by the liposomes. Aliquots of liposomal dispersion (0.1 mL) were mixed with an equal volume of protamine sulfate solution (10 mg/mL) to help flocculate the liposomes and were incubated for 5 minutes. The mixture was then diluted with saline solution (0.9% w/v), chilled to 4° C., and centrifuged for 25 minutes at 2000×g. The supernatant was decanted, leaving behind the concentrated liposomes. For both fractions, the liposomes were then ruptured by the addition of 200 μL of 10% w/v Triton X-100 solution and agitating for 5 minutes by vortex, releasing vitamin C into solution. The concentration of vitamin C was then determined by measuring absorbance at 265 nm using a UV/Vis spectrophotometer (UV1900, Shimadzu Scientific Instruments, Marlborough, MA, USA).

The EE of vitamin E was measured by the following method. 1.5 mL of liposomal dispersion was centrifuged at 4° C. for 20 minutes at 1000×g, and the supernatant was separated from the concentrated liposomes. For both fractions, 0.2 mL DMSO was added to solubilize both the phospholipids and vitamin E liposomes, making homogeneous solutions. The solutions were then diluted to a final volume of 3 mL with additional TRIS buffer and the absorbance at 295 nm was measured using a UV/Vis Spectrophotometer. The EE of vitamin E and C were calculated using equation 2, where VC is the vitamin content:

$$EE\ (\%) = \frac{VC \text{ in centrifuged liposomes}}{VC \text{ in centrifuged liposomes} + VC \text{ in supernatant}} \times 100 \qquad [2]$$

Storage Stability of MFGM Liposomes. The storage stability of MFGM liposomes was evaluated by their ability to retain encapsulated bioactives after storage as measured by their EE. To this end, the EE of liposomal dispersions in TRIS buffer were measured before and after storage for 4 weeks at 4° C. The storage stability was reported as a percent of the original encapsulation efficiency.

Statistical Analysis. The EE %, diameter, and ζ-potential values of the synthesized liposomes were reported as mean±standard deviation, and all treatments were performed triplicate for each sample. Statistical analysis was performed in R (Version 3.6.3., R Foundation for Statistical Computing, Vienna, Austria). One-way ANOVA with Tukey's honestly significant difference test with a 95% confidence interval was conducted to determine the statistical significance of differences in means.

Figure 7A:
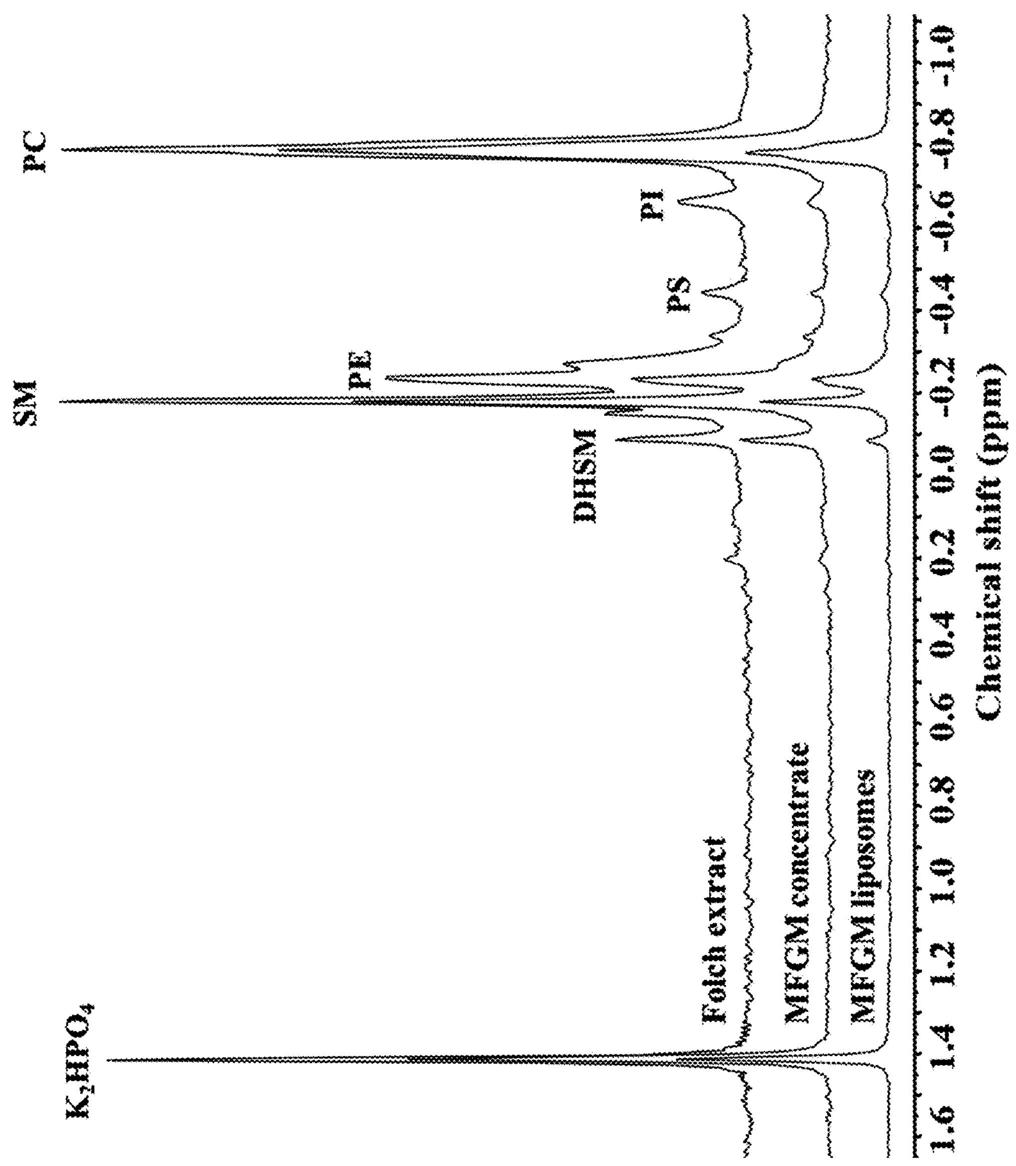
FIGS. 7A-7B show (FIG. 7A) Phosphorus-31 nuclear magnetic resonance ($^{31}P$ NMR) spectra and (FIG. 7B) phospholipid composition of a Folch extract, a MFGM phospholipid concentrate, and MFGM liposomes. Lower-case labels indicate statistically significant differences ($p<0.05$). DHSM=dihydrosphingomyelin, SM=sphingomyelin, PE=phosphatidylethanolamine, PS=phosphatidylserine, PI=phosphatidylinositol, PC=phosphatidylcholine.

The isolation and fractionation of MFGM phospholipids from buttermilk powder was carried out utilizing a "green" sequential pure SC-$CO_2$ and ethanol-modified SC-$CO_2$ extraction under the following extraction conditions: pressure (30 and 40 MPa), temperature (50 and 60° C.), and ethanol concentration (10, 15, and 20%). These optimized extraction conditions were implemented for the highest phospholipid recovery in this work. The total lipid content of buttermilk powder was 9% as determined by Folch extraction, where 60% of the total lipids were phospholipids. Similar findings have previously been reported. In this current example, nonpolar lipids were first extracted from buttermilk powder using pure SC-$CO_2$, and the polar lipids (i.e. phospholipids) were concentrated in the $2^{nd}$ fraction by extraction with ethanol-modified SC-$CO_2$ under previously optimized extraction conditions. The phospholipid contents of the extracts and liposomes were determined using $^{31}P$ NMR (FIGS. 2A-2B). Dihydrosphingomyelin (DHSM), SM, PE, PS, PI, and PC were the major phospholipids in the samples with $^{31}P$ NMR signals at δ −0.09 ppm, δ −0.18 ppm, δ −0.23 ppm, δ −0.44 ppm, δ −0.66 ppm, and δ −0.79 ppm, respectively (FIG. 7A). Similar chemical shifts have been previously reported. The total lipid yield of the $1^{st}$ fraction was 2.3±0.2% (w/w), very little of which was phospholipids (0.21±0.03%, w/w) due to nonpolar structure of SC-$CO_2$. On the other hand, the ethanol-modified SC-$CO_2$ extraction ($2^{nd}$ fraction) had a lipid yield of 4.7±0.2% (w/w) and a phospholipid content of 75±2% (w/w) (hereafter this fraction is referred as the MFGM phospholipid concentrate). This procedure produces the highest MFGM phospholipid purity reported so far from buttermilk powder. Overall, 78% of the total lipids and 66% of the MFGM phospholipids present in the buttermilk powder were recovered using this sequential SC-$CO_2$ extraction.

For comparison, a previous study attained phospholipid purity of 56% from spray-dried 50 kDa retentate of buttermilk using ethanol-modified SC-$CO_2$ extraction. However, the buttermilk was subjected to enzymatic hydrolysis, ultrafiltration, and spray drying prior to a very long SC-$CO_2$ extraction (13 h), adding processing time. Similarly, a commercial phospholipid concentrate (PC 700) from bovine milk produced by Fonterra Co-operative Group Limited (Rosemont, IL) had a lower phospholipid content (59%). The production steps of PC 700 are a trade secret and cannot be evaluated, but PC 700 contains a fair amount of lactose (6.6%) which limits its potential applications.

Figure 7B:
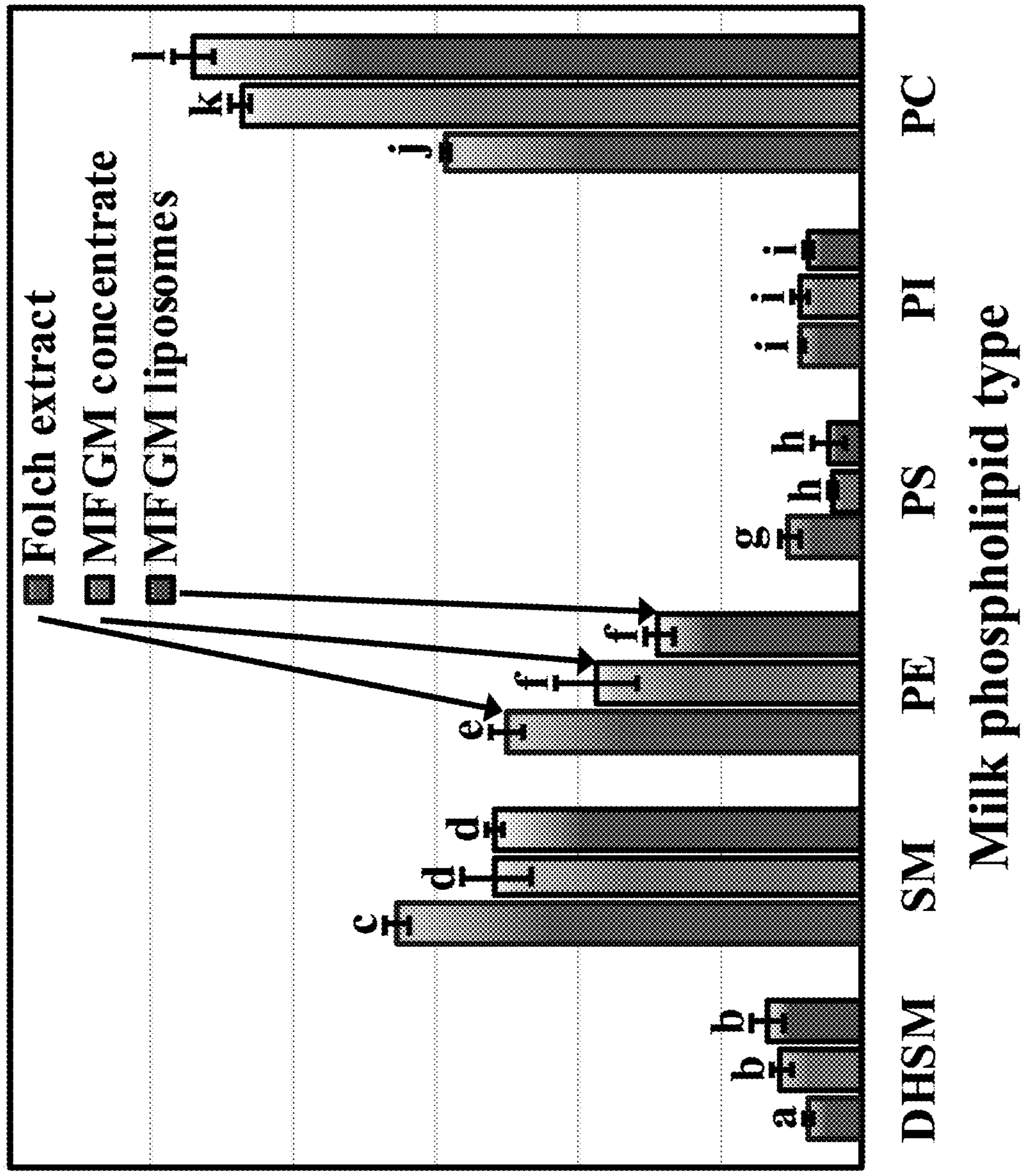

The phospholipid composition of the buttermilk powder used in this example was 3.7% DHSM, 32.7% SM, 25.0% PE, 5.1% PS, 4.2% PI, and 29.3% PC as determined by Folch extraction (FIG. 7B), which agrees with previously reported values. The MFGM phospholipid concentrate had a significantly different phospholipid composition: 6.7% DHSM, 25.8% SM, 18.7% PE, 2.0% PS, 4.3% PI, and 43.7% PC (FIG. 7B). The changes in phospholipid composition can mostly be attributed to the higher solubility of PC in ethanol-modified SC-$CO_2$ as compared to the other phospholipids, resulting in an increased percentage of PC in the MFGM phospholipid concentrate (44% PC) in comparison to the Folch extract (29% PC) (FIG. 7B).

Liposomes were synthesized with the MFGM phospholipid concentrate as well as SFPC for comparison. The ability of these liposomes to encapsulate bioactives was determined using vitamins E and C as model hydrophobic and hydrophilic micronutrients, respectively. Liposome synthesis was carried out by using the Vent-RESS system utilizing SC-$CO_2$ as a solvent as explained herein.

For a majority of the phospholipids (DHSM, SM, PE, PS, and PI), no significant difference in composition was measured between the initial MFGM phospholipid concentrate and the synthesized liposomes. However, the MFGM liposomes did contain a slightly higher PC content (44 vs. 47%) which can be attributed to its solubility in SC-$CO_2$ and the matrix effect (FIG. 7B).

Figure 8B:
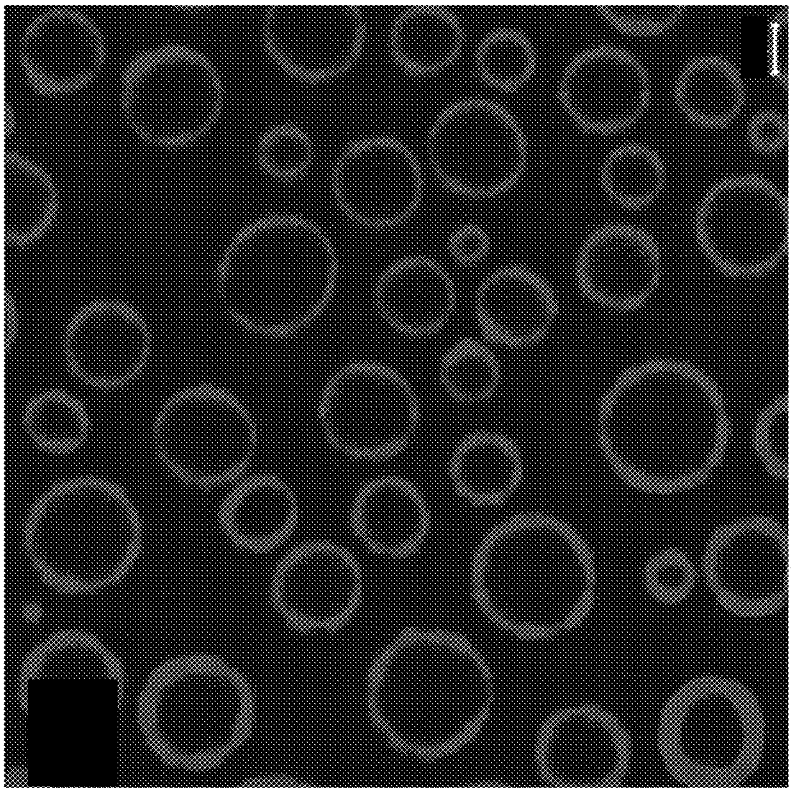
FIGS. 8A-8D show confocal laser scanning microscopy (CLSM) images of MFGM liposomes (FIG. 8A) before and after heat-treatment at (FIG. 8B) 60, (FIG. 8C) 75, and (FIG. 8D) 90 degrees Celsius (° C.) for 30 minutes (min.). All scale bars=2 microns (μm).
Figure 8A:
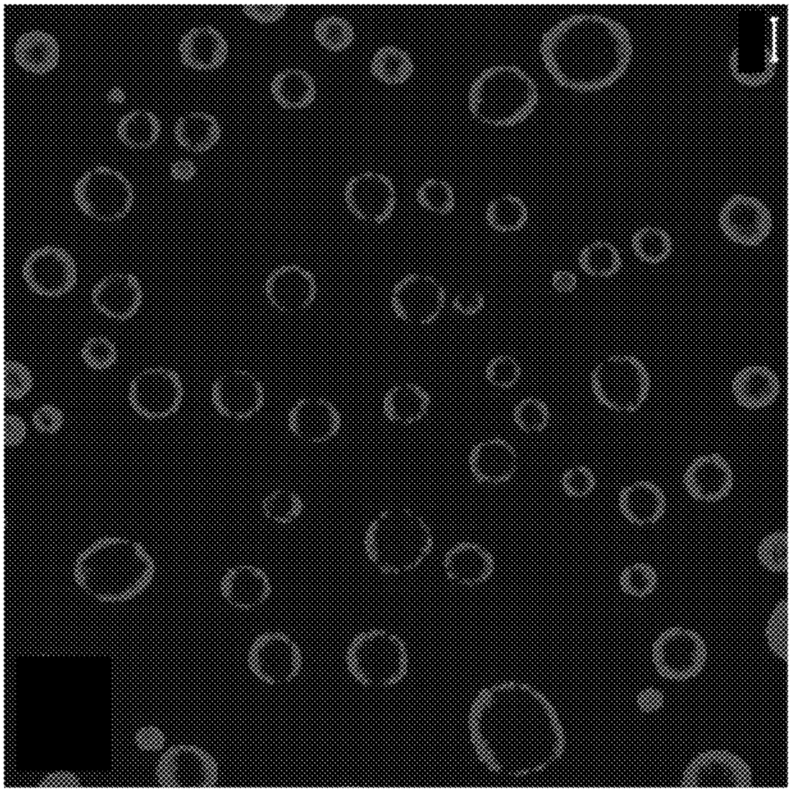
Figure 10B:
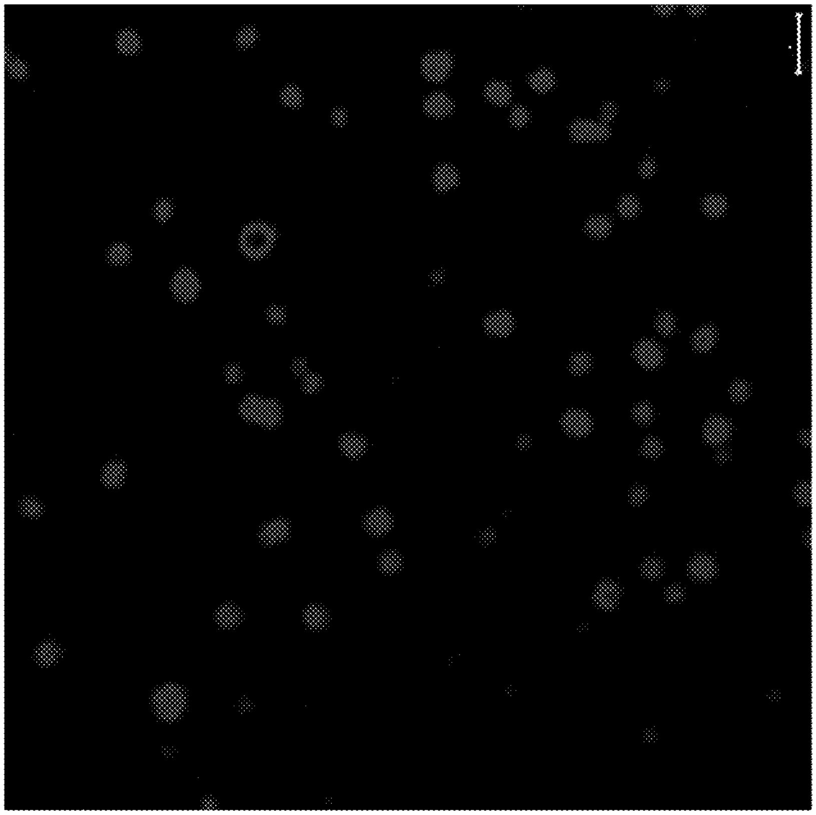
FIGS. 10A-10B show CLSM images of SFPC liposomes (FIG. 10A) before and (FIG. 10B) after heat-treatment at 60° C. for 30 minutes.
Figure 10A:
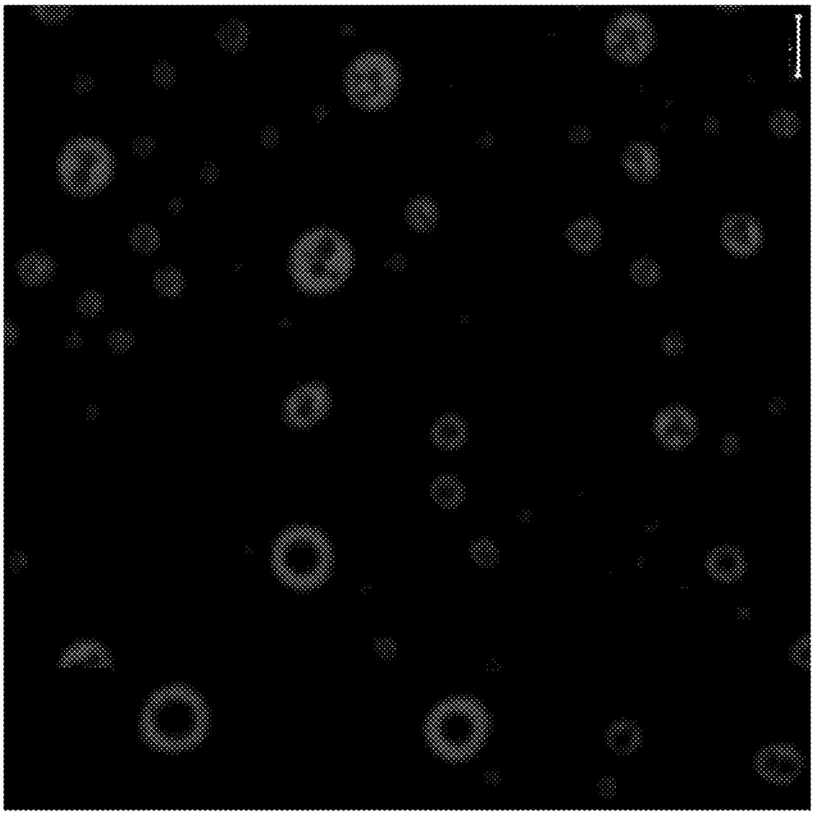

The CLSM images of liposomes made using MFGM phospholipids are shown in FIG. 8A. The lipophilic dye Nile red fluoresced bright red, revealing the phospholipid bilayer. Liposomes synthesized from MFGM phospholipids mostly produced ULV-type morphology; with an average diameter of 532±68 nm and ζ-potential of −57.5±0.3 mV (FIGS. 9A(1) and 9C(1)). In contrast, SFPC based liposomes produced a mixture of ULV, MLV, and MVV morphologies (FIG. 10A). While the distinct layers of MLV-type liposomes could not be observed in the micrographs, some of the synthesized liposomes had significantly thicker walls than the more common ULVs, indicative of MLV-type liposomes. Due to their higher proportion of phospholipids, MLVs and MVVs are better equipped to encapsulate fat-soluble compounds whereas ULVs are more suitable to encapsulate water-soluble compounds. The SFPC liposomes had an average diameter of 761±94 nm and ζ-potential of −36.5±1.4 mV (FIGS. 9A(2) and 9C(2), respectively). For both MFGM and SFPC liposomes, unimodal diameter distribution was observed as shown in FIGS. 9B(1) and 9B(2), respectively. Both MFGM and SFPC liposomes were able to form stable dispersions since the magnitude of their ζ-potentials were greater than 30 mV for both systems (FIGS. 9C(1) and 9C (2)). However, the MFGM liposomes had 57% higher surface charge than their SFPC counterparts. One possible explanation for this could be that in SFPC liposomes, negative surface charge is solely contributed by zwitterionic choline headgroups. In contrast, the MFGM liposomes have negatively charged anionic phospholipids (PS and PI) in addition to the zwitterionic phospholipids (PC, SM, DHSM, and PE). This is in line with previous studies, which reported a ζ-potential of −60 mV at pH 7 for MFGM phospholipids.

Figure 8D:
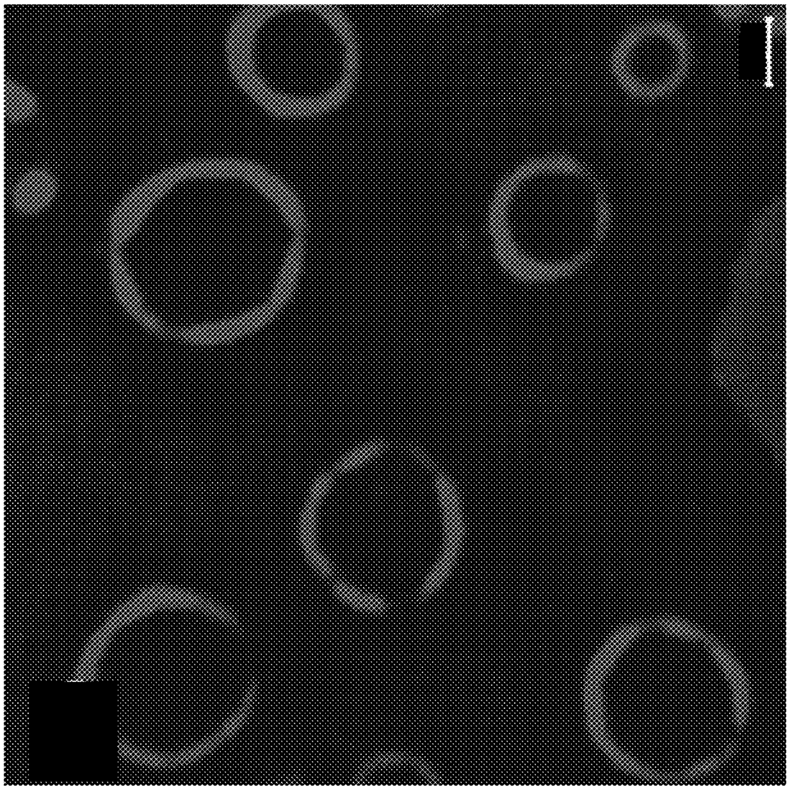
Figure 8C:
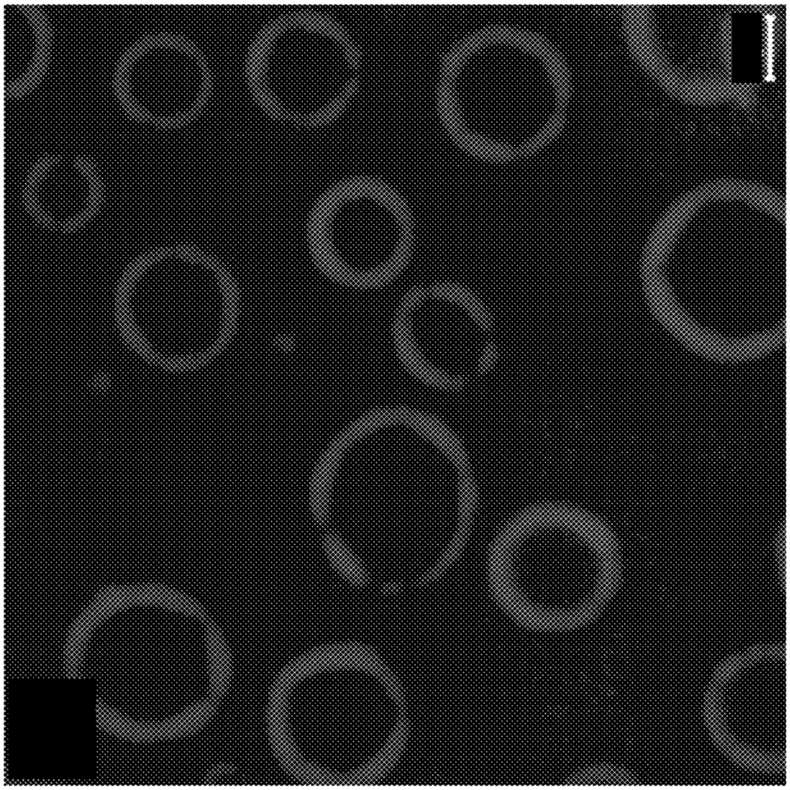

The CLSM micrographs of MFGM liposomes before and after 30 minutes of heat treatment at three different temperature levels (60, 75, and 90° C.) are shown in FIGS. 8B-8D, respectively. No significant change ($p>0.05$) in liposomal diameter was observed after heating at 60° C. for 30 minutes. However, when heated at 75 and 90° C., the diameter of MFGM liposomes significantly increased ($p<0.05$) by factors of 1.6 and 2.0 respectively. This increase in diameter can be attributed to osmotic swelling of the aqueous core enabled by the increased permeability of the phospholipid bilayer at elevated temperatures. Increasing the thermal energy of the system enhances the mobility of phospholipids in the bilayer, resulting in changes in the orientation and packing of phospholipid molecules, ultimately increasing the permeability of the membrane. Since the aqueous core of the liposomes are solutions of vitamin C in TRIS buffer, they have a higher osmotic pressure than the collection buffer, resulting in the migration of water to the core and liposome swelling. Another possible explanation for increase in liposomal diameter could be that at higher temperatures liposome coalesced because inter-particle collisions had enough energy to overcome the electrostatic barrier between liposomes. For SFPC liposomes, heat treatment resulted in significant disruption of the liposomal structure. FIGS. 10A-10B juxtaposes the liposomes before treatment (FIG. 10A) and the fat droplets and remnant liposomes after heat treatment at 60° C. for 30 minutes (FIG. 10B). Heating at a temperature above 60° C. resulted in the complete disintegration of liposomal structures yielding lipid droplets with irregular shape under CLSM (data not shown). Therefore, for SFPC, only the properties of untreated and 60° C. heat treatment liposomes are reported.

Figure 11A:
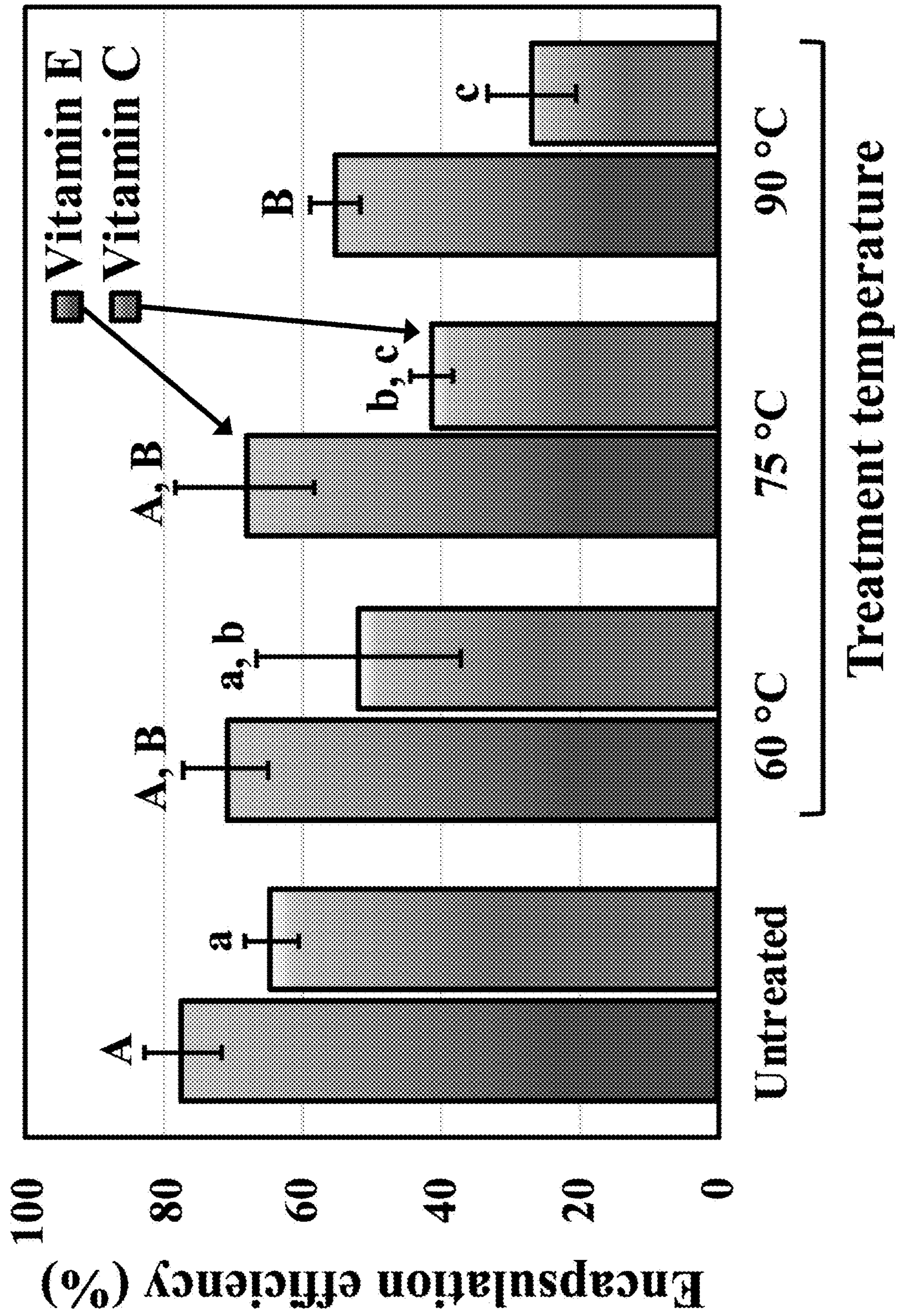
FIGS. 11A-11B show encapsulation efficiencies (EEs) of vitamins E and C in (FIG. 11A) MFGM liposomes and (FIG. 11B) SFPC liposomes before and after heat treatment for 30 minutes. Upper- and lower-case letters label statistically significant differences in the EEs of Vitamin E and Vitamin C, respectively ($p<0.05$).

The encapsulation efficiency of vitamins E and C in MFGM liposomes before and after heat-treatment at 60, 75, and 90° C. for 30 minutes are shown in FIG. 11A. For untreated MFGM liposomes, the EE of vitamins E and C were 77±5% and 65±4%, respectively. For vitamin E, the EE held constant ($p>0.05$) after heating to 60 or 75° C., but decreased significantly ($p<0.05$) for the 90° C. treatment (65±4%). For vitamin C, the EE held constant at 60° C., but decreased significantly after heat treatment at 75 and 90° C. (42±3% and 27±6%, respectively). Several factors could have played a role in the reduced EE at higher temperatures: (i) At higher temperatures, some of the MFGM liposomes could undergo structural disintegration, releasing bioactives. (ii) Due to the osmotic swelling of liposomes at higher temperatures the concentration of encapsulated micronutrients got diluted and subsequently lower EE was observed. Moreover, vitamin C is thermolabile—it could have been oxidized to dehydroascorbic acid then hydrolyzed to 2,3-diketogulonic acid during the heat treatment. This effect is expected to increase the EE of vitamin C since degradation of the unencapsulated vitamin C occurs at higher rates than that of vitamin C within the liposomes. However, the leakage and osmotic swelling effects were more dominant than the degradation effect, leading to an increase in the vitamin C content in supernatant (equation 2), and in turn decreasing the EE of vitamin C.

Figure 11B:
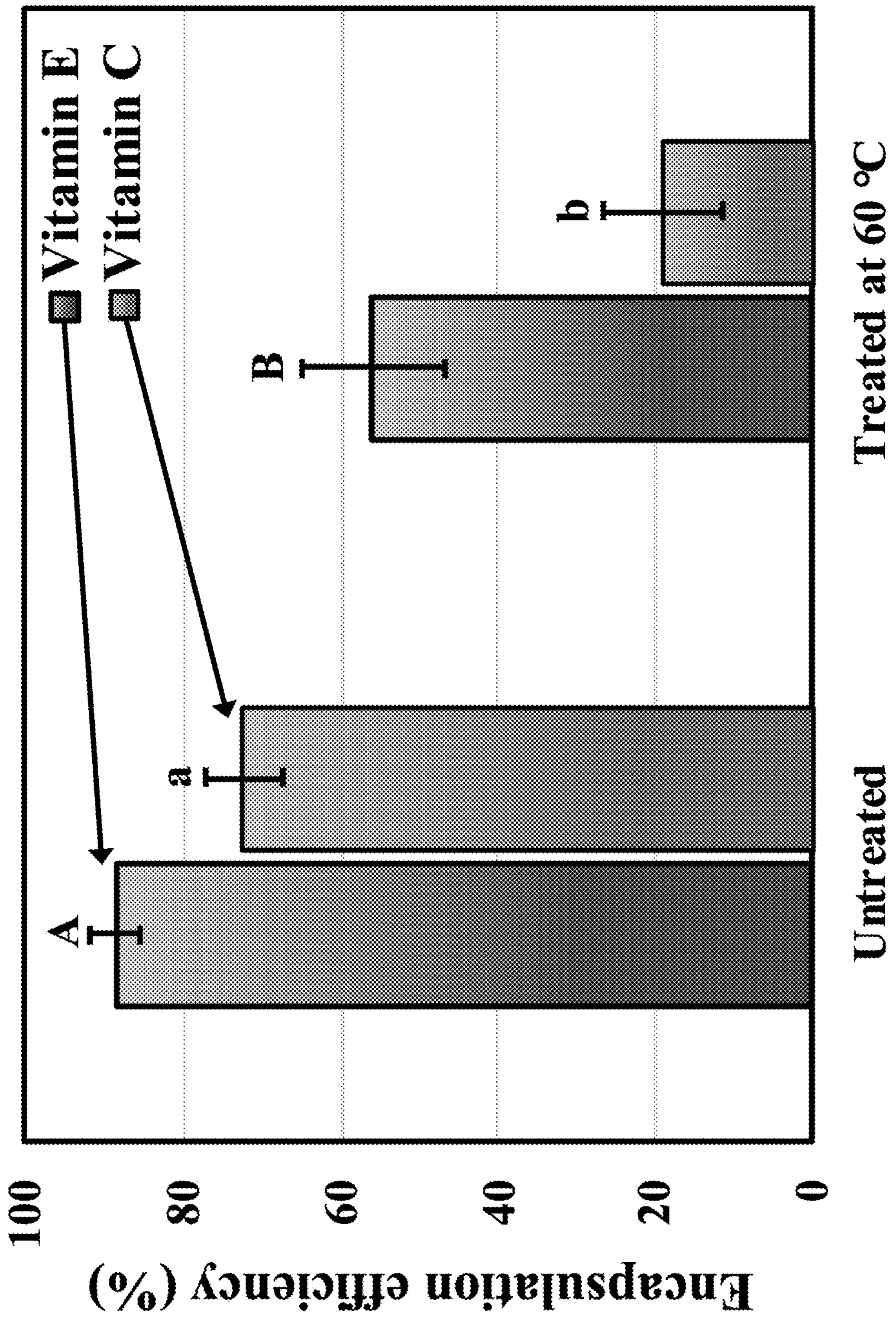

Untreated SFPC liposomes demonstrated an EE of 89±3% for vitamin E and 72±5% for vitamin C. While these initial EE values for SPFC were slightly better than for MFGM, they dropped significantly to 56±9% and 19±7%, respectively ($p<0.05$) after heat treatment as a result of structural disintegration (FIG. 11B). These EE values for SFPC liposomes agree with those from previous works.

The encapsulation efficiencies of MFGM liposomes reported in this example (77% hydrophobic, 65% hydrophilic) are on par with previously published liposomes. In a previous study, the encapsulation of curcumin (a hydrophobic bioactive) in liposomes made from MFGM (29% lipids extracted from buffalo milk) was compared to liposomes made from soybean lecithin. Under optimized conditions, the EEs for curcumin were 74 and 63%, respectively. MFGM's higher EEs were attributed to the presence of more suitable phospholipid structures and composition for liposomal entrapment of curcumin. One previous study used a high-pressure homogenization process to synthesize liposomes from a MFGM extract (59.2% phospholipids) and observed a maximum EE of 26% for vitamin C. Another study used liposomes prepared from MFGM (72-74% phospholipids) to encapsulate (3-carotene and potassium chromate as model hydrophobic and hydrophilic compounds, respectively. They measured an EE ca. 45% for f3-carotene when ethanol was used to combine (3-carotene with phospholipids prior to liposome synthesis by thin-film hydration (TFH). For potassium chromate, a maximum EE ca. 60% was reported. While the EE of the liposomes produced in this example generally compare favorably with that of other published works, a direct comparison would be unrealistic; there are too many differences between methods. There were different sources, compositions, and purities of MFGM phospholipids, a wide variation in operational parameters and techniques, varying use of solvents for dissolution of lipophilic cargo, and several different bioactives used to quantify encapsulation efficiency.

Figure 12:
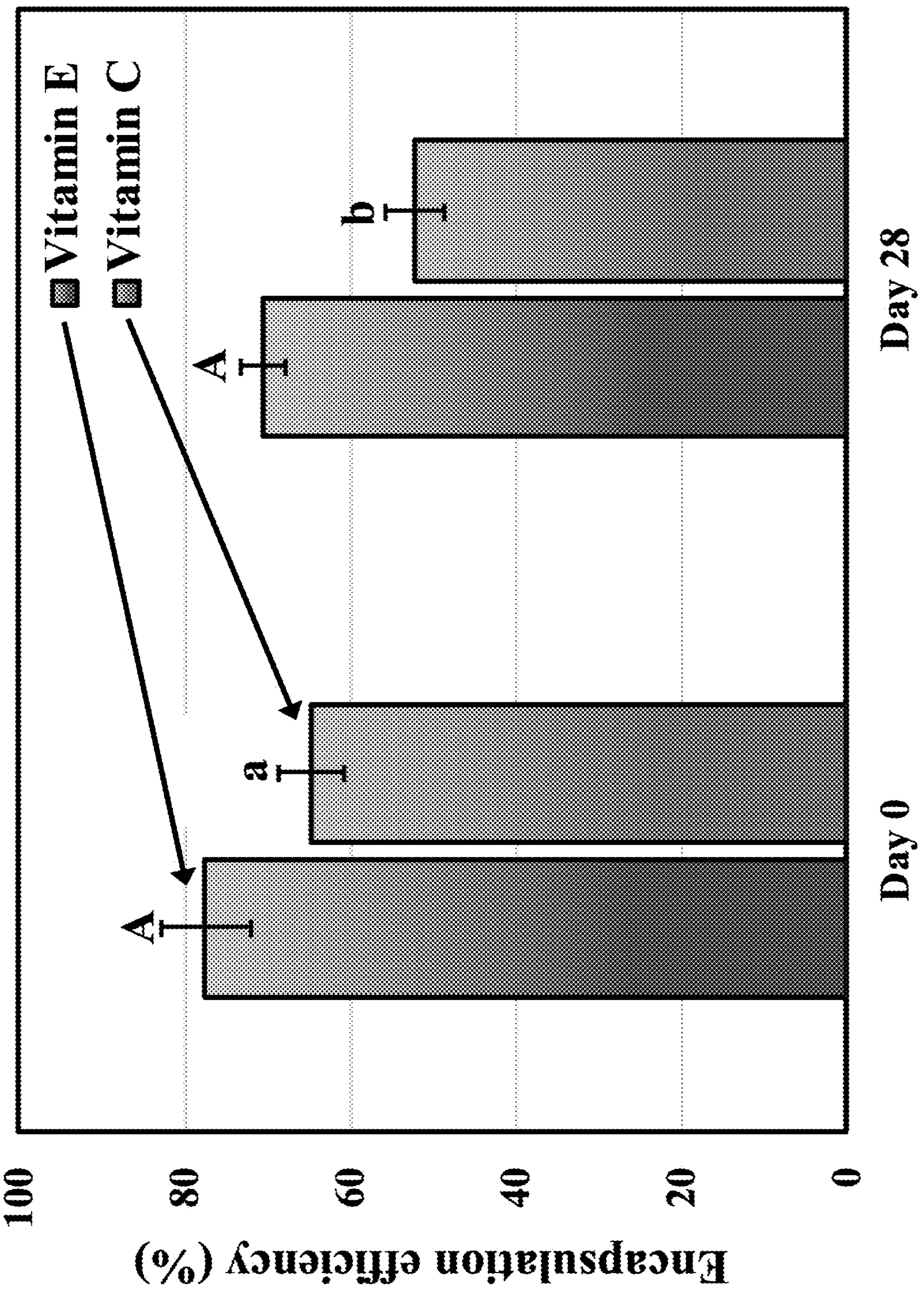
FIG. 12 shows EEs of vitamins E and C in MFGM liposomes on day 0 and day 28 of storage at 4° C. Upper- and lower-case letters label statistically significant differences in the EEs of vitamins E and C, respectively ($p<0.05$).

While the measured EE of vitamin E in MFGM liposomes disclosed herein decreased to 71±3% after storing the dispersion at 4° C. for 4 weeks, the change was not statistically significant ($p>0.05$). During storage, the retention of vitamin C in the MFGM liposomes decreased by 19%, which could have potentially been caused by the leakage of aqueous cargo over time (FIG. 12).

The structural endurance of a liposome is solely dependent on its phospholipid bilayer. The bilayer is considered to be in a stable, ordered formation when the hydrocarbon chains are fully extended and aligned in parallel. However, heat treatment adds energy to de-align molecules, adding "kinks" to the hydrocarbon chains, reducing packing efficiency and increasing membrane fluidity. The ordered gel formation transforms into a disordered liquid crystalline state, enabling degradation of the liposomal structure. Therefore, liposomes made of phospholipids with a higher phase transition temperature ($T_m$) would be able to withstand treatment at elevated temperature without having any structural disintegration. The heat stability of MFGM liposomes can be attributed towards the presence of saturated phospholipids with high $T_m$ (i.e. dipalmitoylphosphatidylcholine, palmitoylphosphatidylethanolamine, and SM). The SM family of phospholipids contains several long chain saturated fatty acids (C24:0, C23:0, C22:0, C18:0, and C16:0). These fatty acids lead to the unique biophysical properties of the MFGM which include a high $T_m$ (~34.3° C.) and better interaction with cholesterol and tocopherol, which enable the formation of an ordered domain. Furthermore, the addition of polycyclic amphiphilic molecules like cholesterol which possess a high $T_m$ (~147-149° C.) contributes to the heat stability of MFGM liposomes. These molecules promote the formation of a liquid ordered phase, an intermediate state between liquid crystalline and gel phases which doesn't evolve as a function of temperature.

In contrast, SFPC liposomes are made up of only one type of phosphatidylcholine (i.e. 1-oleoyl-2-linoleoyl-sn-glycero-3-phosphocholine) which has a $T_m$ below −4° C. due to a higher degree of unsaturation. Even though the PC liposomes made in this example gain structural integrity by the addition of cholesterol and vitamin E, it is not enough to prevent degradation upon heat treatment. Previous research studied the effect of autoclaving (121° C., 15 minutes) on the degradation and leakage from SFPC liposomes encapsulating several model hydrophilic and hydrophobic compounds. Liposomes from saturated phospholipids (i.e. palmitoylphosphatidylcholine (DPPC), dipalmitoylphosphatidylglycerol (DPPG)) and cholesterol were synthesized using thin-film hydration. Autoclaving these liposomes resulted in a 39±4% degradation of the model lipophilic N-trifluroacetyldoxorubicin-14-valerate. After autoclaving, ca. 20±5% leakage and 26±8% degradation of hydrophilic model compound calcein was observed. Hybrid liposomes (HBLs) have been reported, developed from soybean phospholipids (71% PC and 10% PE) and amphiphilic chitosan by TFH and dynamic high-pressure microfluidization. Curcumin was encapsulated as a model hydrophobic bioactive in the synthesized HBLs and measured an EE of 8.08±0.18%. The heat stability of HBLs autoclaved at 121° C. for 20 min in pure water and in PBS buffer was reported as no substantial change was observed in liposomal diameter, but the effect of heat treatment on the retention of curcumin was not discussed. However, both of these protocols are substantially laborious in addition to the use of toxic organic solvents, which are eliminated in our proposed approach.

A "green" sequential pure SC-$CO_2$ and ethanol-modified SC-$CO_2$ extraction was used to isolate and fractionate MFGM phospholipids from buttermilk powder. The final extract was composed of 75% phospholipids, the highest MFGM phospholipid purity reported so far from buttermilk powder. Phospholipid compositions were characterized by $^{31}P$ NMR spectroscopy. The phospholipid composition of this extract was found to be 5.6% DHSM, 25.8% SM, 18.7% PE, 2.0% PS, 4.3% PI, and 43.7% PC. The highly pure MFGM phospholipid concentrate was used to synthesize liposomes, which had a phospholipid composition of 6.7% DHSM, 25.8% SM, 14.3% PE, 2.4% PS, 3.9% PI, and 47.1% PC. The MFGM-based liposomes demonstrated ULV-morphology with an average diameter of 533 nm and a ζ-potential of −57 mV. In contrast, SFPC-based liposomes gave a mixture of ULV, MLV, and MVV morphologies, and had an average diameter of 761 nm and a ζ-potential of −37 mV. To evaluate the effectiveness of MFGM liposomes for bioactive encapsulation, vitamins E and C were used as model hydrophobic and hydrophilic bioactives; the encapsulation efficiencies were 77 and 65%, respectively. For comparison, SFPC-based liposomes had EEs of 88 and 72% for vitamins E and C. To determine heat stability, both MFGM and SFPC liposomes were heated to 60, 75, and 90° C. for 30 minutes. MFGM liposomes demonstrated enhanced heat stability as established by their CLSM images, structural characterization, and EE. Even after heating at 90° C. for 30 minutes, MFGM liposomes retained 65 and 27% of vitamin E and C, respectively. In contrast, SFPC liposomes disintegrated at the measured temperatures above 60° C. Disclosed herein is a synthesis method for heat-stable, multivitamin-loaded liposomes which is a green, sustainable, and novel technology amenable to industrial scale-up. This approach has potential use for effective bioactive delivery in pharmaceutical and food applications.

Example 3

The following is an example of milk fat globule membrane (MFGM) phospholipid extracts, methods of preparing and using MFGM phospholipid extracts, liposomes comprising MFGM phospholipid extracts, and methods of synthesizing and using liposomes comprising MFGM phospholipid extracts.

Heat-stable, multivitamin-loaded, and surface-coated liposomes tailored for pH-triggered delivery of both lipophilic and hydrophilic bioactives were synthesized from a cocktail of milk fat globule membrane (MFGM) phospholipids, supercritically extracted from buttermilk powder. Liposomes from MFGM-phospholipids (ML) were fabricated using a novel organic solvent free process based on venturi-based rapid expansion of a supercritical solution. A commercially available pH-responsive polymer, Eudragit® S100 was used to coat MLs (Eu-ML). Eu-MLs were heated to 60, 75, and 90° C. for 30 minutes and were observed to be heat-stable as established by CLSM images, structural characterizations, and encapsulation efficiency measurements. Coating of liposomes with Eudragit® S100 protected encapsulated payload from deleterious gastric environment and facilitated site-specific pH-triggered release in the simulated intestinal condition. This example established a green method to fabricate heat-stable liposomal vehicles for pH-triggered delivery of bioactive compounds with excellent potential for scale-up and applications in the food, pharmaceutical, and cosmetic industries.

Disclosed is a process for synthesizing liposomes, which involves the rapid expansion of a supercritical solution using a venturi-based system (Vent-RESS) for concomitant vacuum driven cargo loading, based on Bernoulli's principle. The effectiveness of this Vent-RESS system has been demonstrated to produce multivitamin loaded heat-stable liposomes synthesized from milk fat globule membrane (MFGM) phospholipids. MFGM contains a wide variety of phospholipids such as phosphatidylcholine (PC), phosphatidylethanolamine (PE), sphingomyelin (SM), phosphatidylserine (PS), and phosphatidylinositol (PI), which possess several beneficial health attributes. MFGM phospholipids' thermotropic nature enables emulsion stability of milk fat globules even when heated at elevated temperatures. MFGM liposomes (ML) demonstrated an improved resilience toward thermal processing and even after heating at 90° C. for 30 minutes, MLs retained their structural integrity and the incorporated payload. These heat-stable liposomal delivery system could potentially be used to increase the bioavailability of both lipophilic and hydrophilic bioactives through their simultaneous encapsulation. However, they are still not suitable for oral delivery applications owing to the susceptibility of liposome's phospholipid bilayer towards the combined adverse effects of acid hydrolysis and enzymatic degradation (i.e., phospholipases, pancreatic lipase, and cholesterol esterase) in the gastric environment. Several enteric polymers have been extensively used to coat the liposomal surface to protect the bilayer and encapsulated payload. In the gastric environment these materials act as a shell around the liposomal core to prevent their structural disintegration and premature release of encapsulated bioactives. However, in the higher pH condition of intestine the shell undergoes degradation, followed by the release of loaded bioactives. In this example, Eudragit® S100 was used to coat the liposomal surface. Eudragit® S100 is a polyanionic block co-polymer constituted by methyl methacrylate-methacrylic acid and is generally recognized as safe (GRAS). It is insoluble in acidic gastric pH and dissolves only above pH 7.0; thus, coating liposomes with this polymer would have the potential to protect them from the acidic condition in the gastrointestinal (GI) tract. Several studies have been conducted to coat liposomes with Eudragit® S100 to facilitate their pH triggered payload delivery in the intestine. The common methods of coating include electrostatic interaction between liposomal surface and the polymer or embedment of liposomes into polymer cluster through micelle-to-vesicle transition technique.

In this examples, the coating of bioactive loaded liposomes with an enteric material (e.g., Eudragit® 5100) is demonstrated through a modified solvent displacement method by using polyethylene glycol (PEG) as a non-toxic solvent. PEG is a non-immunogenic, uncharged linear polymer that is GRAS. Thus, it is hypothesized that the coating of liposomes with Eudragit® S100 will serve two purposes. The first one is protection of the payload until reaching the target site in the GI tract, followed by degradation of the outer membrane and site-specific release of the encapsulated bioactives. The second purpose is improved thermal stability; Eudragit® S100's high glass transition temperature (161-167° C.) will provide enhanced thermal stability to MFGM liposomes during processing at elevated temperature, especially for food applications.

Material and methods. Materials. Sunflower phosphatidylcholine (SFPC) (Sunlipion® 90, 99%), extracted from non-genetically modified sunflower lecithin was donated by Perimondo (Florida, NY, USA). The MFGM phospholipids were concentrated from buttermilk powder through a sequential pure SC-$CO_2$ (for nonpolar fraction) and ethanol-modified SC-$CO_2$ extraction (for polar fraction) method. From the extracted lipid and ethanol mixture, ethanol was removed and the phospholipid rich fraction was later used for liposome synthesis; the extraction procedure of MFGM phospholipids has been precisely explained in our previous publication (Ubeyitogullari & Rizvi, 2020). Carbon dioxide ($CO_2$) (99.99%) was purchased from Airgas (Ithaca, NY, USA). Calcein and Tris(hydroxylmethyl) aminomethane (TRIS) were purchased from Acros Organics (Morris, NJ, USA) and Bio-Rad (Hercules, CA, USA), respectively. Vitamin E (α-tocopherol, 95.5%), Nile Red, cholesterol (92.5%), and dimethyl sulfoxide (DMSO) (99.9%) were purchased from Sigma-Aldrich (St Louis, MO, USA). Vitamin C (L-ascorbic acid, 99%) was purchased from TCI America (Portland, OR, USA). Eudragit® S100 and polyethylene glycol 400NF (PEG-400) were donated by Evonik (Piscataway, NY, USA) and Dow Chemical Company (Midland, MI, USA), respectively.

Liposome synthesis. Bioactive loaded liposomes were synthesized from two different phospholipids (i) MFGM and (ii) SFPC phospholipids by the Vent-RESS system and they have been abbreviated as ML and SL, respectively. The operating protocol of Vent-RESS system has been precisely explained herein. To determine the effectiveness of bioactive encapsulation in the synthesized liposomes, vitamins E and C were used as a model lipophilic and hydrophilic bioactives. The lipophilic cargo was prepared by mixing the phospholipids, cholesterol, and vitamin Eat a weight ratio of 5:1:1. First phospholipids (i.e., MFGM or SFPC) were melted at 45° C. followed by addition of cholesterol and vitamin E with thorough mixing until a homogeneous blend was obtained. The mixture was then solidified at 4° C. for loading convenience. The hydrophilic cargo was prepared by mixing 0.125 M vitamin C in 10 mL of 0.02 M TRIS buffer solution (pH=7.4). The resulting liposomes were collected in 10 mL of TRIS buffer solution (pH=7.4).

Coating of liposomes with Eudragit® S100. To coat bioactive loaded liposomes with Eudragit® S100, polyethylene glycol (PEG) was used as a non-toxic solvent. Liposomes were coated with Eudragit through modification of a nanoprecipitation method which requires two solvents that are miscible with each other and a polymer that dissolves in one solvent and is insoluble in the other one (i.e., non-solvent). Nanoprecipitation occurs when the polymer solution is added to the non-solvent. PEG and 6-mM acetic acid-sodium acetate buffer (pH 4.5) were used as solvent and non-solvent, respectively. Eudragit® S100 is soluble in the PEG at low concentration and is insoluble in the acidic buffer. 50 mg of Eudragit® S100 was dissolved in 3 mL of PEG, followed by addition of 2 mL of concentrated liposomal dispersion. After thorough mixing, the resultant solution was added dropwise in the acetic acid-sodium acetate buffer (pH 4.5) (non-solvent) under magnetic stirring and was kept at 4° C. for 4 h. Eudragit coated liposomes were then concentrated by centrifugation and after being washed three times with the acetic acid-sodium acetate buffer (pH 4.5), were kept in the same buffer.

Heat treatment. Coated (i.e., Eu-ML and Eu-SL) and uncoated liposomes (ML and SL) were subjected to heat treatment at three different temperatures (60, 75, and 90° C.) for 30 minutes by immersing them in a temperature-controlled water bath. Post heat-treatment, samples were subjected for morphological characterization by confocal laser scanning microscopy (CLSM); their encapsulation efficiency (EE %), diameter, and ζ-potential values were measured as well for comparative analysis.

Liposomal characterization. CLSM was used to examine the morphology of coated and uncoated liposomal dispersions. Images were obtained by using a Zeiss LSM 710 confocal microscope equipped with a 63× oil-phase objective lens. Calcein and Nile red to stain the hydrophilic core and the lipophilic bilayer parts of the synthesized liposomes, respectively. Eudragit® S100's non-polar nature was exploited to visualize Nile red stained polymer coating on synthesized liposomes. The fluorescence emission spectra of Calcein and Nile red were set between 496-535 nm and 558-635 nm, respectively. Calcein was mixed with the citric acid-sodium citrate buffer (2 mg/mL) and was used as aqueous cargo. After preparing the liposomes, the phospholipid bilayer, with or without coating, was stained with Nile red. For this, Nile red was first dissolved in ethanol, then, 10 μL of Nile red solution in ethanol (0.2 w %) was added to 1 mL of calcein-loaded liposomes and mildly agitated by hand for 1 min and the stained liposome suspension was used for CL SM.

A 90 PLUS particle size analyzer equipped with BI-zeta extension was used to determine the diameter and zeta potential of both MLs and Eu-MLs. For the measurement, the liposomal suspension was diluted 10-fold with buffer.

Encapsulation efficiency (EE) measurement. To measure the EE of vitamin C in coated Eu-ML, 1.5 mL of coated-liposomal dispersion was centrifuged at 4° C. for 20 minutes at 2000×g, and the supernatant was separated from the concentrated liposomes. For both fractions, the liposomes were then ruptured by the addition of 200 μL of 10% w/v Triton X-100 solution and agitated for 5 minutes by vortex mixing which enables release of vitamin C into the solution. TRIS buffer was used to dilute the solution to a final volume of 3 mL. The concentration of vitamin C was then determined by measuring absorbance at 265 nm using a UV/Vis spectrophotometer (UV1900, Shimadzu Scientific Instruments, Marlborough, MA, USA).

For vitamin E, 1.5 mL of liposomal dispersion was centrifuged at 4° C. for 20 minutes at 2000×g, and the supernatant was decanted, leaving behind the concentrated liposomes. For both fractions, 0.2 mL DMSO was added to homogeneously solubilize Eudragit® S100, phospholipids, and vitamin E. The solution was then diluted to a final volume of 3 mL with additional TRIS buffer and the absorbance of vitamin E at 295 nm was measured using a UV/Vis Spectrophotometer. The EE of vitamin E and C were calculated using equation [1]:

$$EE \text{ for vitamin } C \text{ and } E\ (\%) = \frac{\text{(Vitamin content in concentrated coated or uncoated liposomes)}}{\text{(Vitamin content in concentrated coated or uncoated liposomes + Vitamin content in supernatant)}} \times 100. \quad [1]$$

Evaluation of core release under simulated gastrointestinal conditions. The stability of both MLs and Eu-MLs under simulated gastrointestinal conditions was evaluated. First, 5 mL of coated or uncoated liposomal dispersion was added to 25 mL of 20 mM phosphate buffer solution at pH 6.8. The pH of the solution was then adjusted to 2 by adding a 1 M hydrochloric acid solution. 1 mL of porcine pepsin (0.8 w % solution) from porcine gastric mucosa was added to it. The resultant solution in a closed container was placed in a shaking water bath at 200 rpm, and temperature was maintained at 37° C. At predetermined incubation times (i.e., 0, 15, 30, 60, 90, and 120 min), samples were collected for analysis followed by centrifugation at 10,000×g for 30 min; to measure vitamin E content collected sample was passed through an ultrafiltration membrane (100 kDa MW cutoff). After 2 h treatment under simulated gastric conditions, the pH of the solution was adjusted to 5.3 by using a 25 mM sodium bicarbonate solution. A 1.5 mL multi-enzyme solution prepared in 20 mM phosphate buffer containing 0.2 mg lipase, 0.4 mg pancreatin from porcine pancreas, and 2.4 mg bile extract from porcine solution was added to it. The final pH of the solution was maintained at 7.2 by using a 1 M NaOH solution. The sample was again placed in a shaking water bath at 200 rpm at 37° C. and at predetermined incubation times (i.e., 120, 150, 180, 210, 240, 300, and 360 min) samples were collected for analysis followed by centrifugation at 10,000×g for 30 min. The concentration of released cargo was determined by using UV/Vis spectrophotometry for both vitamins. The amount of released cargo was represented as a percentage of the total cargo released from coated or uncoated liposomes, where the minimum and the maximum concentrations have been normalized to 0 and 100%, respectively.

Bioactive release kinetics from coated liposomes. A thorough understanding of the release kinetics of bioactives from the coated liposomes is necessary to optimize their application as potential bioactive delivery vehicles. The release of vitamins C and E from Eu-MLs was first modeled by the Higuchi equation:

$$\frac{M_t}{M_\infty} = k_H\sqrt{t}, \qquad [2]$$

where $M_t$ is amount of bioactive released at time t, $M_\infty$ represents amount of bioactive released at infinite time, and $k_H$ is the Higuchi constant. Based on Eq. 2 Korsmeyer Peppas developed their model (the Korsmeyer Peppas equation):

$$\frac{M_t}{M_\infty} = k_{KP}xt^n, \qquad [3]$$

where $k_{KP}$ is the Korsmeyer Peppas constant, which incorporates the geometrical and structural characteristics of bioactive loaded vesicles, and where n represents the release exponent. The value of n varies between 0.5-1 depending on whether the release of bioactive follows pure Fickian or non-Fickian types of transport. Thus, to study the effect of non-Fickian diffusion during release of vitamin C and E from Eu-MLs, the Sahlin Peppas model was used (the Sahlin Peppas equation):

$$\frac{M_t}{M_\infty} = k_{SP1}t^n + k_{SP2}t^{2n}, \qquad [4]$$

where $k_{SP1}$ and $k_{SP2}$ are diffusion constants related to Fickian and non-Fickian types of release kinetics, respectively. To elucidate whether there is a change in surface area or diameter of coated liposomal vesicles that is dictating the bioactive release profile, the Hixon Crowell Model (the Hixson Crowell equation):

$$M_0^{1/3} - M_t^{\frac{1}{3}} = K_{HC}t, \qquad [5]$$

where $M_0$ is the initial amount of bioactive, $M_t$ is the amount of bioactive remaining at time t, $K_{HC}$ is the Hixson-Crowell constant, and t is time. Simpler zeroth (Eq. 6) and first order (Eq. 7) reaction kinetics were used as well to elucidate the bioactive release behavior (the Zhou equation).

$$C_0 - C_t = K_0t, \qquad [6]$$

$$\log C = \log C_0 * -\frac{K_1t}{2.303}, \qquad [7]$$

where $C_0$ is the initial concentration at time 0, $C_t$ is the concentration at time t, $K_0$ is the zero-order rate constant. The fitness of a model was determined by using Eq. 8 which measures the absolute relative deviation (ARD) between the predicted amount of released-bioactive ($M_p$) and the experimentally obtained value of released-bioactive ($M_t$):

$$ARD\ \% = \frac{|M_t - M_0|}{M_t} \times 100. \qquad [8]$$

Statistical analysis. All the values were reported as mean±standard deviation, and all treatments and analyses were performed in triplicate for each sample. Statistical analysis was performed in R (Version 3.6.3., R Foundation for Statistical Computing, Vienna, Austria). One-way ANOVA with Tukey's honestly significant difference test with a 95% confidence interval was conducted to determine the statistical significance of differences in means.

Figure 13:
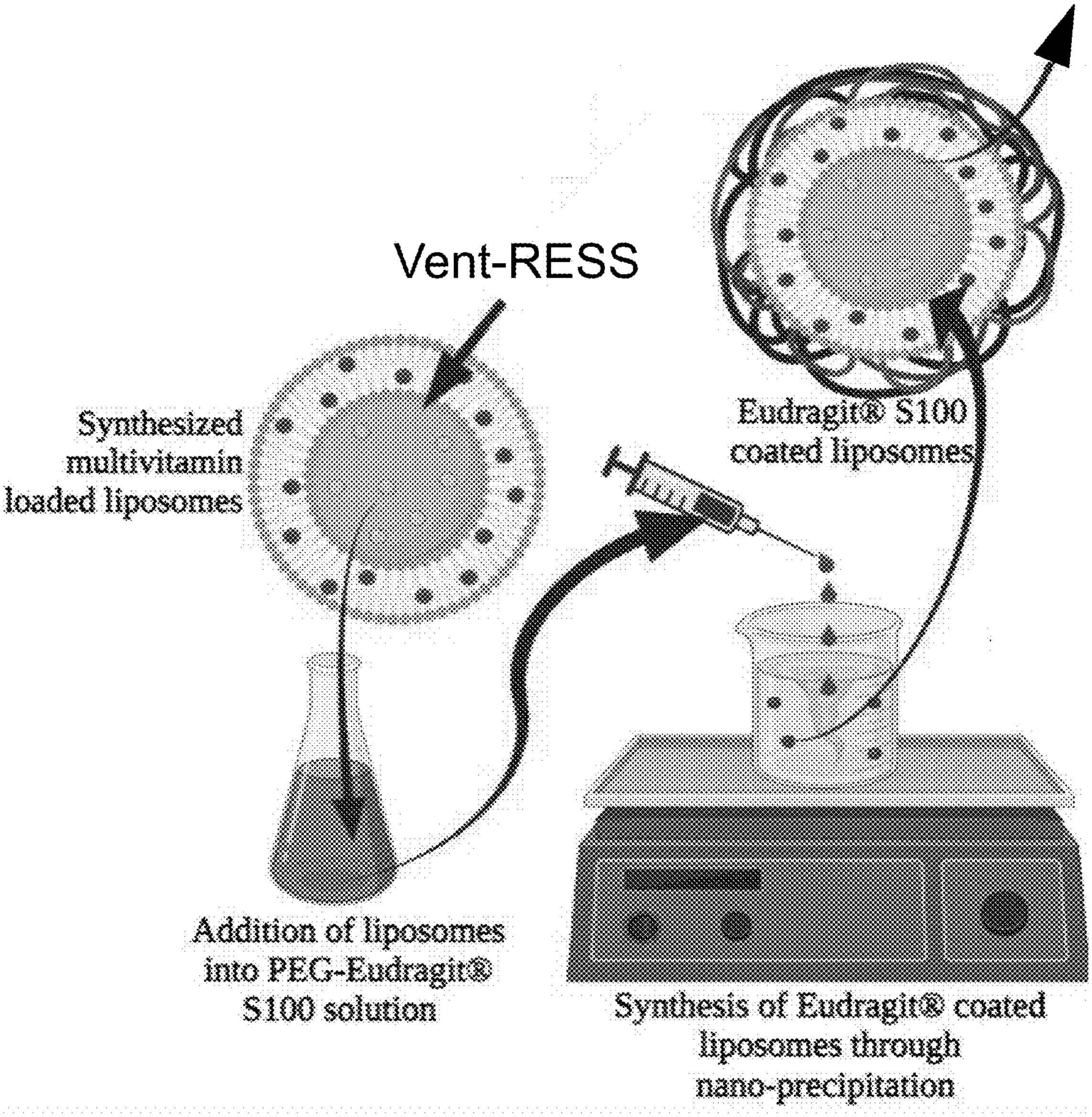
FIG. 13 shows an illustrative representation of liposomes synthesis from MFGM and SFPC-phospholipids, the coating of those liposomes with Eudragit® S100, and their fate in gastrointestinal tract.
Figure 13:
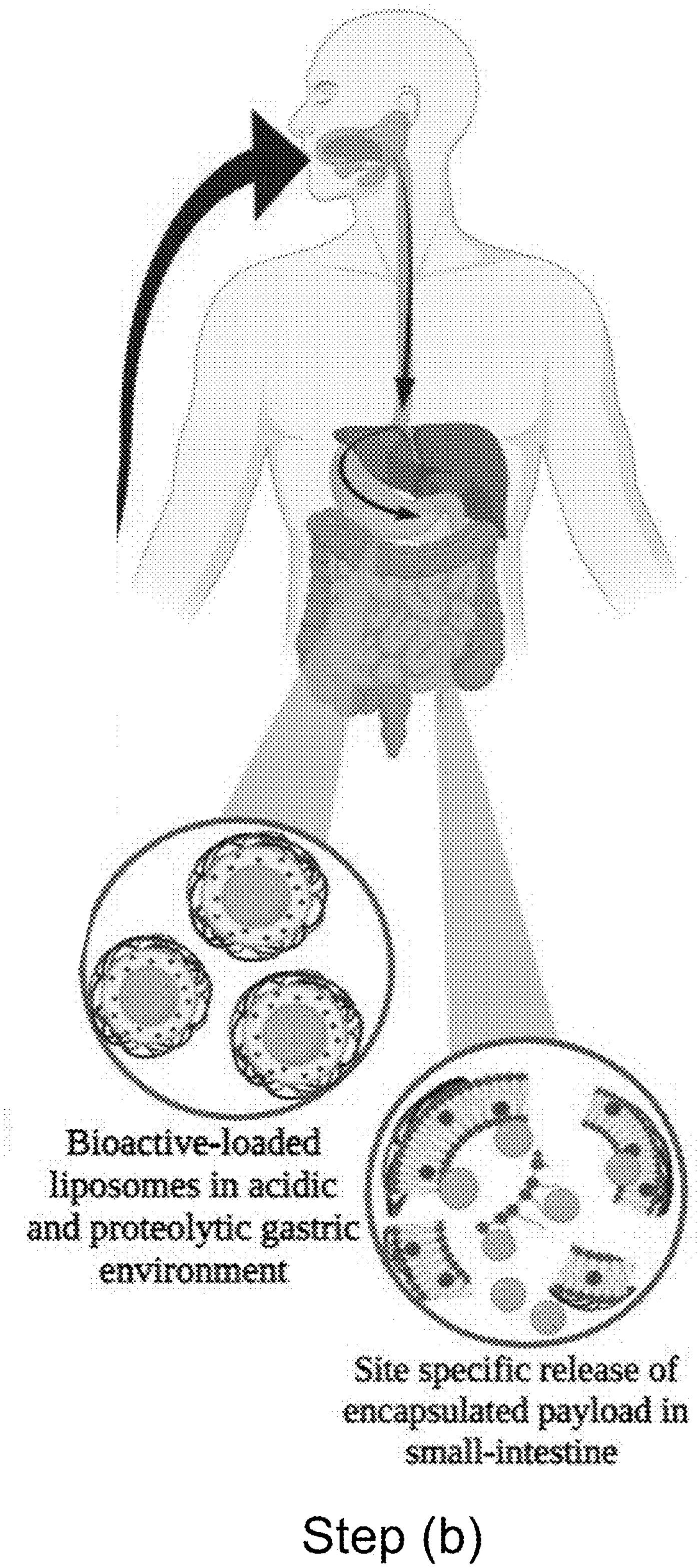
Figure 14:
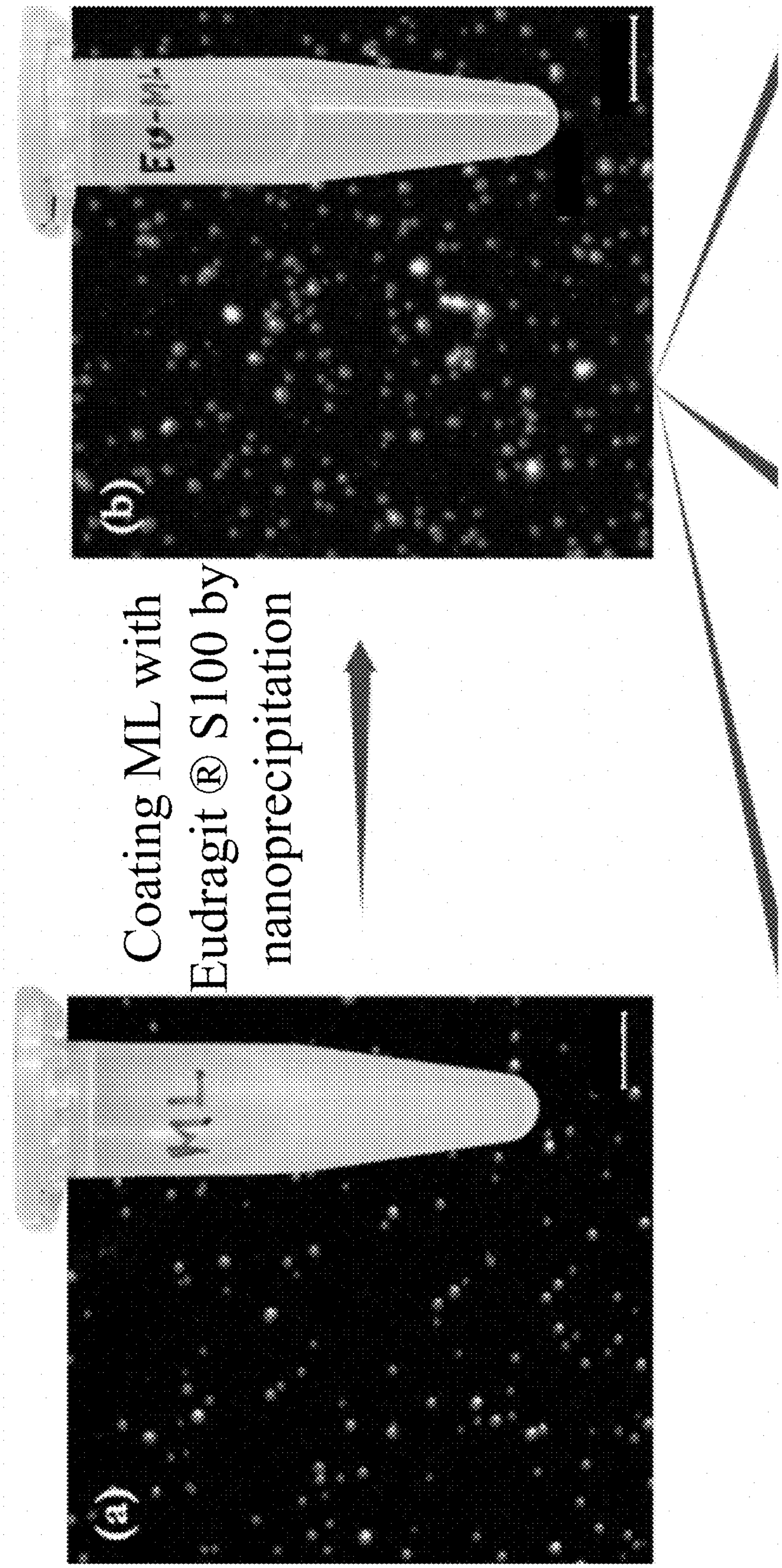
FIG. 14 shows: CLSM images of (Step a) MFGM liposomes (ML); Eudragit® S100 coated MFGM liposomes (Eu-ML)) (Step b) before and after heat-treatment at (Step c) 60, (Step d) 75, and (Step e) 90° C. for 30 min. The inset demonstrates the visual appearance of the corresponding formulation. Scale bars=5 μm.
Figure 14:
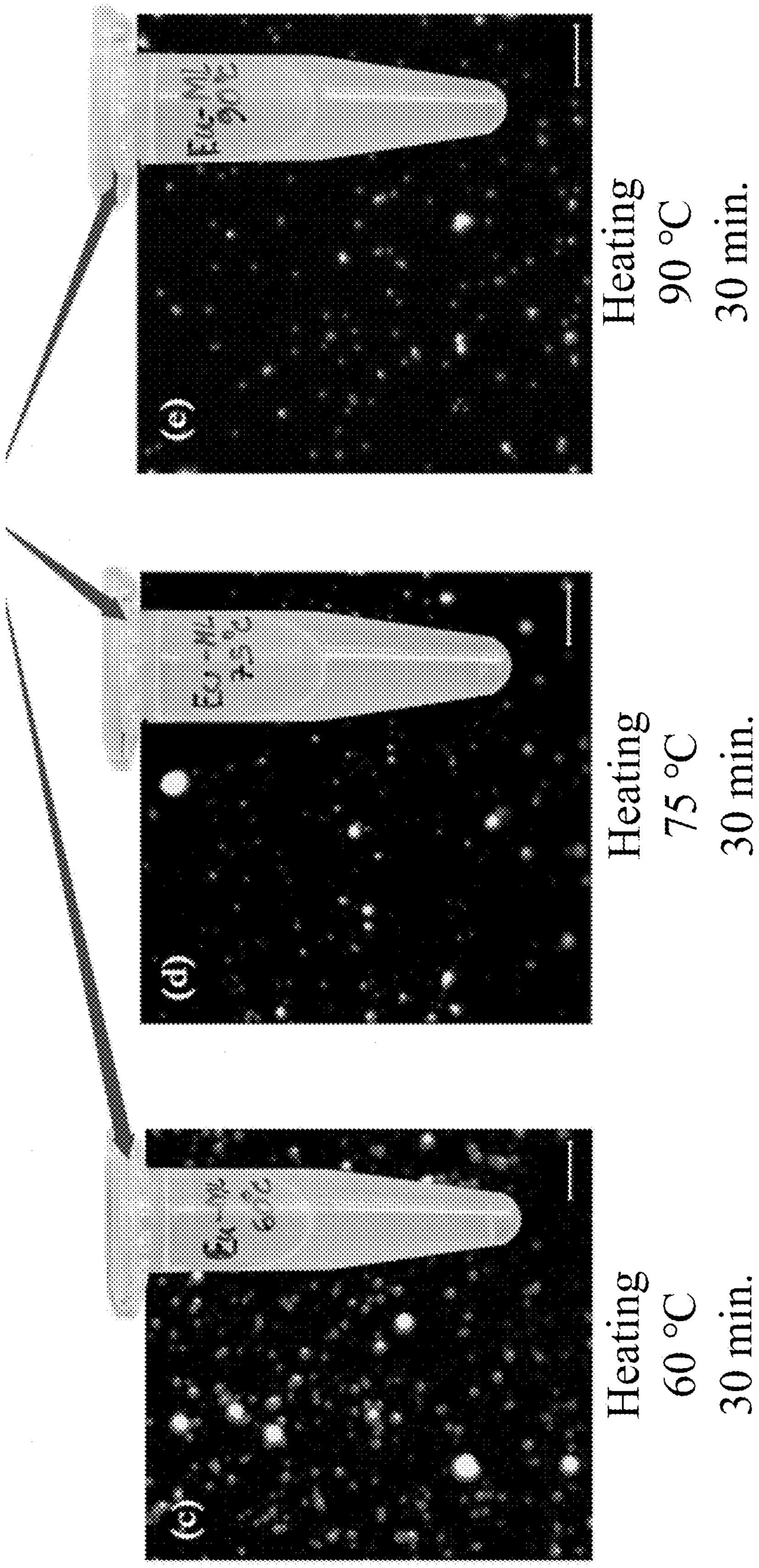

Results and discussion. Multivitamin-loaded liposomes from MFGM-phospholipids (ML) were synthesized with a SC-$CO_2$ based system without using any organic solvents (FIG. 13). The CLSM image of ML is shown in FIG. 14, Step (a). The lipophilic dye Nile red was used to represent the phospholipid bilayer, whereas the hydrophilic dye calcein, which fluoresces bright green, was used to dye the aqueous core. After merging two channels, the bilayer structure of liposomal wall and the core demonstrated red and yellow color, respectively. MLs demonstrated an average diameter and ζ-potential of 429.4±34 nm (FIG. 15) and −45.1±4.36 mV (FIG. 16), respectively. Presence of anionic phospholipids (PS and PI) in addition to the zwitterionic phospholipids (PC, SM, DHSM, and PE) in MFGM, contributes to the negative surface charge of MLs.

Synthesized MLs were coated with Eudragit® S100 (Eu-ML) to protect them from detrimental gastric environment during oral delivery applications along with increasing their ability to retain structural integrity during high-temperature treatment. ML was coated with Eudragit® S100 by nanoprecipitation through a solvent displacement method (FIG. 13). This method helps to facilitate the nanoprecipitation by causing interfacial displacement of a polymer from the solution when its semi-polar solvent is miscible with water. It requires two solvents that are miscible and a polymer that is soluble in one solvent and insoluble in the other one (i.e., non-solvent). To coat ML with Eudragit, PEG and 6-mM acetic acid-sodium acetate buffer (pH 4.5) were used as solvent and non-solvent, respectively. When ML loaded Eudragit-PEG solution is extruded into an acetic acid-sodium acetate buffer, the solvent layer experiences a continuous disintegration process, breaking down into miniscule droplets until only non-divisible liposome-loaded polymer aggregates are left. Precipitation of the polymer matrix from the solvent mixture (i.e., PEG and acetic acid-sodium acetate buffer) through centrifugation followed by washing with the same buffer allowed separation of Eu-MLs. PEG is a non-immunogenic, non-toxic solvent with a broad therapeutic window, and use of PEG enabled us to avoid using any toxic organic solvents, which are frequently used in traditional nano-precipitation methods. The characteristics of synthesized particles formed through nanoprecipitation depends on the interfacial interaction between these two liquid phases, which is dictated by the Marangoni effect. It is suspected that PEG's surface-active properties help to stabilize the interface that is formed between the polymer solution and the water. PEG's ability to interact with other hydrogen bond donors facilitates a strong interaction with the carboxyl group of Eudragit® S100. Thus, in this nanoprecipitation process PEG is not only acting as a solvent but also as a stabilizer.

Figure 15:
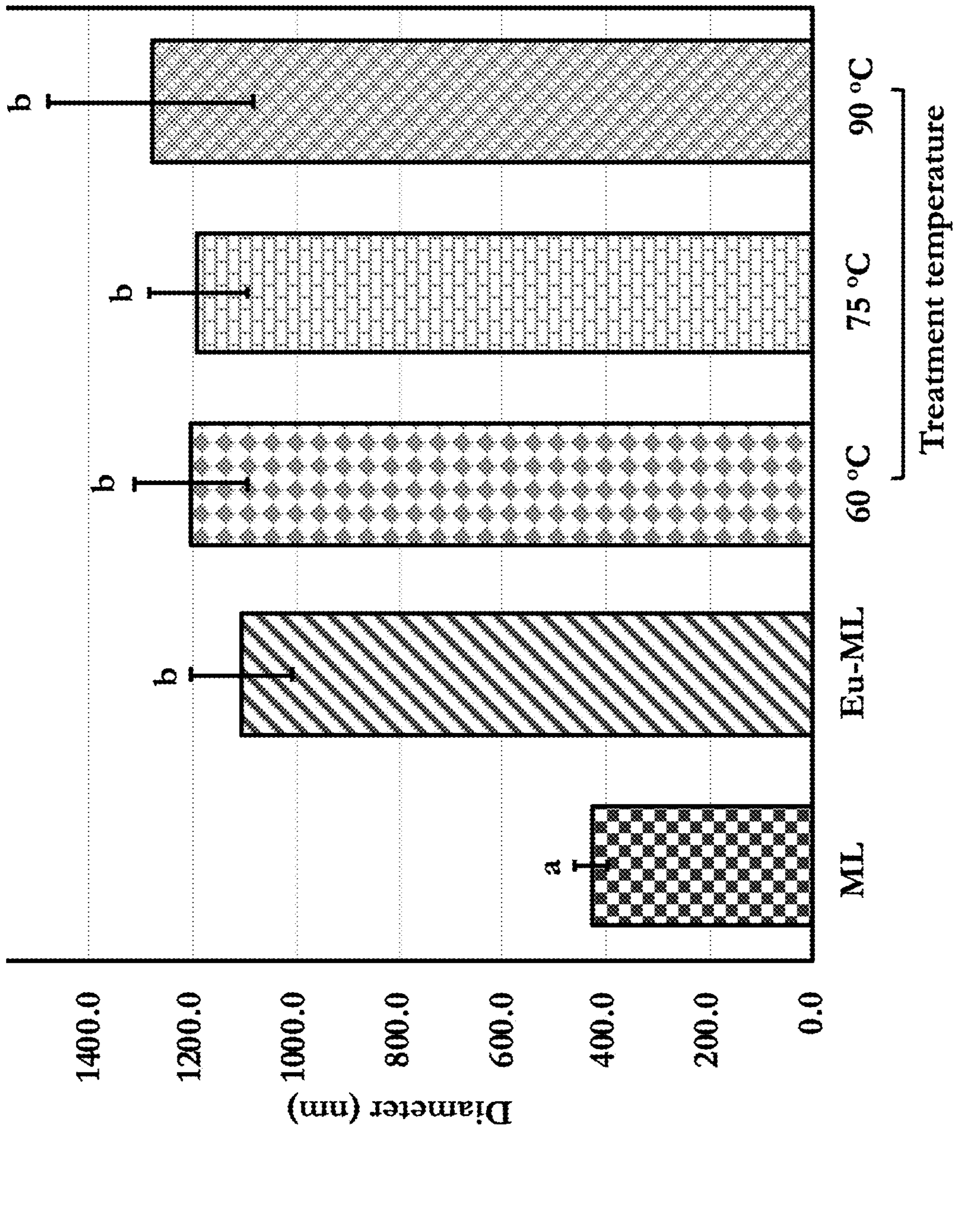
FIG. 15 shows average diameters of: MFGM liposomes (ML); and Eudragit® S100 coated MFGM liposomes (Eu-ML) before and after heat-treatment at 60, 75, and 90° C. for 30 min. Alphabetical labels indicate statistically significant differences between treatments ($p<0.05$).
Figure 16:
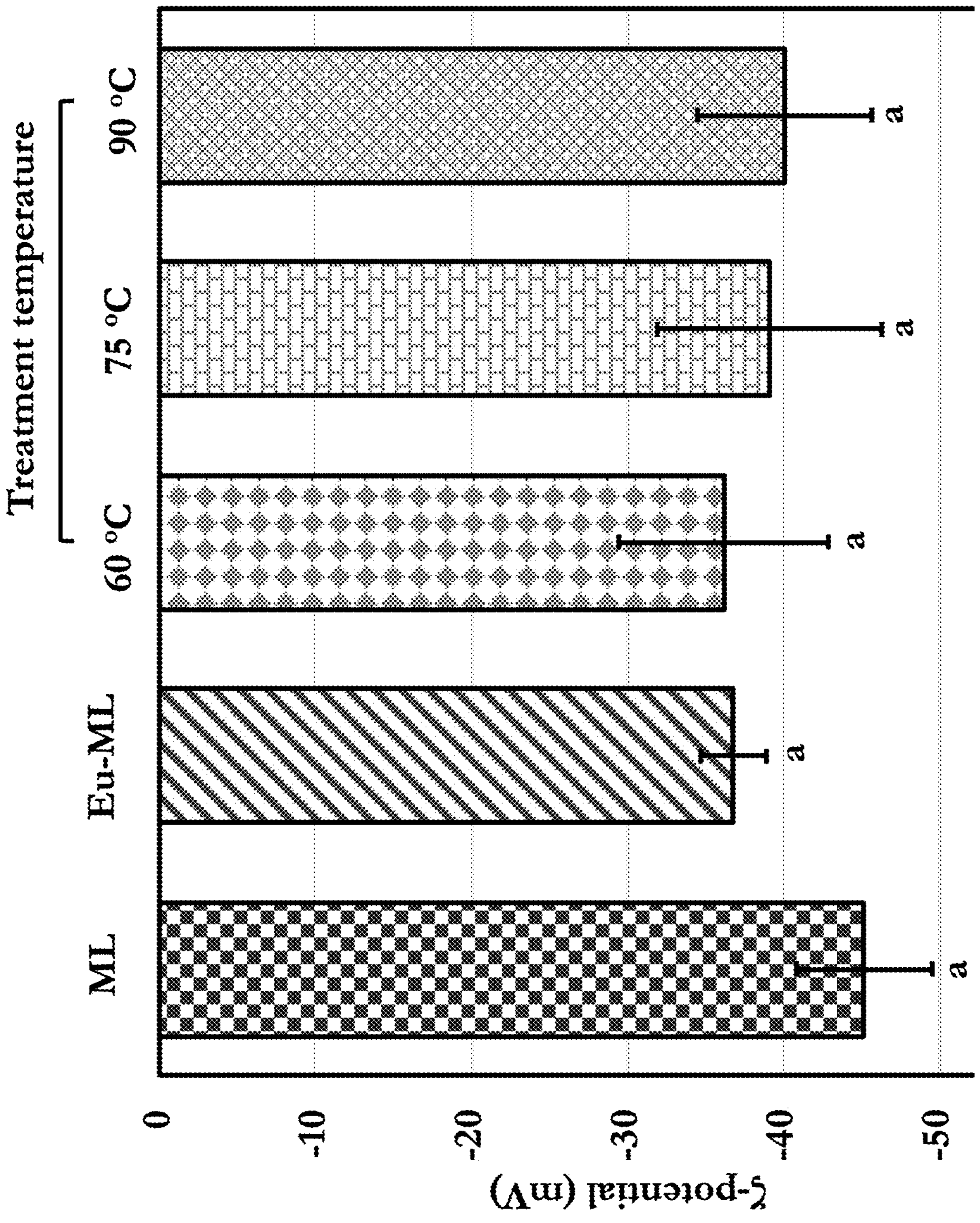
FIG. 16 shows ζ-potentials of: MFGM liposomes (ML); and Eudragit® S100 coated MFGM liposomes (Eu-ML) before and after heat-treatment at 60, 75, and 90° C. for 30 min. Alphabetical labels indicate statistically significant differences between treatments ($p<0.05$).
Figure 17:
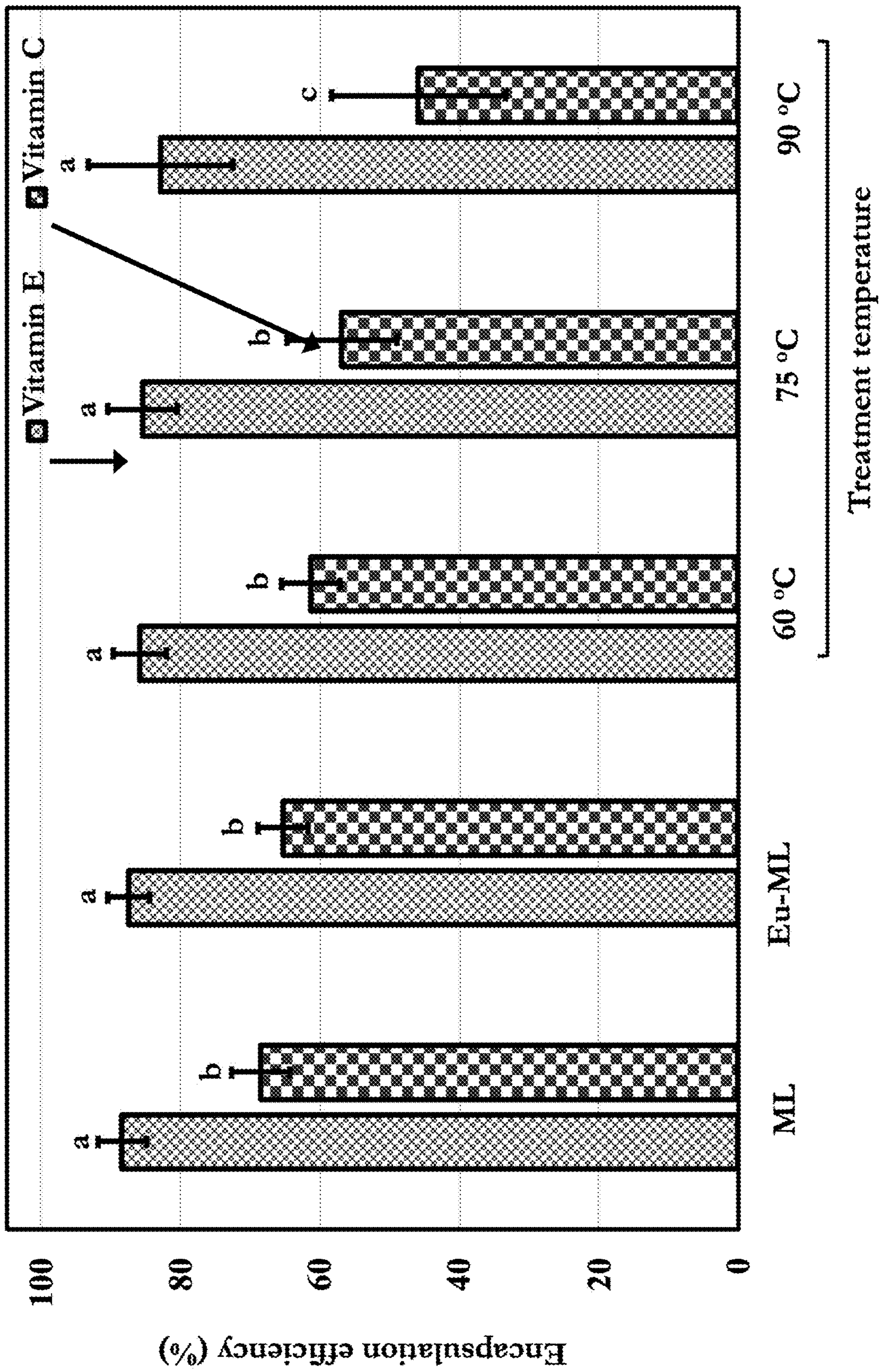
FIG. 17 shows EEs of vitamins E and C in: uncoated MFGM liposomes (ML); and Eudragit® S100 coated MFGM liposomes (Eu-ML) before and after heat-treatment at 60, 75, and 90° C. for 30 min. Alphabetical labels indicate statistically significant differences between treatments ($p<0.05$).
Figure 18:
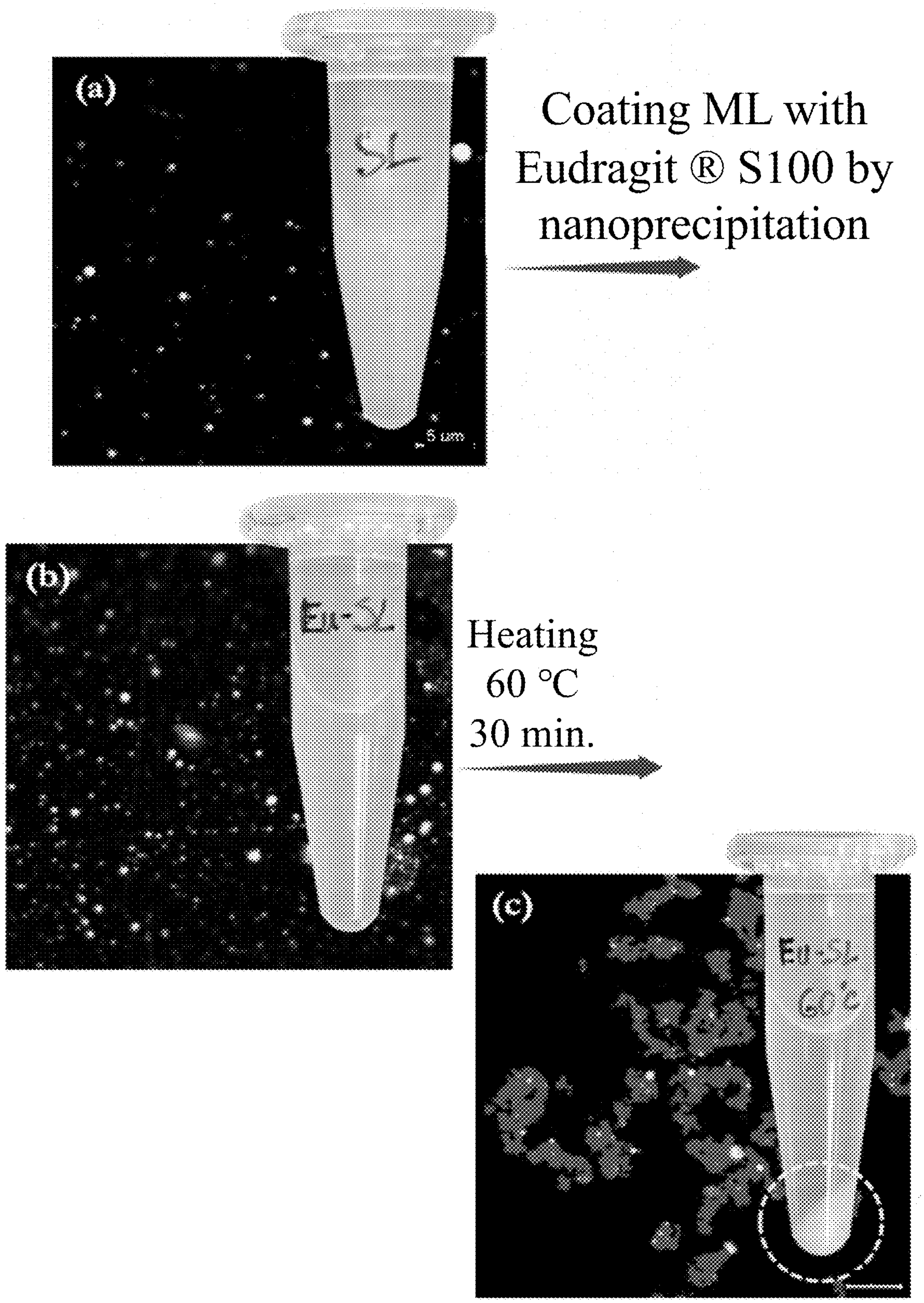
FIG. 18 shows CLSM images of: (Step a) SFPC liposomes (SL); Eudragit® S100 coated SFPC liposomes (Eu-SL) before (Step b) and after (Step c) heat-treatment at 60° C. for 30 minutes. The inset demonstrates the visual appearance of the corresponding formulation. Scale bars=5 μm.
Figure 19A:
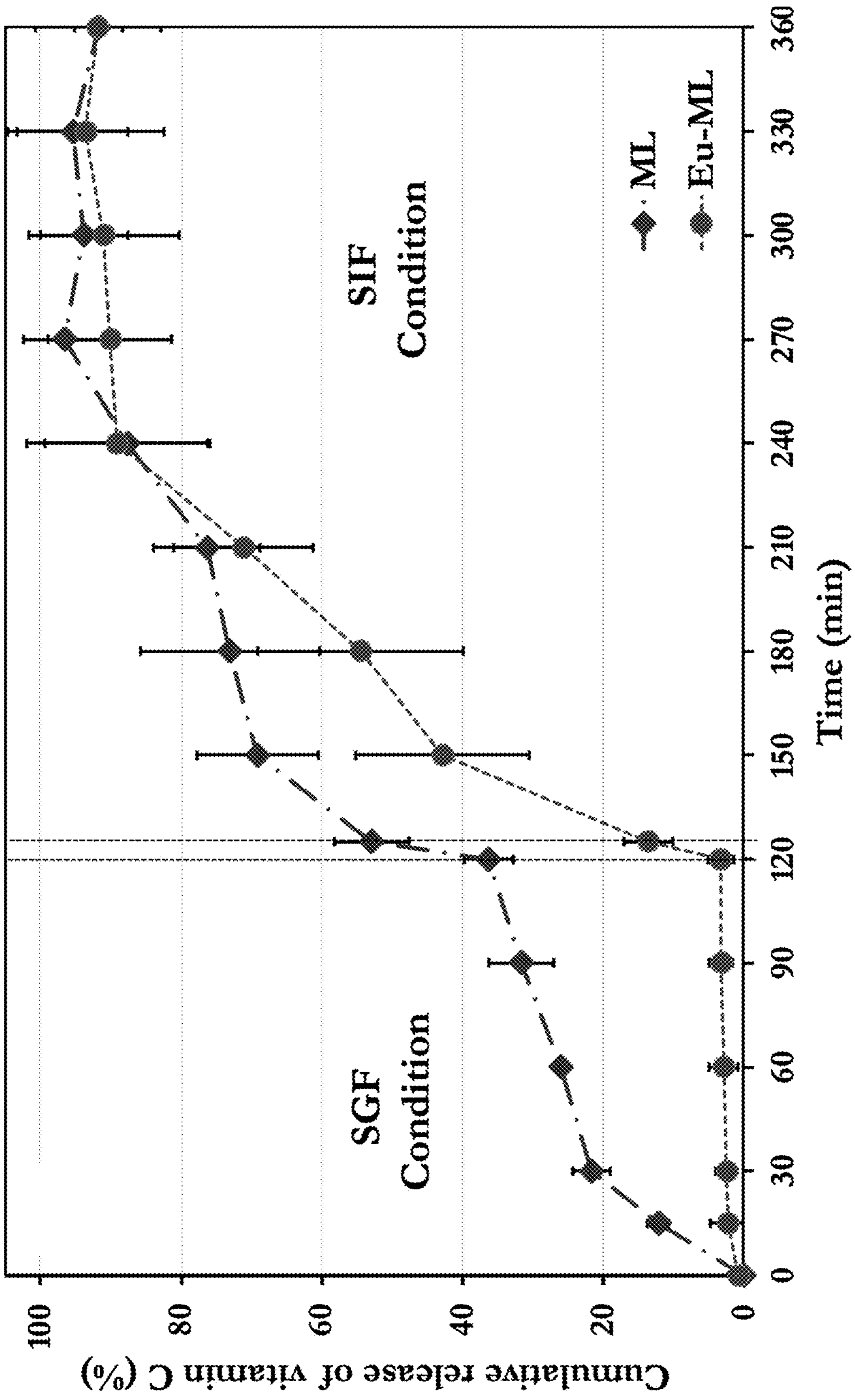
FIG. 19 shows: a cumulative release of (FIG. 19A) vitamin C and (FIG. 19B) vitamin E from uncoated MFGM liposomes (ML), and Eudragit® S100 coated MFGM liposomes (Eu-ML) during treatment in simulated gastric fluid (SGF) for 2 hours (h) followed by treatment in simulated intestinal fluid (SIF) for an additional 4 h.
Figure 19B:
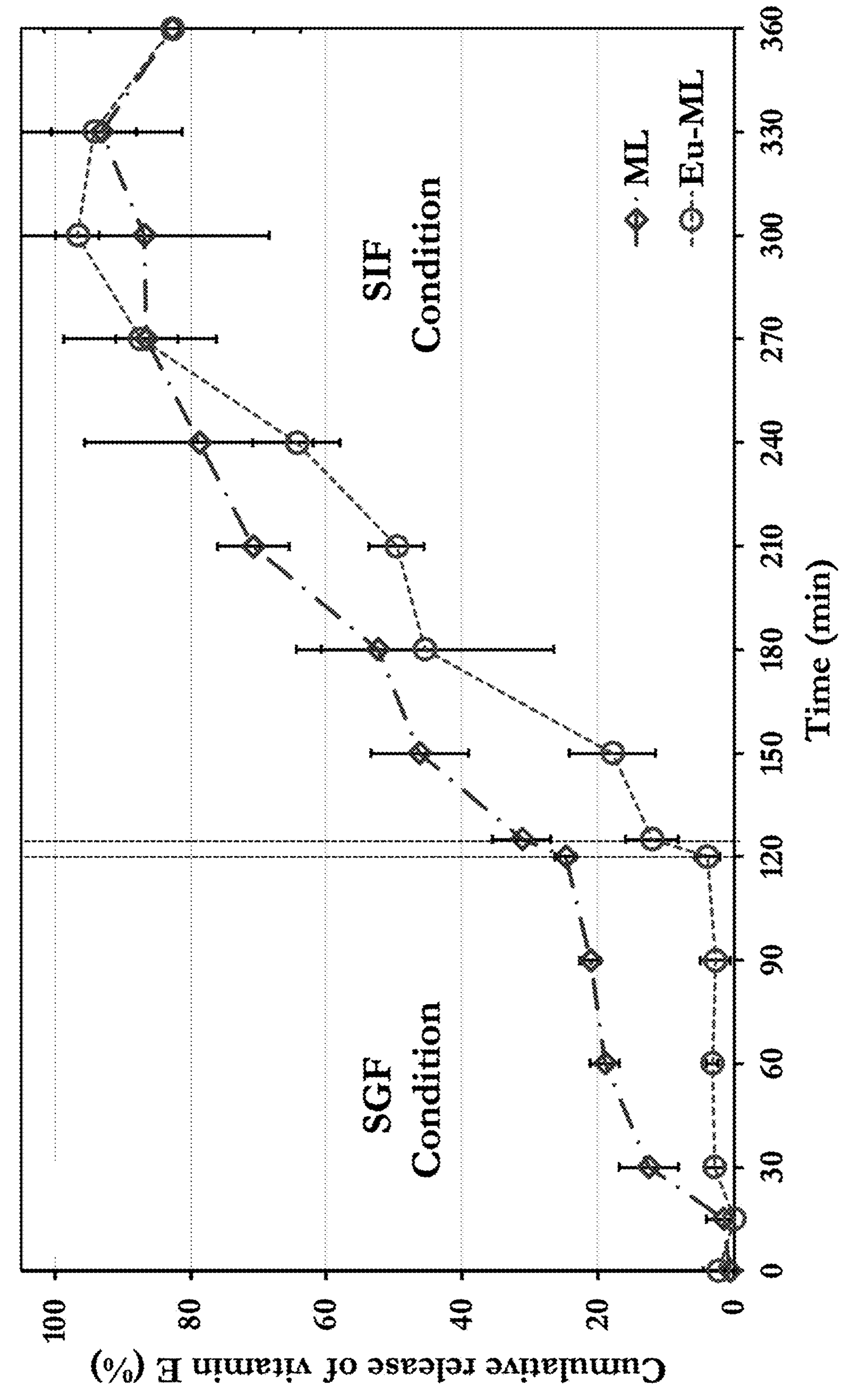

Coating of liposomes with Eudragit® S100 increased the diameter significantly by a factor of 2.57 to give a diameter of 1104.8±96 nm (FIG. 15). When stored in an acetic acid-sodium acetate buffer (pH 4.5), Eu-MLs demonstrated a ζ-potential of ~36.7±2.09 mV (FIG. 16). The negative surface charge of Eudragit-coated liposomes is attributed to the anionic nature of the said polymer and this value is in line with previous research. The CLSM micrographs of Eu-MLs before and after 30 minutes of heat treatment at three different temperature levels (60, 75, and 90° C.) are shown in FIG. 14, Steps (c-e); along with the visual appearance of the corresponding formulation. No changes or formation of precipitate was observed for Eu-MLs after it was subjected to thermal treatment at the abovementioned temperature levels. For Eu-MLs no significant change ($p>0.05$) in diameter and ζ-potential was observed between prior and post heat-treatment at 60, 75 or 90° C. for 30 minutes. As described herein, when uncoated MLs were subjected to heat-treatment, no significant change ($p>0.05$) in liposomal diameter was observed after heating at 60° C. for 30 minutes. However, when heated at 75 and 90° C., the diameter of MLs significantly increased ($p<0.05$). Thus, coating of liposomes with Eudragit helped to sustain liposomal structural integrity. The encapsulation efficiency of vitamins E and C in MLs before and after coating has been shown in FIG. 17. For Eu-MLs, no significant change was observed in terms of vitamin E's EE ($p>0.05$) when subjected to heating at 60-90° C. For vitamin C, the EE did not significantly change at 60-75° C., but decreased significantly ($p<0.05$) after heated at 90° C. The reduction in EE at higher temperature for vitamin C could be attributed to the fact that vitamin C is thermolabile and potentially could have been oxidized to dehydroascorbic acid followed by hydrolysis to 2,3-diketogulonic acid during the heat treatment. For Eu-SLs, heat treatment resulted in significant disruption of the liposomal structure. FIG. 18 juxtaposes SLs (FIG. 18, Step (a)) and Eu-SLs before treatment (FIG. 18, Step (b)) and the fat droplets and remnant liposomes after heat treatment at 60° C. for 30 (FIG. 18, Step (c)). When Eu-SLs was subjected to heating at a temperature of 60° C., they went through complete disintegration yielding lipid and polymer moieties with irregular shape and they precipitated at the bottom of the Eppendorf tube (FIG. 18, Step (c)). This represents the instability of Eu-SLs during thermal treatment at elevated temperature. The stability of both coated and uncoated liposomes was evaluated under simulated gastric and intestinal conditions (FIGS. 19A-19B). For Eu-MLs, in SGF after 2 h of incubation, respectively around 93 and 95% of the encapsulated vitamin C (FIG. 19A) and E (FIG. 19B) remained intact, whereas for uncoated liposomes, 38 and 25% of vitamins C (FIG. 19A) and E (FIG. 19B) were respectively released during 2 h of incubation period. In SIF, coated liposomes released their remaining payload when incubated for 4 h at pH 7.2 (FIGS. 19A-19B).

Previous research has reported similar results. Previous work aimed to increase oral absorption of sorafenib (Sf), a drug often used for the radio therapy of colorectal cancer. TFH method was used to encapsulate sorafenib in liposomes (SfL). The synthesized liposomes were coated with glycol chitosan (G-SfL), followed by another layer of coating with Eudragit® S 100 (E-G-SfL). Encapsulation efficiency of 93 and 90% was observed for E-G-SfL and G-SfL, respectively. Coated liposomes were stable in SGF and were able to retain more than 80% of the encapsulated drug compared to their uncoated counterparts, which showed only 40% retention. At pH 7.4, G-SL and E-G-SL both showed comparable cellular uptake; however, when orally administered in rats, E-G-SfL significantly improved systemic exposure of sorafenib compared to other formulations. In another study reporting similar results, encapsulated recombinant human insulin in liposomes was prepared from soy lecithin and cholesterol. Synthesized liposomes were further coated with protamine sulfate, which was used as a permeation enhancer. Protamine sulfate coated liposomes were encased in an Eudragit® S 100 coated gelatin capsule. After 2 h of incubation in SGF, negligible release of insulin was observed for Eudragit coated liposomes, whereas in SIF, 82% of encapsulated insulin was released. Presence of protamine sulfate coating resulted in enhanced uptake of insulin in Caco-2 cells. Eudragit® S 100 protected liposomes and their encapsulated insulin from proteolytic degradation in the stomach and enabled stable release in intestinal epithelium.

Figure 20A:
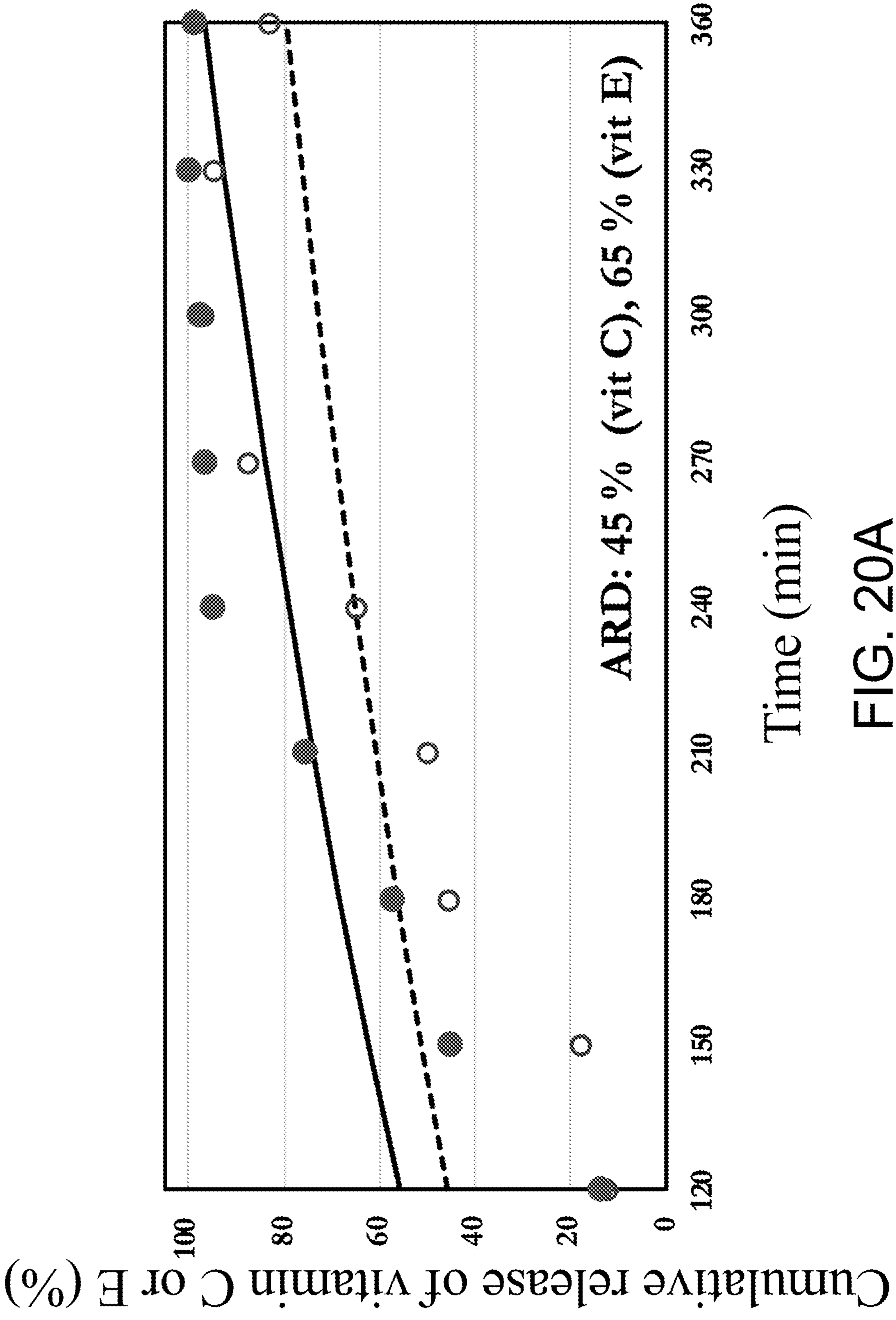
FIGS. 20A-20C show a percent release of vitamins C and E from Eudragit® S100 coated liposomes (Eu-ML) in simulated intestinal fluid for 4 h modeled using (FIG. 20A) the Higuichi Equation.
Figure 20B:
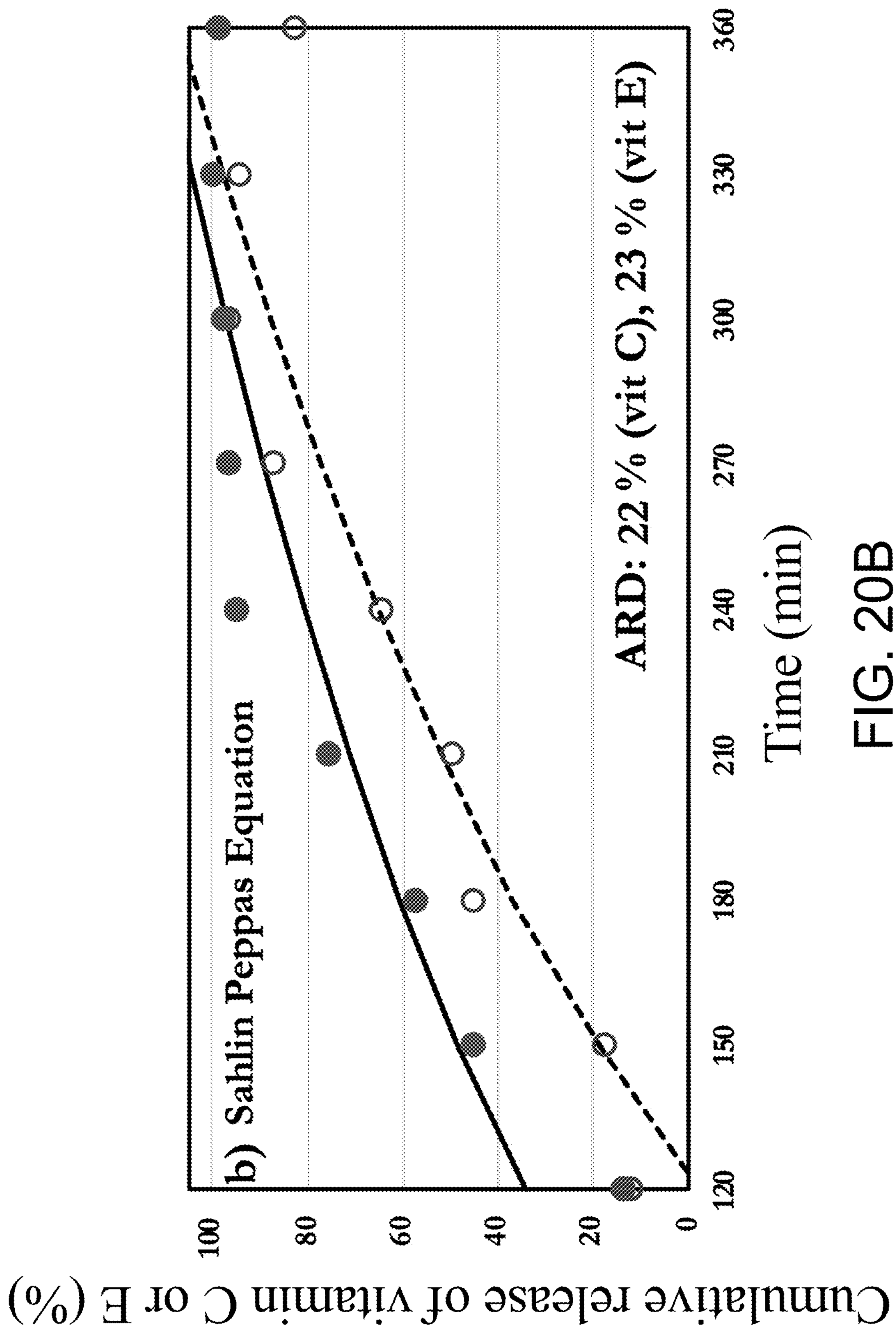
Figure 20C:
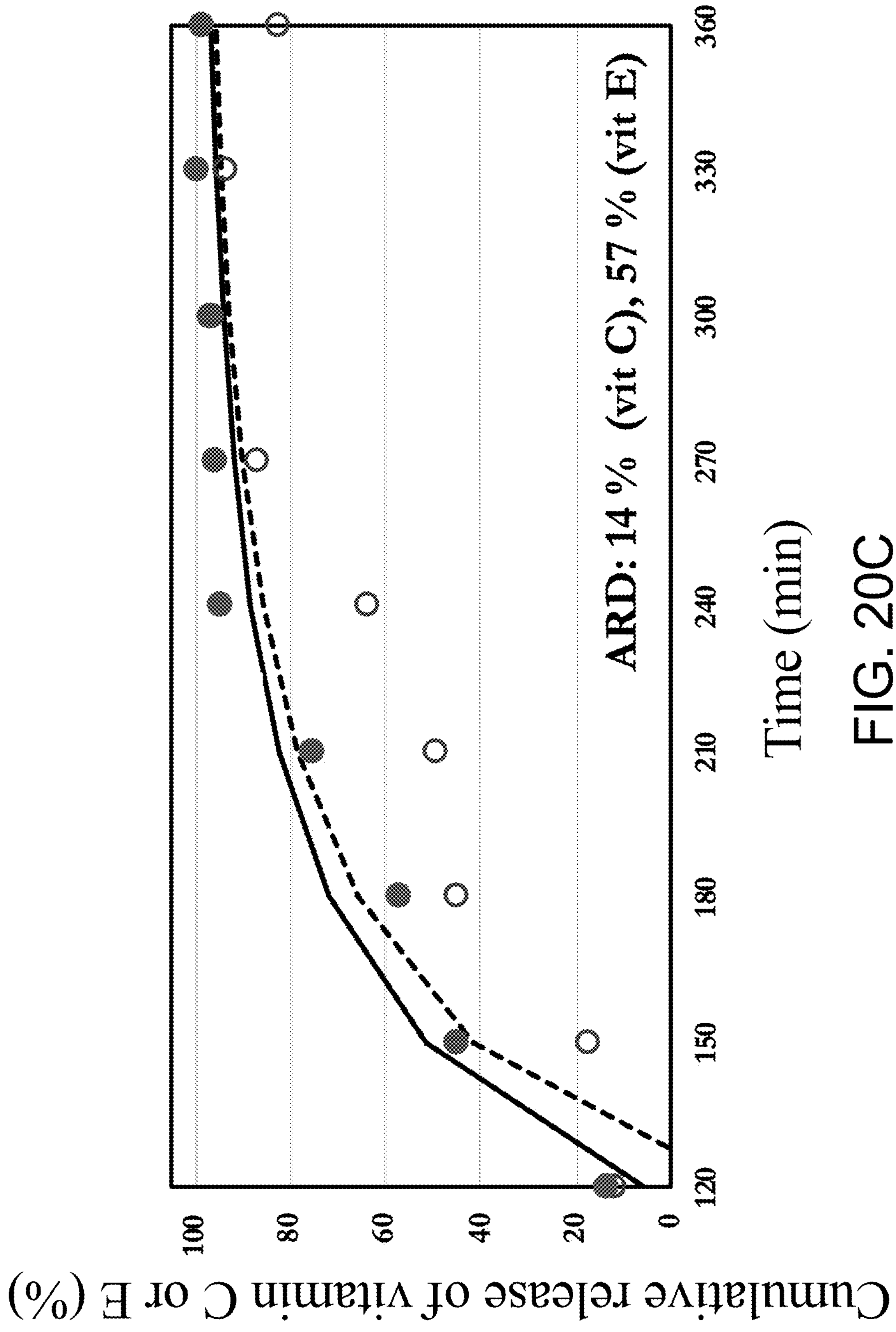

To further elucidate the release kinetics of bioactives from coated liposomes, release of vitamin C and E in SIF from EuMLs was modeled by six different equations as mentioned herein. The goodness of fit for a specific model was determined by measuring the ARD (Eq. 8) and has been mentioned in Table 3 along with the predicted values of other reaction constants. The poor fit of the Higuichi equation (FIG. 20A) indicates that the release of vitamin C and E from liposomal core and bilayer is not completely governed by Fickian diffusion. For vitamin E the best fit was obtained from the Sahlin Peppas equation (ARD=23.35%) (FIG. 20B), which incorporates both Fickian and non-Fickian diffusion. Whereas, for vitamin C The most accurate fit was obtained from Hixon Crowell equation (ARD=14.34%) (FIG. 20C). This indicates that release of vitamins from Eu-MLs is happening through structural disintegration of liposomal vesicles, which is facilitating both Fickian and non-Fickian diffusion.

TABLE 3

| Equations | Coating type: Vitamin C: Constants | R² | ARD (%) | Vitamin E: Constants | R² | ARD (%) |
|---|---|---|---|---|---|---|
| Higuchi equation | $k_H = 5.10\ min^{-0.5}$ | 0.63 | 45.50 | $k_H = 4.20\ min^{-0.5}$ | 0.54 | 65.00 |
| Korsmeyer-Peppas equation | $k_{KP} = 0.36\ min^{-0.98}$ n = 0.98 | 0.82 | 27.67 | $k_{KP} = 0.04\ min^{-1.32}$ n = 1.32 | 0.84 | 29.27 |
| Sahlin-Peppas equation | $k_{SP1} = -669.2\ min^{-0.06}$ $k_{SP2} = 509.9\ min^{-0.12}$ n = 0.06 | 0.82 | 22.43 | $k_{SP1} = -2872\ min^{-0.03}$ $k_{SP2} = 2500\ min{-}^{0.06}$ n = 0.03 | 0.87 | 22.80 |
| Zeroth order equation | $k_0 = 0.73\% \cdot min^{-1}$ | 0.77 | 34.19 | $k_0 = 0.61\% \cdot min^{-1}$ | 0.70 | 52.69 |
| First order equation | $k_1 = 0.26\ min^{-1}$ | 0.82 | 27.24 | $k_1 = 0.21\ min^{-1}$ | 0.80 | 40.28 |
| Hixon Crowell equation | $k_{HC} = 0.01\%^{0.33} \cdot min^{-1}$ | 0.93 | 14.34 | $k_{HC} = 0.01\%^{0.33} \cdot min^{-1}$ | 0.61 | 56.87 |

Conclusion. This example developed a green, sustainable, and novel technology amenable to industrial scale synthesis of multivitamin-loaded and surface-modified liposomal microcapsules which are heat-stable and tailored for site-specific intestinal delivery. Liposomes were synthesized from MFGM phospholipids (ML) and were coated with a commercially available pH responsive polymer Eudragit® S100 (Eu-MLs). Vitamins E and C were used as model lipophilic and hydrophilic bioactives to evaluate the effectiveness of Eu-MLs for bioactive encapsulation. To determine heat stability, Eu-MLs were heated to 60, 75, and 90° C. for 30 minutes and were observed to be heat stable, as established by their CLSM images, structural characterization, and EE. Whereas, coated SFPC based liposomes, Eu-SLs, disintegrated when treated at 60° C. The polymer coating protected encapsulated payloads from acid hydrolysis and enzymatic degradation in the in vitro simulated gastric environment and facilitated subsequent delivery of payloads in the in vitro simulated intestinal condition. These Eudragit® S100 coated liposomal microcapsules are non-toxic, biodegradable, and smartly designed for site-specific, triggered release of encapsulated cargo. Their ability to simultaneously co-encapsulate both lipophilic and hydrophilic cargos while maintain heat stability will make them highly suitable for potential effective oral delivery of bioactive compounds in pharmaceutical and food applications.

Various modifications and variations of the described methods, pharmaceutical compositions, and kits of the present disclosure will be apparent to those skilled in the art without departing from the scope and spirit of the present disclosure. Although the present disclosure has been described in connection with specific embodiments, it will be understood that it is capable of further modifications and that the present disclosure as claimed should not be unduly limited to such specific embodiments. Indeed, various modifications of the described modes for carrying out the present disclosure that are obvious to those skilled in the art are intended to be within the scope of the present disclosure. This application is intended to cover any variations, uses, or adaptations of the present disclosure following, in general, the principles of the present disclosure and including such departures from the present disclosure come within known customary practice within the art to which the present disclosure pertains and may be applied to the essential features herein before set forth.

The invention claimed is:

1. A method for preparing a milk fat globule membrane (MFGM) phospholipid extract from a milk product, the method comprising:

extracting a nonpolar lipid fraction of a milk product with supercritical carbon dioxide (SC-$CO_2$), with a proviso that, prior to the extracting the nonpolar lipid fraction, the milk product is not contacted with an enzyme, is not filtered, or any combination thereof, wherein the extracting the nonpolar lipid fraction of the milk product with SC-$CO_2$ is performed at a temperature of about 50° C. to about 60° C. and at a pressure of about 30 MPa to about 40 MPa; and subsequently, extracting a polar lipid fraction of the milk product from which the nonpolar lipid fraction has been extracted with a supercritical fluid comprising SC-$CO_2$ and one or more polar co-solvent(s), wherein the supercritical fluid comprises about 5 weight percent (wt. %) to about 20 wt. % of the polar co-solvent(s), based on a total weight of SC-$CO_2$ and the polar co-solvent(s), wherein the extracting the polar lipid fraction of the milk product with supercritical fluid is performed at a temperature of about 50° C. to about 60° C. and at a pressure of about 30 MPa to about 40 MPa, wherein the polar lipid fraction is the MFGM phospholipid extract, wherein the MFGM phospholipid extract comprises about 40 wt. % to about 85 wt. % phospholipids, based on the total weight of the lipids, the MFGM phospholipid extract comprises sphingomyelin (SM), phosphatidylethanolamine (PE), and phosphatidylcholine (PC) and a weight ratio of PC to SM is about 1.6/1 or greater, a weight ratio of PC to PE is about 2.0/1 or greater, and a weight ratio of SM to PE is about 1.2/1 or greater, and the MFGM phospholipid extract is substantially free of sugars, proteins, nonpolar lipids, or any combination thereof.

2. The method of claim 1, wherein the milk product is chosen from buttermilk powder, whey protein phospholipid concentrate, and any combination thereof.

3. The method of claim 1, wherein the polar co-solvent(s) is/are chosen from ethanol, methanol, acetone, hexane, acetonitrile, and any combination thereof.

4. The method of claim 1, wherein the extracting the nonpolar lipid fraction of the milk product with SC-$CO_2$ and the extracting the polar lipid fraction of the milk product with the supercritical fluid each comprise: extracting under static conditions for at least a portion of the extracting; and extracting under dynamic conditions for at least a portion of the the extracting.

5. The method of claim 1, wherein, after the extracting the polar lipid fraction of the milk product with the supercritical fluid, the method further comprises removing at least a portion of or all of the polar co-solvent(s), if present, from the MFGM phospholipid extract.

6. A method for preparing one or more liposome(s) comprising:

generating a pressurized mixture comprising supercritical carbon dioxide (SC-CO2) and a milk fat globule membrane (MFGM) phospholipid extract prepared according to the method of claim 1;

releasing an at least partially or completely depressurized mixture stream from the pressurized mixture; and mixing the depressurized mixture stream and an aqueous stream, thereby forming the liposome(s).

7. The method of claim 6, wherein:

the pressurized mixture further comprises a lipophilic cargo comprising one or more polycyclic amphiphilic compounds(s), one or more hydrophobic compound(s), one or more amphiphilic compound(s), or any combination thereof, wherein the hydrophobic compound(s) is/are chosen from hydrophobic therapeutic agent(s), hydrophobic nutrient(s), hydrophobic bioactive agent(s), and any combination thereof, and wherein the amphiphilic compound(s) is/are chosen from amphiphilic therapeutic agent(s), amphiphilic nutrient(s), amphiphilic bioactive agent(s), and any combination thereof; and/or the aqueous stream further comprises an aqueous cargo comprising one or more hydrophilic compound(s), one or more of the amphiphilic compound(s), or any combination thereof, wherein the hydrophilic compound(s) chosen from hydrophilic therapeutic agent(s), hydrophilic nutrient(s), hydrophilic bioactive agent(s), and any combination thereof, and wherein at least a portion of or all of the lipophilic cargo, at least a portion of or all of the aqueous cargo, or any combination thereof, if present, are disposed in the liposome(s).

8. The method of claim 7, wherein:

from about 85% to about 95% of the polycyclic amphiphilic compound(s), the hydrophobic compound(s), the amphiphilic compound(s), or any combination thereof, of the lipophilic cargo is/are disposed in the liposome(s); and/or from about 60% to about 70% of the hydrophobic compound(s), the amphiphilic compound(s), or any combination thereof, of the aqueous cargo is/are disposed in the liposome(s).

9. The method of claim 6, wherein the pressurized mixture is generated at:

a pressure of about 10 MPa to about 40 MPa; and/or a temperature of about 20 °C to about 60 °C.

10. The method of claim 6, further comprising forming an aqueous dispersion of the liposome(s).

11. The method of claim 6, wherein the method further comprises coating at least a portion of or all of an exterior surface or surfaces of one or more or all of the liposome(s) with one or more enteric material(s).

* * * * *